(12) United States Patent
Stillman

(10) Patent No.: US 7,115,297 B2
(45) Date of Patent: Oct. 3, 2006

(54) NUTRITIONALLY FORTIFIED LIQUID COMPOSITION WITH ADDED VALUE DELIVERY SYSTEMS/ELEMENTS/ADDITIVES

(76) Inventor: Suzanne Jaffe Stillman, 1712 S. Barington Ave., #4, Los Angeles, CA (US) 90025

( * ) Notice: Subject to any disclaimer, the term of this patent is extended or adjusted under 35 U.S.C. 154(b) by 118 days.

(21) Appl. No.: 10/244,699

(22) Filed: Sep. 16, 2002

(65) Prior Publication Data

US 2003/0064104 A1 Apr. 3, 2003

Related U.S. Application Data

(63) Continuation-in-part of application No. 10/204,572, filed on Apr. 2, 2003, which is a continuation of application No. PCT/US01/05630, filed on Feb. 22, 2001.

(51) Int. Cl.
*A23L 2/00* (2006.01)

(52) U.S. Cl. ............... 426/590; 426/594; 426/72; 426/73; 426/74

(58) Field of Classification Search ............ 426/590, 426/72, 73, 74, 594, 729; 424/442, 450, 455
See application file for complete search history.

(56) References Cited

U.S. PATENT DOCUMENTS

| | | |
|---|---|---|
| 2,224,252 A | 12/1940 | Callaway |
| 3,009,859 A | 11/1961 | Laborit et al. .............. 167/65 |
| 3,111,641 A | 11/1963 | Sperti et al. .............. 99/105 |
| 3,227,562 A | 1/1966 | Houghtaling et al. ......... 99/205 |
| 3,337,404 A | 8/1967 | Polli et al. ............... 167/57 |
| 3,564,740 A | 2/1971 | Calfee |
| 4,034,493 A | 7/1977 | Ball |
| 4,042,684 A | 8/1977 | Kahm |
| 4,154,814 A | 5/1979 | Hand et al. |
| 4,187,194 A | 2/1980 | Wellman et al. |
| 4,211,668 A | 7/1980 | Tate |
| 4,217,370 A | 8/1980 | Rawlings et al. |
| 4,283,432 A | 8/1981 | Mitchell et al. ............. 426/466 |
| 4,309,417 A | 1/1982 | Staples |
| 4,315,513 A | 2/1982 | Nawash et al. |
| 4,393,873 A | 7/1983 | Nawash et al. |
| 4,444,761 A | 4/1984 | Spiller ................... 514/57 |
| 4,447,532 A | 5/1984 | Coker et al. ............... 435/99 |
| 4,448,770 A | 5/1984 | Epting, Jr. |
| 4,497,793 A | 2/1985 | Simkin |
| 4,689,235 A | 8/1987 | Barnes et al. |
| 4,711,784 A | 12/1987 | Yang |
| 4,738,856 A | 4/1988 | Clark |
| 4,749,575 A | 6/1988 | Rotman |
| 4,777,042 A | 10/1988 | Toda et al. |
| 4,778,677 A | 10/1988 | Ebbesen |
| 4,784,861 A | 11/1988 | Gori |
| 4,834,990 A | 5/1989 | Amer ..................... 46/74 |
| 4,849,222 A | 7/1989 | Broaddus ................ 424/738 |
| 4,911,889 A | 3/1990 | Leland et al. .............. 422/26 |
| 4,953,572 A | 9/1990 | Rose et al. |
| 4,988,530 A | 1/1991 | Hoersten et al. ............ 426/577 |
| 4,996,063 A | 2/1991 | Inglett ................... 426/21 |
| 4,998,530 A | 3/1991 | DonMichael |
| 5,002,934 A | 3/1991 | Norton et al. |
| 5,009,819 A | 4/1991 | Popescu et al. |
| 5,019,400 A | 5/1991 | Gombotz et al. |
| 5,019,594 A | 5/1991 | Wurtman et al. |
| 5,024,842 A | 6/1991 | Edgren et al. |
| 5,032,411 A | 7/1991 | Stray-Gundersen .......... 426/74 |
| 5,051,261 A | 9/1991 | McGinity et al. |
| 5,055,460 A | 10/1991 | Friedlander |
| 5,077,057 A | 12/1991 | Szoka, Jr. |
| 5,082,673 A | 1/1992 | Inglett ................... 426/21 |
| 5,108,774 A | 4/1992 | Mills et al. ............... 426/599 |
| 5,126,332 A | 6/1992 | Ohta et al. |

(Continued)

FOREIGN PATENT DOCUMENTS

| | | |
|---|---|---|
| FR | 2 586 532 | 3/1987 |
| JP | 10-09520 | 1/1989 |
| JP | 6-100442 | 4/1994 |
| JP | 8-275752 | 10/1996 |
| JP | 9-020660 | 1/1997 |
| WO | 01/62108 | 8/2001 |

OTHER PUBLICATIONS

A. Golay et al., "The effect of a liquid supplement containing guar gum and fructose on glucose tolerance in non–insulin–dependent diabetic patients," Nutr. Metab. Cardiovasc. Dis (1995) 5:141–148 (abstract).

(Continued)

*Primary Examiner*—N. Bhat
(74) *Attorney, Agent, or Firm*—Patton Boggs LLP

(57) ABSTRACT

A shelf-stable, ready to use, water-like composition for humans/animals; as an adjunct to fiber-water, and/or safe drinking water, consumed directly, tube feedings, or in the preparation/reconstitution of food(s)/beverage(s). Fortified Fiber-Water is fiber-water, with added delivery systems: Encapsulations/particles, of different size(s), shape(s), material(s), colors, non-visible, serving one or more functions: improved taste, odor-masking; controlled release applications; bio-availability of actives, avoid hygroscopicity; minimized interactions, improved thermal, oxidative, and shelf-life; decorative. Viscosity changing elements, (with one or more viscosity changing additives, with or without encapsulations, particles) to enhance delivery of active medicants/ingredients of categories: pharmaceuticals, nutraceuticals, dietary supplements, therapeutics, diagnostics, etc. Composition ensures hydration, simultaneously providing soluble fiber (fiber-water), with additives contained within the delivery systems, having the ability to target specific health goals/needs: weight loss, diabetes, cholesterol/heart, gastrointestinal tract disorders/improvement, osteoporosis, cancer, pain, stress, relaxant, stimulant etc.

111 Claims, No Drawings

U.S. PATENT DOCUMENTS

| | | | |
|---|---|---|---|
| 5,149,541 A | 9/1992 | Leis, Jr. et al. | 424/489 |
| 5,162,128 A | 11/1992 | Mills et al. | 426/599 |
| 5,209,978 A | 5/1993 | Kosaka et al. | |
| 5,215,750 A | 6/1993 | Keane, II | |
| 5,219,570 A | 6/1993 | Barbera | 424/738 |
| 5,223,268 A | 6/1993 | Stetsko et al. | |
| 5,225,219 A | 7/1993 | Inglett | 426/28 |
| 5,229,117 A | 7/1993 | Leland et al. | 424/738 |
| 5,229,172 A | 7/1993 | Cahalan et al. | 427/536 |
| 5,260,279 A | 11/1993 | Greenberg | |
| 5,270,297 A | 12/1993 | Paul et al. | |
| 5,273,754 A | 12/1993 | Mann | |
| 5,294,458 A | 3/1994 | Fujimori | |
| 5,294,606 A | 3/1994 | Hastings | |
| 5,344,824 A | 9/1994 | Ohkuma et al. | 514/58 |
| 5,358,729 A | 10/1994 | Ohkuma et al. | 426/567 |
| 5,364,652 A | 11/1994 | Ohkuma et al. | 426/549 |
| 5,374,444 A | 12/1994 | Langner | |
| 5,378,474 A | 1/1995 | Morella et al. | |
| 5,380,717 A | 1/1995 | Ohkuma et al. | 514/58 |
| 5,397,786 A | 3/1995 | Simone | |
| 5,405,836 A | 4/1995 | Richar et al. | |
| 5,422,352 A | 6/1995 | Astrup | |
| 5,430,141 A | 7/1995 | Ohkuma et al. | 536/103 |
| 5,447,730 A | 9/1995 | Greenleaf | 424/680 |
| 5,456,985 A | 10/1995 | Zgoulli et al. | |
| 5,458,893 A | 10/1995 | Smith | |
| 5,472,732 A | 12/1995 | Ohkuma et al. | 426/658 |
| 5,505,981 A | 4/1996 | Wakabayashi et al. | 426/658 |
| 5,516,535 A * | 5/1996 | Heckert et al. | 426/2 |
| 5,519,011 A | 5/1996 | Wakabayashi et al. | 514/58 |
| 5,531,734 A | 7/1996 | Geckle et al. | |
| 5,543,405 A | 8/1996 | Keown et al. | |
| 5,550,113 A | 8/1996 | Mann | |
| 5,558,897 A | 9/1996 | Goldman | |
| 5,567,424 A * | 10/1996 | Hastings | 424/195.17 |
| 5,571,441 A | 11/1996 | Andon et al. | |
| 5,587,197 A | 12/1996 | Maeda et al. | 426/658 |
| 5,597,604 A | 1/1997 | Chalupa et al. | |
| 5,605,697 A | 2/1997 | Asano et al. | |
| 5,612,026 A | 3/1997 | Diehl | |
| 5,620,873 A | 4/1997 | Ohkuma et al. | 435/99 |
| 5,653,996 A | 8/1997 | Hsu | |
| 5,672,301 A | 9/1997 | Orly et al. | |
| 5,681,606 A | 10/1997 | Hutchison et al. | |
| 5,698,437 A | 12/1997 | Matsuda et al. | |
| 5,700,484 A | 12/1997 | Chauffard et al. | |
| 5,721,345 A | 2/1998 | Roberfroid et al. | |
| 5,753,295 A | 5/1998 | Goldman | |
| 5,755,688 A | 5/1998 | Piontek et al. | 604/83 |
| 5,776,524 A | 7/1998 | Reinhart | |
| 5,780,060 A | 7/1998 | Levy et al. | |
| 5,792,754 A | 8/1998 | Green et al. | |
| 5,810,018 A | 9/1998 | Monte | |
| 5,824,353 A * | 10/1998 | Tsunoda et al. | 426/66 |
| 5,851,578 A | 12/1998 | Gandhi | 426/590 |
| 5,880,109 A | 3/1999 | Nakamura et al. | |
| 5,891,465 A | 4/1999 | Keller et al. | |
| 5,900,251 A | 5/1999 | Raissen | |
| 5,904,851 A | 5/1999 | Taylor et al. | |
| 5,922,346 A | 7/1999 | Hersh | |
| 5,922,350 A | 7/1999 | Janoff et al. | |
| 5,935,826 A | 8/1999 | Blue et al. | |
| 5,958,456 A | 9/1999 | Baichwal et al. | |
| 5,958,497 A | 9/1999 | Grimm et al. | 426/596 |
| 5,962,015 A | 10/1999 | Delrieu et al. | |
| 5,968,365 A | 10/1999 | Laurenzo et al. | 210/641 |
| 5,968,569 A | 10/1999 | Cavadini et al. | |
| 5,972,415 A | 10/1999 | Brassart et al. | |
| 5,976,603 A | 11/1999 | Kota et al. | 426/590 |
| 5,977,175 A | 11/1999 | Lin | |
| 5,985,282 A | 11/1999 | Haveson | |
| 5,989,574 A | 11/1999 | Slavin | |
| 5,993,880 A | 11/1999 | Frost et al. | |
| 5,997,917 A | 12/1999 | Uchida et al. | 426/96 |
| 6,001,554 A | 12/1999 | Boyle et al. | |
| 6,004,610 A | 12/1999 | Wang et al. | 426/599 |
| 6,007,838 A | 12/1999 | Alving et al. | |
| 6,013,622 A | 1/2000 | Bruno et al. | |
| 6,017,550 A * | 1/2000 | Berk et al. | 424/401 |
| 6,020,002 A | 2/2000 | Myers et al. | |
| 6,020,016 A | 2/2000 | Castleberry | 426/590 |
| 6,022,500 A | 2/2000 | John et al. | |
| 6,022,525 A | 2/2000 | Sutton et al. | |
| 6,030,605 A | 2/2000 | D'Ameila et al. | |
| 6,033,713 A * | 3/2000 | Sheldon | 426/590 |
| 6,033,888 A | 3/2000 | Batich et al. | |
| 6,039,952 A | 3/2000 | Sunvold et al. | |
| 6,042,854 A * | 3/2000 | Morris et al. | 426/72 |
| 6,077,504 A | 6/2000 | Vesley et al. | |
| 6,077,872 A | 6/2000 | Yu et al. | |
| 6,102,224 A | 8/2000 | Sun et al. | |
| 6,120,803 A | 9/2000 | Wong et al. | |
| 6,133,323 A | 10/2000 | Hayek | |
| 6,180,099 B1 | 1/2001 | Paul | |
| 6,180,131 B1 | 1/2001 | Sunvold et al. | |
| 6,190,591 B1 | 2/2001 | van Lengerich | |
| 6,193,999 B1 | 2/2001 | Gennadios | |
| 6,204,291 B1 | 3/2001 | Sunvold et al. | |
| 6,235,320 B1 | 5/2001 | Daravingas et al. | |
| 6,248,390 B1 | 6/2001 | Stillman | |
| 6,261,589 B1 | 7/2001 | Pearson et al. | |
| 6,265,450 B1 | 7/2001 | Asami et al. | |
| 6,296,892 B1 | 10/2001 | Elseviers et al. | |
| 6,313,558 B1 | 11/2001 | Abukawa et al. | |
| 6,328,967 B1 | 12/2001 | Rivera | |
| 6,355,274 B1 | 3/2002 | Dartey et al. | |
| 6,365,209 B1 | 4/2002 | Cherukuri | |
| 6,368,629 B1 | 4/2002 | Watanabe et al. | |
| 6,368,633 B1 | 4/2002 | Lou et al. | |
| 6,383,534 B1 * | 5/2002 | Dyrr et al. | 426/74 |
| 6,399,090 B1 | 6/2002 | Shehadeh | |
| 6,399,124 B1 | 6/2002 | Lesens et al. | |
| 6,403,657 B1 | 6/2002 | Hinz | |
| 6,410,061 B1 | 6/2002 | Morré et al. | |
| 6,410,521 B1 | 6/2002 | Mundy et al. | |
| 6,410,522 B1 | 6/2002 | Ruenberg | |
| 6,410,685 B1 | 6/2002 | Masuyama et al. | |
| 6,413,558 B1 * | 7/2002 | Weber et al. | 426/2 |
| 6,416,800 B1 | 7/2002 | Weber et al. | |
| 6,416,806 B1 | 7/2002 | Zhou | |
| 6,420,350 B1 | 7/2002 | Fleischner | |
| 6,436,453 B1 | 8/2002 | van Lengerich et al. | |
| 6,468,568 B1 | 10/2002 | Leusner et al. | |
| 6,500,463 B1 | 12/2002 | van Lengerich | |
| 6,531,156 B1 | 3/2003 | Clark et al. | |
| 6,544,568 B1 | 4/2003 | La Droitte et al. | |
| 6,558,718 B1 | 5/2003 | Borek et al. | |
| 6,620,445 B1 | 9/2003 | Knueven | |
| 6,723,358 B1 | 4/2004 | van Lengerich | |
| 6,758,715 B1 | 7/2004 | Banks | |

OTHER PUBLICATIONS

Hidehisa Takahashi et al., "Effect of Liquid Diets With or Without Partially Hydrolyzed Guar Gum on Intestinal Microbial Flora and Function of Rats," Nutrition Research, vol. 15, No. 4, pp. 527–536, 1995 (abstract).

Hidehisa Takahashi et al., "Influence of intact and partially hydrolyzed guar gum on iron utilization in rats fed on iron-deficient diets,", Comp. Biochem. Physiol. vol. 109A, No. 1, pp. 75–82, 1994 (abstract).

Hidehisa Takahashi et al., "Influence of Partially Hydrolyzed Guar Gum on Constipation in Women," J. Nutr. Sc. Vitamental. 40, pp. 251–259, 1994 (abstract).

A. Golay et al., "The effect of a liquid supplement containing guar gum and fructose on glucose tolerance in non–insulin–dependent diabetic patients," NMCD Nutrition, Metabolism and Cardiovascular Diseases, vol. 5, No. 2, Jun. 1995, pp. 141–147 (abstract).

Hiroshi Hara et al., "Increases in calcium absorption with ingestion of soluble dietary fibre, guar–gum hydrolysate, depend on the casecum in partially nephrectomized and normal rats," British Journal of Nutrition (1996), 76, pp. 773–784 (abstract).

Brochures by Imperial Sensus LLC, "Product Data Sheets," "Facts about Inulin/FOS," "Frutafit Nutritional Information," "What is Frutafit.".

Joanne Slavin, "Commercially Available Enteral Formulas with Fiber and Bowel Function Measures," Nutrition in Clinical Practice 5:247–250, Dec. 1990.

Y. Ueda et al., "Effects of Indigestible Dextrin on Blood Glucose and Insulin Levels after Various Sugar Loads in Rats," J.Jpn. Soc. Nutr. Food Sci. 1993 (46) 131–137 (abstract, Fig. 1 and Tables1–4).

John E. Greenleaf, "Problem: thirst, drinking behavior, and involuntary dehydration," Medicine and Science In Sports and Exercise, vol. 24, No. 6, pp. 645–656, 1992.

Elsworth R. Buskirk et al., eds., "Body Fluid Balance," CRC Press, 1966, pp. 1–17.

Kazuhiro Ohkuma et al., "Pyrolysis of Starch and Its Digestibility by Enzymes—Characterization of Indigestibility Dextrin—," Matsutani Chemical Resarch Laboratories, Denpun Kagaku, 1990 (37) 107–114 (abstract, Figs. 1–7, Tables 1–5).

Brochure by Matsutani Chemical Industry. "Fibersol–2–Physiological Attributes," Feb. 16, 1999.

Brochure by Matsutani America, Inc., "Matsutani's Products and Their Functionalities," May 1999.

Y. Kishimoto et al., "Hypocholesterolemic Effect of Sodium Propionate," J. Nutri. Sci. Vitaminol. vol. 41, No. 1, 1995, pp. 77, 78.

Novartis Nutritional Corporation, "Benefiber Nutritional Data," Mar. 1999.

Novartis Nutritional Corporation, Novartis Nutrition Foodservice Products, Jan. 31, 2000.

Brochure by Matsutani Chemical Industry Co., Ltd., "Fibersol 2.".

Pamphlet by Imperial Sensus, LLC, "Insulin, A Natural Non–Digestible Carbohydrate Having Healthy Influences For Preventing Disease—Occurrence, History, Preparation, Safety, Physiology and Related Health Implications," Vesion 23–Oct. 29, 1999, 1997, 1998, 1999.

Elsworth R. Buskirk et al. "Fluid Balances" CRC Press.

Novartis Nutrition Corporation Benefit Nutritional Data.

Novartis Nutrition Corporation "Novartis Products".

Matsutani Chemical Industry Company, Ltd. "Fibersol 2".

Imperial Sensus, LLC "Inulin: A Natural Non–Digestible Carbohydrate Having Healthy Influences For Preventing Disease Occurance, History, Preparation, Safetly, Physiology and Related Health Implication" Versions 23–10.29.99, 1997, 1998, 1999.

Takashi, et al. "Hypolipidenic Effects of Guar Gum and its Enzyme Hydrolsate in Rats Fed Highly saturated Fat Diets" 1991 S. Karger Ag. Basel.

M. Kamen et al. "Reduction in Diarrhea Incidence by Soluble Fiber in Patients Receiving Total or Supplemental Entrtal Nutrition" Dept. of Surgery University, Germany Jun. 20, 1964.

Gary A. Weaver et al. "Dietary Guar Gum Alters Colonic Microbial Fermentation in Azoxymethane–Treated Rats" American Institute of Nutrition, Apr. 1, 1996, pp. 1979.

Hidehisa Takahashi et al. "Effect of Partially Hydrolyzed Guar Gum on Fecal Output in Human Volunteers" Nutritional Research, vol. 13, pp. 649., 1983.

A. Golay et al. "The Effect of a Liquid Supplement Containing Guar Gum and Fructose on Glucose Tolerance In–Non–Insulin–Dependent Diabetic Patients" Nutr–Metab cardiovascular Disease, 1995, pp. 141.

Hidehisa Takahashi et al. "Effect of Liquid Diets with of without Partially Hydrolyzed Guar Gum on Intestinal Microbial Flora and Function of Rats" Nutrition Research, vol. 15, No. 4.

Hidehisa Takahashi et al. "Influence of Intact Partially Hydrolysed Guar Gum on Iron Utilization in Rats Fed on Iron–Deficient Diets" Comp, BioChem, Physical, vol. 109A; pp. 75.

Hidehisa Takahashi et al. "Influence of Partially Hydrolyzed Guar Gum on Constipation in Women" Vitamental, vol. 40, pp. 251.

A. Golay, et al. "The Effect of a Liquid Supplement Containing Guar Gum and Fructose on Glucose tolerance in Non–Insulin–Dependent Diabelic Patients" NMCD Nutrition, Meabolism and Cardiovascular Diseases, vol. 5, Jun. 1995.

Hiroshi Hara, et al. "Increases in Calcium Absorption with Ingestion of Soluble Dietary Fiber, Guar Gum Hydrolysate, Depend on the Casecum in Partially Nephrectomized and Normal Rats" British Journal of Nutrition, 1996, pp. 773.

Brochures By Imperial Sensus LLC, Facts About Inulin/FOS,"Frutafit Nutritional Information,""What is Futafit".

Joanne Slavin "Commerically Available Enteral Formula with Fiber and Bowel Function Measures" Nutrition in Clinical Practice vol. 5, pp. 247–250, Dec. 1990.

Y. Ueda et al. "Effects of Ingestible Dextrin on Blood Glucose and Insulin Levels After Various Sugar Loads In Rats" Japan Nutritional Food Science 1993 pp. 49.

John E. Greenleaf "Problem: Thrist. Drinking Behavior, and Involuntary Dehydration" Medicine and Science In Sports and Exercise pp. 645–656.

Productscan Online, Worldwide Beverage Industry in which products are marketed as containing Fiber, Mar. 1, 2003, items 1–137, pp. 1–142.

Productscan Online, Asian Beverage Industry in which products are marketed as fruit flavored drinks, Dec. 3, 2002, items 1–154, pp. 1–121.

Productscan Online, German Beverage Industry in which products are marketed as fruit flavored drinks, May 13, 2002, items 1–127, pp. 1–107.

Flavor Encapsulation: A Convergence of Science and Art, Food Technology, Jul. 2004, vol. 58, No. 7.

Novel Encapsulation System Provides Controlled Release of Ingredients, Nov. 2003, vol. 57, No. 11.

Goldschlager Article from http://www.cockeyed.com/inside/goldschlager/goldschlager.html.

Orbitz Article from http://www.bevnet.com/reviews/orbitz.

Circular, Buckton Scott Group entitled "BetaCote 20VB," 1 page.

"Beverage Viscosity, Any Way You Like It!," Suanne J. Klahorst, 7 pages.

* cited by examiner

NUTRITIONALLY FORTIFIED LIQUID COMPOSITION WITH ADDED VALUE DELIVERY SYSTEMS/ELEMENTS/ADDITIVES

The present application is a continuation-in-part application of, and claims priority from PCT/US01/09171 designating the United States and filed on Mar. 21, 2001 which claimed priority from U.S. application Ser. No. 60/192,242, and of U.S. Ser. No. 10/204,572, filed Aug. 21, 2002 which was a continuation of, and claims priority from, PCT/US01/05630 filed Feb. 22, 2001, which in turn claims priority from U.S. Ser. No. 09/510,400, filed Feb. 22, 2000 and issued Jun. 19, 2001 as U.S. Pat. No. 6,248,390.

Cross-reference is made to co-pending, commonly owned U.S. application Ser. No. 09/963,209, filed on Sep. 26, 2001.

In modern society, regardless of age, people are obliged to live with a multiplicity of various injurious, and stressful, conditions that affect the body. Moreover, as we extend "life span" there is a remarkable, and rapid, increase in the population of the elderly (seniors) living under these circumstances, and further there exists a high incidence of acute, and/or chronic, diseases therefore providing an increasing need for addressing health desires and challenges, ameliorating and/or preventing disease, and/or maintaining and promoting health, and establishing well being and wellness.

Upon being diagnosed with any life-threatening disease, a prescribed method of treatment is the first step on the road to recovery. Optimistically, new health trends show American patients are becoming more interested in non-traditional treatments. Additionally, populations are becoming more preventative, health orientated, educated, and increasingly directed towards improving their quality of life as well as longevity. Also, and fast forwarding, seeking more and more "the means" by which they can insure longer lasting good health for themselves and their families. Animals too!

It is therefore the goal of the inventor, with all the aforesaid in mind, taken to heart, and being a focus, while noticing with keen observance, that there must be new delivery systems by which to deliver active ingredients that is acceptable, desirable, and foremost ethical for which to deliver target specific, and target general, substances that will offer the greatest return on investment . . . an investment in health.

Problematic today is the inconsistency of the consumer to adhere to a routine, except perhaps, when it comes to pharmaceuticals, which are basically for pain relief and address illness, be it healing from an infection and/or disease. Succinctly put, commercially available vitamin and mineral supplements are convenient and useful in many circumstances where improved nutrient uptake is desirable. However, adhering to a daily routine of nutritional supplementation has had limited success. For example, daily supplementation requires a change in normal habits and practices of the user.

Further, some individuals find that supplements provide no immediate physiological signal to help them perceive a benefit, or to establish a consistent routine of use. A number of other pharmacological agents taken for health are typically associated with a, or more than one, noticeable bodily or physiological response(s). We have, unfortunately, become far too much of a society whereby you have to "feel it to believe it." It is believed that the lack of a physiological signal from the vast majority of nutritional supplements is responsible for limiting the overall acceptability of them, which is unfortunate since there is a need for supplementation to augment the daily intake of vitamins and minerals found in foods.

At least the inventor found no resistance in getting a consumer to have at least one bottle of water a day, sometimes more. (Maybe not all drunk at once, but at least a bottle a day). The water with fiber enrichment, invention Fiber-water (U.S. Pat. No. 6,248,390 to the same inventor), elicited the same response as plain water as it taste just like water.

Building on that, therefore it is the intention of the inventor to present new and novel additions to the invention Fiber-water by taking it to the next level, so as to address all the aforesaid through safe, pure, fresh fiber enriched water while maintaining basically the taste of water.

While the term "Functional Foods" has become more commonplace, for many a better definition is necessary ergo the term "Functional Foods", meaning foods containing functional ingredients with documented beneficial health effects, consumed as part of the daily diet.

Additionally of noteworthiness is an American study on consumer behavior confirming that there has been a change in how customers relate to health and well-being. Previously good health meant, "taking the bad out," for example by reducing the salt or fat content in food. Today we are seeing a shift in the word "health" in connection with food, meaning, "putting the good in". That was the goal of Fiber-water and now extending the novelty of that invention by adding one or more additional benefits in one or more categories of supplementation including but not limited to, pharmaceuticals, nutraceuticals, dietary supplements, etc. It is even more critical as noted by the inventor if we take a careful and critical look at the quality of food produced today, (from soils depleted in nutrients), protracted storage time in warehouses, and extended shelf life in the consumer marketplace.

Happy to report that surveys are showing that a large, and continuously increasing, number of consumers are now taking more responsibility for their own health. The inventor predicts, and shall participate in, what she envisions is the future scenario . . . consumers who will focus on "nutrition management" involving personally formulated diets, with the results that the boundaries between medicine and nutrition will become blurred. In order to accomplish the aforesaid new technologies and methodologies will have to be employed. These include but are not limited to the delivery of ingredients, the manufacturing technologies, but the methods by which business is conducted so that companies, regardless of their size, will produce "quality" while operating profitably. Business models, methods and opportunities are fully covered in the inventor's CIP of PCT/US01/09171 titled: Method of Hydration; infusion Packet System(s), Support Member(s) Delivery System(s), and Method(s); with Business Model(s) and Method(s).

At the time of this writing the inventor is noticing an ever-growing trend amongst adults who are becoming more aware and specifically desirous of using beverages (nutritional drinking) to help maintain their health. Further, parents and caregivers are becoming increasingly aware (and with awareness comes responsibility) of what they are giving to the younger generation. Not only are they providing products "in the now" but also hopefully teaching these impressionable minds how to make sound healthy choices as they mature. This inventor takes great pains, and is dedicated to providing to the beverage companies first, the systems by which to deliver, and additionally suggestions and formulations of what to deliver. Further the inventor is a major supporter of those who wish to improve their health, those with healthier goals, those with health challenges, be they infants, children, teenagers, the aging population (seniors), regardless, and even their pets.

There is one universal solvent, the one element that everyone needs everyday to live, and that is water. Water provides hydration, for without water one cannot live. So water, to this invention, in the simplistic of terms, becomes the essential delivery system. Fiber is necessary to live healthier and now on to the additional new and novel.

Building on this the invention Fiber-Water (to this inventor, Stillman, U.S. Pat. No. 6,248,390 and now adding additional systems into the Fiber-Water (or even into plain pure water) which delivers fiber within one or more of the new and novel delivery systems, not just the formulations, by which to deliver the aforesaid. It is not far different than looking at society's advancement in communication technologies such the inventions of the telephone, (now wireless cell phones), walkie-talkies, fax machines, internet, etc. New pathways of delivery in beverage delivery must advance if we ate to deliver the myriad of new discoveries in substances that will not just address life span but health span as well.

FIELD OF THE INVENTION

One of the main goals, call it the beauty if you will, of Fiber-Water . . . water containing soluble fiber (U.S. Pat. No. 6,248,390) is the fact that it "taste just like water" yet delivers a significant amount of soluble fiber, while simultaneously providing pure fresh necessary water to live (hydration) for humans and/or animals.

The next generation of fiber-waters is new and novel due to the fact that, while the fiber in water composition still presents a significant amount of soluble fiber, ergo contributing significantly to daily hydration needs (pure fresh water, still or sparkling), it further incorporates one or more systems designed to deliver one at more additional health promoting/addressing ingredients/components, while ensuring their stability, their bio-availability, controlling their release (if deemed desirable and/or appropriate), including but not limited to the groups titled: pharmaceuticals, nutraceuticals, dietary supplements, enzymes, amino-acids, diagnostics, pre-biotics, pro-biotics, anti-inflamatories, anti-bacterials, herbal extracts, aroma(s), flavor, color, etc.

By this new invention it is the goal of the inventor to still present a product, following all the guidelines of fiber-water as its basis, but to continue beyond fiber-water with the aforesaid being innovational, while keeping the general taste of water and/or a water composition that tastes just like, and/or near to water.

It is to be noticed here, described in detail later, that waters have different tastes due to their Total Dissolved Solids and/or Total Dissolved Salts. Additionally some mineral waters are, by nature, naturally sparkling. It is here conceived that they be without gas, with natural gas, or the addition to gas in total or in part. (Further if minerals (organic and/or inorganic) are added then the TDS (total dissolved solids and/or salts may vary with the varying viscosities as we shall discover later.

BACKGROUND OF THE INVENTION

In keeping current with modern trends, consumer's preferences, and/or the like the inventor has noticed all the flavored waters, enriched waters, and the like. It is irrelevant as to the inventor's personal feeling on the value to the consumer of these new products, but is focused on inventing beyond fiber-water, ethically and scientifically sound product(s), and these may be referred to by some as line extension of fiber-water: Fiber-Water with the added value delivery systems/elements/additives addressing specific, and/or special dietary use(s), and/or medical use(s) for humans and animals.

The inventor calls first attention to the fact that while many still enjoy the refreshing taste of pure spring and/or purified water, others are desirous of water with a dash of flavor. Still others wish that they had further supplementation/nutrition, beyond water, but are desirous of having the "taste just like water" taste. At most, lightly flavored water, even colored, yet can remain transparent/clear (except if designed to be colorful and cloudy for effect), following the guidelines set forth by the FDA of the United States and the equivalent jurisdiction in other countries.

Certainly companies have added excitement to the water category by adding ingredients such as flavors, sweeteners, etc. As an example of flavored waters Hydrator™, a new line of lightly flavored still waters from Aqua Vie Beverage Corp., Ketchum, Id., includes varieties such as Avalanche (pear, guava and other flavors), Bamboo (Japanese cherry), Harvest (French strawberry), McIntosh (McIntosh apple), Paradise (orange, peach), Java (kona coffee), Sun Tea (tea, lemon and other flavors).

Past just the flavors, new water-like beverages are rapidly appearing in the marketplace. After years of research, limited before filing for Fiberwater, and post issuance of U.S. Pat. No. 6,248,390 to the inventor, Stillman here, and World Intellectual Property Organization (PCT WO 01/62108 A1), the inventor has come to realize that there's a growing segment of enriched/enhanced water-like drinks. The functional beverage trends are spilling over into the water subcategory.

In Japan they are called "Near Water", as meaning close to water. As an example, Nice One drink from Asahi contains vitamins $B_1$ and C, reishi, seaweed extract and chamomile as just an example. Although the trend started in Japan, it is apparent that these beverages are becoming more popular in the United States, Europe and beyond.

Now many are beginning to believe that we can get Americans to drink more water by making available these more mainstream enhanced waters, offering healthy additives such as vitamins, minerals, herbs and/or the like. However this inventor feels, that as with anything else, responsibility must be taken by the producing companies and the consumers as well.

The inventor calls attention to the following news release:

Jul. 1, 2002 American Institute for Cancer Research, Healthy Drinks by Karen Collins, M.S., R.D., C.D.N. American Institute for Cancer Research Choosing a drink has never been so complicated. "New age" waters, teas and juices—with added vitamins, herbs, or other "healthy" ingredients—are now a billion-dollar business. Although some of these new beverages may be simply a flavorful way to increase consumption of liquids, others may not be appropriate for everyone. Some added ingredients might cause health problems, while others are in amounts so small they may have a negligible effect.

Many of these new beverages are simply water or tea with added flavorings like fruit essence, lemongrass, or ginger. They are promoted on the premise that most Americans don't drink enough water, and that people will drink more of flavored drinks than plain water. Studies suggest that this may often be true. If a flavored water or tea helps you drink more, it could be a great choice.

Before selecting any of these drinks, consider whether you want them to add or limit your calorie intake. If you're trying to control your weight, an extra 250 to 375 calories may be counter-productive. On the other hand, people who don't need to lose weight might benefit from extra calories shortly before, during, or after high-energy exercise.

Some drinks are fortified with vitamins or minerals. For example, juices with added calcium may help people who don't or can't consume dairy products and would benefit from this fortification. On the other hand, B vitamins don't need to be added to a drink since most of us consume adequate amounts. Added vitamins or minerals can help make up for what is lacking in some people's diets, but for those who meet recommended amounts through diet or supplements, significant additions to drinks may be useless or even harmful.

Many drinks contain herbals—like echinacea, guarana, ginkgo biloba, or kava—that supposedly help energize, calm, or promote well-being in other ways. But the effectiveness of many of these herbs is either questionable or still under study. For example, echinacea is currently thought to help the immune system fight some illnesses in the short term, but continued long-term use is believed to actually depress the immune system.

In some cases, herbal ingredients that seem likely to have possible health benefits are added in amounts too small to have any real effect. Drinks containing St. John's Wort usually provide 250 milligrams (mg) per 20-ounce bottle, but studies show that 900 to 1,500 mg a day are needed to create mood enhancing effects. The low levels found in most drinks might reduce the chance of consuming too much of this herb, but it also means consumers are paying extra for something they aren't getting in any significant amount.

People assume that any new drink on the market must be safe. But some added ingredients, if present in significant amounts, might pose health dangers for certain people. Warnings have recently been issued about kava as a possible cause of liver damage. Kava should be avoided by anyone who drinks alcohol daily or takes medicines that could affect the liver. St. John's Wort and ginkgo biloba can interact with medications. Guarana and some kinds of ginseng can raise blood pressure.

Don't be misled by new marketing ploys. Before buying a pricey "health" beverage, check what and how much added ingredients it contains, and how it relates to your needs.

AICR is the only major cancer charity focusing exclusively on the link between diet, nutrition and cancer. The Institute provides education programs that help millions of Americans learn to make changes for lower cancer risk.

PepsiCo launched a purified water called Aquafina, and will break soon with a line of fruit-flavored, vitamin-mineral enhanced waters called Aquafina Essentials. Coca-Cola, Atlanta, decided to produce a bottled water with added minerals, Dasani, and now they too will be launching Desani Nutri-waters adding additional nutritive value to their existing mineral fortified water.

Aquafina rang up $214 million in sales last year, while Dasani brought in $168 million, according to Information Resources, while sales of carbonated beverages, such as soda, have dropped about 4 percent in the last five years, sales of bottled water have more than tripled, as people have become more health conscious and, simultaneously, leery of the quality of tap water.

With soda sales slipping, and energy drinks losing their buzz among consumers, beverage companies are hoping these enhanced waters can build on the success of bottled water, providing consumers something new that will have an effect on their body, and/or won't make them feel guilty.

The first such products out on supermarket shelves in the last years were Energy Brand's VitaminWater, Veryfine's Fruit20, and Propel™ by Quaker Oats, now a part of PepsiCo's Gatorade brand that is a so-called a "fitness water", with vitamins B and C in flavors such as black cherry and/orange.

In coming months, in addition to PepsiCo Inc., Coca Cola Inc. much of the rest of the beverage industry will be jumping in including Snapple Beverage Group Inc. with its Elements fruit-flavored waters, and health products maker Baxter International Inc. with Pulse, a fruity water supplement designed to ward off prostate trouble in men and ease menopause in women.

Other companies will roll out a barrage of lightly sweetened "waters" laced with fruit flavors, vitamins, herbs and even ingredients used to treat specific medical conditions. In coming months, more and more products are coming to market with all sorts of twists, ergo it is firmly apparent that the nation's largest beverage makers are about to launch an all-out campaign to change the definition of water. With bottled water a $6 billion a year business it is possible that this so-called potential sub-category can be extremely profitable.

The belief is that this so called sub-category is blossoming quickly and will be booming by year 2003 forward. If the sales of the Japanese Near Waters are an indication then this is correct. In fact some editorials claim that the distribution between natural spring waters and the flavored/functional variety are approaching a split down the middle potential.

The inventor has noticed that there are other enriched waters on the market that containing recognizable ingredients such as caffeine, nicotine, oxygen, and/or the like. They sell not necessarily based on hydration, even though that might be a part of it, but on the "effect" that the additional ingredient is supposed to illicit for the user.

The inventor has also noticed that noticed that most enhanced waters, with 10 to 40 calories per 8-ounce serving, are still lower in calories than juice or soda, but some have as many as 80 calories per serving, bringing the total calorie count to 160 for the average 16-ounce container. By contrast, non-diet colas have about 215 calories per 16-ounce servings and/orange juice has about 225 calories.

It also seems to the inventor that the higher-calorie waters are "starting to be more like a juice drink" at best, and at worst just flavored sugar water for which the inventor is opposed.

When you start adding one or more additional ingredients, especially needed to mask undesirable taste, the inventor has many mixed feelings. Amongst the major concerns, the just said may greatly increase the caloric count and/or, just as negative, use chemicals, must be taken into consideration while additionally noting that the efficacy equation most likely gets muddled. While there are benefits to offering healthy additives, caution, and certainly responsibility, should be taken by both the companies and the consumers.

The inventor feels that flavored water, because it is a clear product just like water, is more closely linked to water's heritage. Flavored waters are just a way to add variety and keep people from getting bored with plain water. Then to you can color water and governed by association have no flavor in the water at all but the color fools the perception.

As more people live lives on the go, we are seeing a tremendous increase in sales of bottled water due to the fact that users are deciding to carry bottles with them. (Bottled water sales, U.S. only, are about $6 billion annually) Other packaging is becoming more and more noteworthy.

Beyond the just flavored waters are the enriched waters and with the enriched waters it is the inventor's concern relative to such additional additives. While the general idea is to have another alternative that consumers still see as healthy (Propel is focused on fitness-conscious customers, while Snapple appears to be targeting its Elements at the energy drink set with vibrant colors and exotic ingredients such as ginseng, guarana, bee pollen and gingko biloba, as well as more traditional health enhancers like beta carotene), the inventor, by this invention, wants to use innovative methodologies/technologies, into water, to assure her position.

SUMMARY OF THE INVENTION

There is an Old Expression that Says, "You Can't Have Your Cake and Eat it Too" . . .

In the aforementioned fiber-water patent, issued (U.S. Pat. No. 6,248,390) and pending international (PCT WO 01/62108 A1), the inventor presented the antithesis of that expression: an invention composed specifically of water and soluble fiber (that's simple enough) that is tasteless, odorless and colorless, much like water itself.

Into the invention called fiber-water, the inventor has added one, or more than one, additional elements, be they complimentary, aesthetic, and/or desired, and/or functional when it comes to ingredients in a healthy palatable form and, that will not only contribute to hydration requirements, fulfill a portion of ones daily need of fiber, but do so, with practically the same caloric intake and/or an additional minimal caloric intake as a glass of the invention, fiber-water, with the addition of encapsulations (a carrier for additives) and/or viscosity changes, (a carrier for additives) and/or by unique technologies whereby the water is changed/processed in such a way as to enhance its ability to be taken up by the cells of the body of humans (and/or animals), prevent the growth of organisms, promote health, and/or medical benefits and/or the like by the priority techniques of processing the water solely and/or along with the delivery system(s) used.

As an example,
  a. Penta™ water (San Diego Calif.) claims to be able to micro-cluster water so as to be taken up more rapidly by the cells.
  b. U.S. Pat. No. 5,824,353 to Tsunoda et al. (Taisho Pharmaceutical Co., Ltd. Tokyo JP), issued Oct. 20, 1998, titled Mineral water abstracts;
    i. The present invention relates to small-cluster water whose cluster (water molecule groups or hydrates) is small on the average and is retained as it is stably for a very long period of time. Water usually forms clusters (groups of molecules) consisting of a large number of molecules by hydrogen bonds, and the clusters always vary in size, depending on various conditions of a place where the water is present.
    ii. Water whose cluster is small on the average is known to be very useful physiologically and medically as follows: it tastes good because it completely gets into the taste buds (taste cells) of tongue owing to vigorous molecular motion; it gets into cells easily to activate them; it accelerates the absorption of a drug or food and drink because of its rapid absorption through a digestive tract; and it has cancer-preventive effect because it reduces the production of mutagens from the contents of intestines by controlling or activating enteric microorganisms and digestive tract tissue cells.
  c. U.S. Pat. No. 5,904,851 to Taylor et al. (Life international Products Inc. Naples Fla.), issued May 18, 1999, titled: Oxygenating apparatus, method for oxygenating liquid therewith, and applications thereof teaches that suitable therapeutic processes in which liquids made in accordance with the present invention can be advantageously employed to include, for example, increasing the oxygen content of blood and tissues.

The main 3 systems that will be used include encapsulations, viscosity changes, and/or what the inventor commonly refers to as the "lava lamp" type containments using water and oil principles relating technologies (emulsions, suspensions, and/or solutions, etc.)

It is also noted, and fully respected, are the guidelines set forth by the (American) Food and Drug Association (FDA) and the equivalents in other countries as related to production of drinkable products safely and in accordance, with or without the need for refrigeration.

During the research and development of fiber-water for commercialization many procedural options were tried and/or considered. In fact at the time of this writing the formal/final production methodology has not been solidified. The inventor here makes full disclosure that while the goal is to produce product at a neutral Ph, production technologies are not fully developed to be able to do so under existing governmental regulations.

To that end not just the use of thermal processing technologies may be needed to be employed, but the use of organic and/or inorganic acidulates and/or the like maybe needed to prevent organism contamination and growth as well. Further ingredients, and maybe even those considered as part of the sweetener family may be needed to counteract the taste of acid necessary to reduce potential contamination. If a sweetener is used in the production of fiber-water it is solely used for the ability to counteract the acid so as to present a product that tastes like water and not "acid water". The same holds true for this invention.

It is also noted that with the additions, encapsulation(s) and/or changing viscosities, in total and/or in part it might be desirous, and/or necessary to add one, or a combination of minerals, (organic and/or inorganic) to be used for specific reasons and/or conditions, which may or may not bring the TDS above 500. Note: With a product that has more than one viscosity change, which may stay in suspension or move around (like the "lava lamp" conceptualization) there may be assigned to each viscosity change a different TDS.

Much of the innovativeness of this invention is primarily based on the first system, encapsulations; regardless of size, structure, compositions, content(s), and/or the like to bring forth all the valuable components that come with the use of the aforesaid. (The varying viscosity mediums may or may not include encapsulations) It is further with the understanding that flavoring can be added, along with aroma, and colorants.

To understand the market positioning of this sort of product, with its many variations, the inventor calls forth the need to understand governmental regulations:

Definitions of Regulations as Set Forth by Our Government:

The term "Dietary Supplement" which is described in the Dietary Supplement Health and Education Act of 1994 (DSHEA)

In 1994 Congress passed legislation known as the Dietary Supplement Health and Education Act (DSHEA). The law restricted the Food and Drug Administration (FDA) in the regulations it could enforce limiting label claims on dietary supplements. Specifically, DSHEA allows dietary supplement labels to carry statements dealing with structure/function claims such as "supports the immune system." Section 6 of DSHEA states that structure/function statements are "statements of nutritional support . . . that describe the role of a nutrient or dietary ingredient intended to affect the structure or function in humans."

The intent of DSHEA was to provide consumers access to more health-related information about dietary supplements. However, sifting through the complicated language contained in the legislation is a formidable task. The fine line in semantics with respect to a supplement "supporting" a normal body function as opposed to "treating a disease" remains as controversial an area as the current debate over how the FDA actually defines "diseases."

Incorporated herein is the entire DSHEA for ease of reference and for the ability to logically look at the reference while reviewing the filing.

'Dietary Supplement Health and Education Act of 1994'.

An Act

To amend the Federal Food, Drug, and Cosmetic Act to establish standards with respect to dietary supplements, and for other purposes.

Be it enacted by the Senate and House of Representatives of the United States of America in Congress assembled,

SECTION 1. SHORT TITLE; REFERENCE; TABLE OF CONTENTS.

(a) SHORT TITLE—This Act may be cited as the 'Dietary Supplement Health and Education Act of 1994'.

(b) REFERENCE—Whenever in this Act an amendment or repeal is expressed in terms of an amendment to, or repeal of, a section or other provision, the reference shall be considered to be made to a section or other provision of the Federal Food, Drug, and Cosmetic Act.

(c) TABLE OF CONTENTS—The table of contents of this Act is as follows:

Sec. 1. Short title; reference; table of contents.
Sec. 2. Findings.
Sec. 3. Definitions.
Sec. 4. Safety of dietary supplements and burden of proof on FDA.
Sec. 5. Dietary supplement claims.
Sec. 6. Statements of nutritional support.
Sec. 7. Dietary supplement ingredient labeling and nutrition information labeling.
Sec. 8. New dietary ingredients.
Sec. 9. Good manufacturing practices.
Sec. 10. Conforming amendments.
Sec. 11. Withdrawal of the regulations and notice.
Sec. 12. Commission on dietary supplement labels.
Sec. 13. Office of dietary supplements.
SEC. 2. FINDINGS.

Congress finds that (1) improving the health status of United States citizens ranks at the top of the national priorities of the Federal Government;

(2) the importance of nutrition and the benefits of dietary supplements to health promotion and disease prevention have been documented increasingly in scientific studies;

(3)
(A) there is a link between the ingestion of certain nutrients or dietary supplements and the prevention of chronic diseases such as cancer, heart disease, and osteoporosis; and (B) clinical research has shown that several chronic diseases can be prevented simply with a healthful diet, such as a diet that is low in fat, saturated fat, cholesterol, and sodium, with a high proportion of plant-based foods;

(4) healthful diets may mitigate the need for expensive medical procedures, such as coronary bypass surgery or angioplasty;

(5) preventive health measures, including education, good nutrition, and appropriate use of safe nutritional supplements will limit the incidence of chronic diseases, and reduce long-term health care expenditures;

(6)
(A) promotion of good health and healthy lifestyles improves and extends lives while reducing health care expenditures; and (B) reduction in health care expenditures is of paramount importance to the future of the country and the economic well-being of the country;

(7) there is a growing need for emphasis on the dissemination of information linking nutrition and long-term good health;

(8) consumers should be empowered to make choices about preventive health care programs based on data from scientific studies of health benefits related to particular dietary supplements;

(9) national surveys have revealed that almost 50 percent of the 260,000,000 Americans regularly consume dietary supplements of vitamins, minerals, or herbs as a means of improving their nutrition;

(10) studies indicate that consumers are placing increased reliance on the use of nontraditional health care providers to avoid the excessive costs of traditional medical services and to obtain more holistic consideration of their needs;

(11) the United States will spend over $1,000,000,000,000 on health care in 1994, which is about 12 percent of the Gross National Product of the United States, and this amount and percentage will continue to increase unless significant efforts are undertaken to reverse the increase;

(12)
(A) the nutritional supplement industry is an integral part of the economy of the United States;

(B) the industry consistently projects a positive trade balance; and (C) the estimated 600 dietary supplement manufacturers in the United States produce approximately 4,000 products, with total annual sales of such products alone reaching at least $4,000,000,000;

(13) although the Federal Government should take swift action against products that are unsafe or adulterated, the Federal Government should not take any actions to impose unreasonable regulatory barriers limiting or slowing the flow of safe products and accurate information to consumers;

(14) dietary supplements are safe within a broad range of intake, and safety problems with the supplements are relatively rare; and

(15)
(A) legislative action that protects the right of access of consumers to safe dietary supplements is necessary in order to promote wellness; and (B) a rational Federal framework must be established to supersede the current ad hoc, patchwork regulatory policy on dietary supplements.

SEC. 3. DEFINITIONS.

(a) DEFINITION OF CERTAIN FOODS AS DIETARY SUPPLEMENTS—Section 201 (21 U.S.C. 321) is amended by adding at the end the following:

(ff) The term dietary supplement'
(1) means a product (other than tobacco) intended to supplement the diet that bears or contains one or more of the following dietary ingredients:
  (A) a vitamin;
  (B) a mineral;
  (C) an herb or other botanical;
  (D) an amino acid;
  (E) a dietary substance for use by man to supplement the diet by increasing the total dietary intake; or
  (F) a concentrate, metabolite, constituent, extract, or combination of any ingredient described in clause (A), (B), (C), (D), or (E);
(2) means a product that
  (A)
    (i) is intended for ingestion in a form described in section 411(c)(1)(B)(i); or
    (ii) complies with section 411(c)(1)(B)(ii);
  (B) is not represented for use as a conventional food or as a sole item of a meal or the diet; and
  (C) is labeled as a dietary supplement; and
(3) does
  (A) include an article that is approved as a new drug under section 505, certified as an antibiotic under section 507, or licensed as a biologic under section 351 of the Public Health Service Act (42 U.S.C. 262) and was, prior to such approval, certification, or license, marketed as a dietary supplement or as a food unless the Secretary has issued a regulation, after notice and comment, finding that the article, when used as or in a dietary supplement under the conditions of use and dosages set forth in the labeling for such dietary supplement, is unlawful under section 402(f); and
  (B) not include
    (i) an article that is approved as a new drug under section 505, certified as an antibiotic under section 507, or licensed as a biologic under section 351 of the Public Health Service Act (42 U.S.C. 262), or
    (ii) an article authorized for investigation as a new drug, antibiotic, or biological for which substantial clinical investigations have been instituted and for which the existence of such investigations has been made public, which was not before such approval, certification, licensing, or authorization marketed as a dietary supplement or as a food unless the Secretary, in the Secretary's discretion, has issued a regulation, after notice and comment, finding that the article would be lawful under this Act.
Except for purposes of section 201(g), a dietary supplement shall be deemed to be a food within the meaning of this Act.'
(b) EXCLUSION FROM DEFINITION OF FOOD ADDITIVE—Section 201 (s) (21 U.S.C. 321(s)) is amended
  (1) by striking 'or' at the end of subparagraph (4);
  (2) by striking the period at the end of subparagraph (5) and inserting '; or'; and
  (3) by adding at the end the following new subparagraph:
    (6) an ingredient described in paragraph (ff) in, or intended for use in, a dietary supplement.'.
(c) FORM OF INGESTION—Section 411(c)(1)(B) (21 U.S.C. 350(c)(1)(B)) is amended
  (1) in clause (i), by inserting 'powder, softgel, gelcap,' after 'capsule,'; and
  (2) in clause (ii), by striking 'does not simulate and'.

SEC. 4. SAFETY OF DIETARY SUPPLEMENTS AND BURDEN OF PROOF ON FDA.

Section 402 (21 U.S.C. 342) is amended by adding at the end the following:
(f) (1) If it is a dietary supplement or contains a dietary ingredient that
  (A) presents a significant or unreasonable risk of illness or injury under
    (i) conditions of use recommended or suggested in labeling, or
    (ii) if no conditions of use are suggested or recommended in the labeling, under ordinary conditions of use;
  (B) is a new dietary ingredient for which there is inadequate information to provide reasonable assurance that such ingredient does not present a significant or unreasonable risk of illness or injury;
  (C) the Secretary declares to pose an imminent hazard to public health or safety, except that the authority to make such declaration shall not be delegated and the Secretary shall promptly after such a declaration initiate a proceeding in accordance with sections 554 and 556 of title 5, United States Code, to affirm or withdraw the declaration; or
  (D) is or contains a dietary ingredient that renders it adulterated under paragraph (a)(1) under the conditions of use recommended or suggested in the labeling of such dietary supplement.
  In any proceeding under this subparagraph, the United States shall bear the burden of proof on each element to show that a dietary supplement is adulterated. The court shall decide any issue under this paragraph on a de novo basis.
(2) Before the Secretary may report to a United States attorney a violation of paragraph (1)(A) for a civil proceeding, the person against whom such proceeding would be initiated shall be given appropriate notice and the opportunity to present views, orally and in writing, at least 10 days before such notice, with regard to such proceeding.'.

SEC. 5. DIETARY SUPPLEMENT CLAIMS.

Chapter IV (21 U.S.C. 341 et seq.) is amended by inserting after section 403A the following new section:

DIETARY SUPPLEMENT LABELING EXEMPTIONS

SEC. 403B. (a) IN GENERAL—A publication, including an article, a chapter in a book, or an official abstract of a peer-reviewed scientific publication that appears in an article and was prepared by the author or the editors of the publication, which is reprinted in its entirety, shall not be defined as labeling when used in connection with the sale of a dietary supplement to consumers when it
  (1) is not false or misleading;
  (2) does not promote a particular manufacturer or brand of a dietary supplement;
  (3) is displayed or presented, or is displayed or presented with other such items on the same subject matter, so as to present a balanced view of the available scientific information on a dietary supplement;
  (4) if displayed in an establishment, is physically separate from the dietary supplements; and
  (5) does not have appended to it any information by sticker or any other method.
(b) APPLICATION—Subsection (a) shall not apply to or restrict a retailer or wholesaler of dietary supplements in any way whatsoever in the sale of books or other publications as a part of the business of such retailer or wholesaler.

(c) BURDEN OF PROOF—In any proceeding brought under subsection (a), the burden of proof shall be on the United States to establish that an article or other such matter is false or misleading.'.

SEC. 6. STATEMENTS OF NUTRITIONAL SUPPORT.

Section 403(r) (21 U.S.C. 343(r)) is amended by adding at the end the following:

(6) For purposes of paragraph (r)(1)(B), a statement for a dietary supplement may be made if (A) the statement claims a benefit related to a classical nutrient deficiency disease and discloses the prevalence of such disease in the United States, describes the role of a nutrient or dietary ingredient intended to affect the structure or function in humans, characterizes the documented mechanism by which a nutrient or dietary ingredient acts to maintain such structure or function, or describes general well-being from consumption of a nutrient or dietary ingredient, (B) the manufacturer of the dietary supplement has substantiation that such statement is truthful and not misleading, and (C) the statement contains, prominently displayed and in boldface type, the following: 'This statement has not been evaluated by the Food and Drug Administration. This product is not intended to diagnose, treat, cure, or prevent any disease.'.

A statement under this subparagraph may not claim to diagnose, mitigate, treat, cure, or prevent a specific disease or class of diseases. If the manufacturer of a dietary supplement proposes to make a statement described in the first sentence of this subparagraph in the labeling of the dietary supplement, the manufacturer shall notify the Secretary no later than 30 days after the first marketing of the dietary supplement with such statement that such a statement is being made.'.

SEC. 7. DIETARY SUPPLEMENT INGREDIENT LABELING AND NUTRITION INFORMATION LABELING.

(a) MISBRANDED SUPPLEMENTS—Section 403 (21 U.S.C. 343) is amended by adding at the end the following:

(s) If (1) it is a dietary supplement; and (2) (A) the label or labeling of the supplement fails to list (i) the name of each ingredient of the supplement that is described in section 201 (ff); and (ii)

(I) the quantity of each such ingredient; or (II) with respect to a proprietary blend of such ingredients, the total quantity of all ingredients in the blend;

(B) the label or labeling of the dietary supplement fails to identify the product by using the term 'dietary supplement', which term may be modified with the name of such an ingredient;

(C) the supplement contains an ingredient described in section 201 (ff)(1)(C), and the label or labeling of the supplement fails to identify any part of the plant from which the ingredient is derived;

(D) the supplement (i) is covered by the specifications of an official compendium;

(ii) is represented as conforming to the specifications of an official compendium; and (iii) fails to so conform; or (E) the supplement (i) is not covered by the specifications of an official compendium; and (ii)

(I) fails to have the identity and strength that the supplement is represented to have; or (II) fails to meet the quality (including tablet or capsule disintegration), purity, or compositional specifications, based on validated assay or other appropriate methods, that the supplement is represented to meet.'.

(b) SUPPLEMENT LISTING ON NUTRITION LABELING—Section 403(q)(5)(F) (21 U.S.C. 343(q)(5)(F)) is amended to read as follows:

(F) A dietary supplement product (including a food to which section 411 applies) shall comply with the requirements of subparagraphs (1) and (2) in a manner which is appropriate for the product and which is specified in regulations of the Secretary which shall provide that (i) nutrition information shall first list those dietary ingredients that are present in the product in a significant amount and for which a recommendation for daily consumption has been established by the Secretary, except that a dietary ingredient shall not be required to be listed if it is not present in a significant amount, and shall list any other dietary ingredient present and identified as having no such recommendation;

(ii) the listing of dietary ingredients shall include the quantity of each such ingredient (or of a proprietary blend of such ingredients) per serving;

(iii) the listing of dietary ingredients may include the source of a dietary ingredient; and (iv) the nutrition information shall immediately precede the ingredient information required under subclause (i), except that no ingredient identified pursuant to subclause (i) shall be required to be identified a second time.'.

(c) PERCENTAGE LEVEL CLAIMS—Section 403(r)(2) (21 U.S.C. 343(r)(2)) is amended by adding after clause (E) the following:

(F) Sub-clause (i) clause (A) does not apply to a statement in the labeling of a dietary supplement that characterizes the percentage level of a dietary ingredient for which the Secretary has not established a reference daily intake, daily recommended value, or other recommendation for daily consumption.'.

(d) VITAMINS AND MINERALS—Section 411(b)(2) (21 U.S.C. 350(b)(2)) is amended (1) by striking 'vitamins or minerals' and inserting 'dietary supplement ingredients described in section 201(ff)';

(2) by striking '(2)(A)' and inserting '(2)'; and (3) by striking subparagraph (B).

(e) EFFECTIVE DATE—Dietary supplements (1) may be labeled after the date of the enactment of this Act in accordance with the amendments made by this section, and (2) shall be labeled after Dec. 31, 1996, in accordance with such amendments

SEC. 8. NEW DIETARY INGREDIENTS.

Chapter IV of the Federal Food, Drug, and Cosmetic Act is amended by adding at the end the following:

'NEW DIETARY INGREDIENTS

SEC. 413. (a) IN GENERAL—A dietary supplement which contains a new dietary ingredient shall be deemed adulterated under section 402(f) unless it meets one of the following requirements:

(1) The dietary supplement contains only dietary ingredients which have been present in the food supply as an article used for food in a form in which the food has not been chemically altered.

(2) There is a history of use or other evidence of safety establishing that the dietary ingredient when used under the conditions recommended or suggested in the labeling of the dietary supplement will reasonably be expected to be safe and, at least 75 days before being introduced or delivered for introduction into interstate commerce, the manufacturer or distributor of the dietary ingredient or dietary supplement provides the Secretary with information, including any citation to published articles, which is the basis on which the manufacturer or distributor has concluded that a dietary supplement containing such dietary ingredient will reasonably be expected to be safe.

The Secretary shall keep confidential any information provided under paragraph (2) for 90 days following its receipt. After the expiration of such 90 days, the Secretary shall place such information on public display, except matters in the information which are trade secrets or otherwise confidential, commercial information.

(b) PETITION—Any person may file with the Secretary a petition proposing the issuance of an order prescribing the conditions under which a new dietary ingredient under its intended conditions of use will reasonably be expected to be safe. The Secretary shall make a decision on such petition within 180 days of the date the petition is filed with the Secretary. For purposes of chapter 7 of title 5, United States Code, the decision of the Secretary shall be considered final agency action.

(c) DEFINITION—For purposes of this section, the term 'new dietary ingredient' means a dietary ingredient that was not marketed in the United States before Oct. 15, 1994 and does not include any dietary ingredient which was marketed in the United States before Oct. 15, 1994.'.

SEC. 9. GOOD MANUFACTURING PRACTICES.

Section 402 (21 U.S.C. 342), as amended by section 4, is amended by adding at the end the following:

(g)

(1) If it is a dietary supplement and it has been prepared, packed, or held under conditions that do not meet current good manufacturing practice regulations, including regulations requiring, when necessary, expiration date labeling, issued by the Secretary under subparagraph (2).

(2) The Secretary may by regulation prescribe good manufacturing practices for dietary supplements. Such regulations shall be modeled after current good manufacturing practice regulations for food and may not impose standards for which there is no current and generally available analytical methodology. No standard of current good manufacturing practice may be imposed unless such standard is included in a regulation promulgated after notice and opportunity for comment in accordance with chapter 5 of title 5, United States Code.'.

SEC. 10. CONFORMING AMENDMENTS.

(a) SECTION 201—The last sentence of section 201(g)(1) (21 U.S.C. 321(g)(1)) is amended to read as follows: 'A food or dietary supplement for which a claim, subject to sections 403(r)(1)(B) and 403(r)(3) or sections 403(r)(1)(B) and 403(r)(5)(D), is made in accordance with the requirements of section 403(r) is not a drug solely because the label or the labeling contains such a claim. A food, dietary ingredient, or dietary supplement for which a truthful and not misleading statement is made in accordance with section 403(r)(6) is not a drug under clause (C) solely because the label or the labeling contains such a statement.'.

(b) SECTION 301—Section 301 (21 U.S.C. 331) is amended by adding at the end the following:

(u) The introduction or delivery for introduction into interstate commerce of a dietary supplement that is unsafe under section 413.'.

(c) SECTION 403—Section 403 (21 U.S.C. 343), as amended by section 7, is amended by adding after paragraph (s) the following:

'A dietary supplement shall not be deemed misbranded solely because its label or labeling contains directions or conditions of use or warnings.'.

SEC. 11. WITHDRAWAL OF THE REGULATIONS AND NOTICE.

The advance notice of proposed rulemaking concerning dietary supplements published in the Federal Register of Jun. 18, 1993 (58 FR 33690-33700) is null and void and of no force or effect insofar as it applies to dietary supplements. The Secretary of Health and Human Services shall publish a notice in the Federal Register to revoke the item declared to be null and void and of no force or effect under subsection (a).

SEC. 12. COMMISSION ON DIETARY SUPPLEMENT LABELS.

(a) ESTABLISHMENT—There shall be established as an independent agency within the executive branch a commission to be known as the Commission on Dietary Supplement Labels (hereafter in this section referred to as the 'Commission').

(b) MEMBERSHIP (1) COMPOSITION—The Commission shall be composed of 7 members who shall be appointed by the President.

(2) EXPERTISE REQUIREMENT—The members of the Commission shall consist of individuals with expertise and experience in dietary supplements and in the manufacture, regulation, distribution, and use of such supplements. At least three of the members of the Commission shall be qualified by scientific training and experience to evaluate the benefits to health of the use of dietary supplements and one of such three members shall have experience in pharmacognosy, medical botany, traditional herbal medicine, or other related sciences. Members and staff of the Commission shall be without bias on the issue of dietary supplements.

(c) FUNCTIONS OF THE COMMISSION—The Commission shall conduct a study on, and provide recommendations for, the regulation of label claims and statements for dietary supplements, including the use of literature in connection with the sale of dietary supplements and procedures for the evaluation of such claims. In making such recommendations, the Commission shall evaluate how best to provide truthful, scientifically valid, and not misleading information to consumers so that such consumers may make informed and appropriate health care choices for themselves and their families.

(d) ADMINISTRATIVE POWERS OF THE COMMISSION (1) HEARINGS—The Commission may hold hearings, sit and act at such times and places, take such testimony, and receive such evidence as the Commission considers advisable to carry out the purposes of this section.

(2) INFORMATION FROM FEDERAL AGENCIES—The Commission may secure directly from any Federal department or agency such information as the Commission considers necessary to carry out the provisions of this section.

(3) AUTHORIZATION OF APPROPRIATIONS—There are authorized to be appropriated such sums as may be necessary to carry out this section.

(e) REPORTS AND RECOMMENDATIONS (1) FINAL REPORT REQUIRED—Not later than 24 months after the date of enactment of this Act, the Commission shall prepare and submit to the President and to the Congress a final report on the study required by this section.

(2) RECOMMENDATIONS—The report described in paragraph (1) shall contain such recommendations, including recommendations for legislation, as the Commission deems appropriate.

(3) ACTION ON RECOMMENDATIONS—Within 90 days of the issuance of the report under paragraph (1), the Secretary of Health and Human Services shall publish in the Federal Register a notice of any recommendation of Commission for changes in regulations of the Secretary for the regulation of dietary supplements and shall include in such notice a notice of proposed rulemaking on such changes together with an opportunity to present views on such changes. Such rulemaking shall be completed not later than 2 years after the date of the issuance of such report. If such rulemaking is not completed on or before the expiration of such 2 years, regulations of the Secretary published in 59 FR 395-426 on Jan. 4, 1994, shall not be in effect.

SEC. 13. OFFICE OF DIETARY SUPPLEMENTS.

(a) IN GENERAL—Title IV of the Public Health Service Act is amended by inserting after section 485B (42 U.S.C. 287c-3) the following:

'SUBPART 4—OFFICE OF DIETARY SUPPLEMENTS

SEC. 485C. DIETARY SUPPLEMENTS.

(a) ESTABLISHMENT—The Secretary shall establish an Office of Dietary Supplements within the National Institutes of Health.

(b) PURPOSE—The purposes of the Office are (1) to explore more fully the potential role of dietary supplements as a significant part of the efforts of the United States to improve health care; and (2) to promote scientific study of the benefits of dietary supplements in maintaining health and preventing chronic disease and other health-related conditions.

(c) DUTIES—The Director of the Office of Dietary Supplements shall (1) conduct and coordinate scientific research within the National Institutes of Health relating to dietary supplements and the extent to which the use of dietary supplements can limit or reduce the risk of diseases such as heart disease, cancer, birth defects, osteoporosis, cataracts, or prostatism;

(2) collect and compile the results of scientific research relating to dietary supplements, including scientific data from foreign sources or the Office of Alternative Medicine;

(3) serve as the principal advisor to the Secretary and to the Assistant Secretary for Health and provide advice to the Director of the National Institutes of Health, the Director of the Centers for Disease Control and Prevention, and the Commissioner of Food and Drugs on issues relating to dietary supplements including (A) dietary intake regulations;

(B) the safety of dietary supplements;

(C) claims characterizing the relationship between (i) dietary supplements; and (ii)

(I) prevention of disease or other health-related conditions; and (II) maintenance of health; and (D) scientific issues arising in connection with the labeling and composition of dietary supplements;

(4) compile a database of scientific research on dietary supplements and individual nutrients; and (5) coordinate funding relating to dietary supplements for the National Institutes of Health.

(d) DEFINITION—As used in this section, the term 'dietary supplement' has the meaning given the term in section 201(ff) of the Federal Food, Drug, and Cosmetic Act.

(e) AUTHORIZATION OF APPROPRIATIONS—There are authorized to be appropriated to carry out this section $5,000,000 for fiscal year 1994 and such sums as may be necessary for each subsequent fiscal year.'.

(b) CONFORMING AMENDMENT—Section 401(b)(2) of the Public Health Service Act (42 U.S.C. 281(b)(2)) is amended by adding at the end the following:

(E) The Office of Dietary Supplements.'.

Speaker of the House of Representatives.

Vice President of the United States and President of the Senate.

However, while the invention may include dietary supplements, thus falling under DSHEA, a great portion of the invention may be considered to fall under the government regulations for Foods For Special Dietary Use, as described below.

Foods for Special Dietary Uses (FSDU)

Unlike Nutritional Supplements, there is a regulatory definition for the term "Foods for Special Dietary Uses" defined in the code of federal regulations (21CFR 105.3, 1996) as the following, which shall be adopted in the present invention:

1. The term "Special Dietary Uses" as applied to food for man, means particular (as distinguished from general) uses of food, as follows:

a. Uses for supplying particular dietary needs which exist by reason of a physical, psychological, pathological or other condition, including but not limited to the conditions of disease, convalescence, pregnancy, lactation, allergic hypersensitivity to food, underweight, and overweight;

b. Uses for supplying particular dietary needs, which exist by reason of age, including but not limited to, the ages of infancy and childhood;

c. Uses for supplementing or fortifying the ordinary or usual diet with any vitamin, mineral, or other dietary property. Any such particular use of a food is a special dietary use, regardless of whether such food also purports to be, or is represented for general use.

2. The use of an artificial sweetener in a food, except when specifically and solely used for achieving a physical characteristic in the food which cannot be achieved with sugar or other nutritive sweetener, shall be considered a use for regulation of the intake of calories and available carbohydrate, or for use in the diets of diabetics and therefore a special dietary use.

Examples of the Foods for Special Dietary Use, (FSDU) are hypoallergenic foods, infant foods, foods for reducing and maintaining body weight, foods for the use in the diets of diabetics, and foods to regulate sodium intake and the like. It is certainly conceived that to have a specific and effective functional fiber-water product, it may be necessary to be classified as a Medical Food. The guidelines for this category described below will be respected as such:

Medical Foods (MF)

There is also a regulatory definition for the term Medical Food, defined in the Orphan Drug Act Amendments of 1988 [21 USC 360ee (b)(3)]. This definition was incorporated by reference into the Nutritional Labeling and Education Act (P.L. 101-535) in January 1990. It is incorporated into the FDA's final rule on Mandatory Nutritional Labeling, January 1993.

For the purpose of this invention, the term "Medical Food" shall mean a food which is formulated to be consumed or administered by mouth, (tube feeding), any way internally, enterally, under the supervision of a physician, and/or qualified health administrator, and which is intended for the specific dietary management of a disease or condition for which distinctive nutritional requirements based on recognized scientific principles are established by medical evaluation.

To be considered a Medical Food, a product must, at minimum meet the following criteria:

1. The product is for tube feeding;
2. The product is labeled for the dietary management of a medical disorder, disease, or condition; and
3. The product is labeled, "to be used under medical supervision", and is primarily obtained through hospitals, clinics, and other medical and long-term care facilities. Medical Foods are distinguished form the broader category of Foods for Special Dietary Use and from foods that make health claims, but the requirement that medical foods be used under medical supervision.

The term "Medical Food" does not pertain to all foods fed to sick patients. Medical Foods are foods that are specially formulated and processed (as opposed to a naturally occurring foods used in their natural state) for the patient who is seriously ill or who requires the product as a major treatment modality. Typical medical foods are enteral nutrition products, i.e., products provided through gastrointestinal tract, taken by mouth, or provided through a tube or a catheter that delivers nutrients beyond the oral cavity or directly to the stomach.

Medical foods can be classified into the following four groups:

1. Nutritionally complete formulas.
2. Nutritionally incomplete formulas, including individual "modular" type products that may be mixed with other products before use (e.g., protein, carbohydrate, or fat modular).
3. Formulas for metabolic (genetic) disorders in patients over 12 months of age.
4. Oral re-hydration products.

In some Foods for Special Dietary Use (FDSU) and in some Medical Foods (MF), the need for some nutritionally essential macronutrient and micronutrients may decrease. However, scientific literature does not indicate any chronic condition that the need for, and essential macronutrient or micronutrient is totally eliminated. Consequently, (similar to Nutritional Supplements (NS) Foods for Special Dietary Use (FDSU) and Medical Foods (MF) must minimally contain and declare on their package (e.g., under % Daily Value in the Nutritional Facts table), the concentration of all nutritionally essential macronutrients and micronutrients (13 vitamins and 14 minerals), as indicated in the Code of Federal Regulations 21 CFR 101.9 1996 (table 1). In Foods for Special Dietary Use (FDSU) and Medical Foods (MF), no essential nutrient is disregarded or is given the concentration of zero (except, for a limited time, for fat in fat-free products, and fiber in residue-free products).

To better understand this invention it is important to have a uniform and comprehensive understanding of the following with some examples presented here with, or later in a natural flow:

Understanding:

1. Solution: The process by which a gas, liquid, or solid is dispersed homogeneously (composed of all parts of the same kind) in a liquid without chemical change.
2. Suspension: The state in which the particles of a substance are mixed with a liquid but remain undissolved.
3. Emulsion: A combination of two liquids that do not ordinarily mix, such as oil and water, in which tiny drops of one liquid are evenly distributed in the other.

Understanding Encapsulations: an overview

Encapsulation, and/or micro-encapsulation: is the process of enveloping certain ingredients regardless of classification in polymetric matrices designed to be used in controlled release which may or may not include delayed release applications.

Coatings and encapsulations: A coating may be defined as a layer that covers a surface. Coatings have existed since the ninth century with the introduction of silver and gold coatings of pills in medicine. A fine powdered talcum, called pearl coating was popular at one time. Gelatin was introduced in 1838, sugar in France in 1842 and twelve years later in the US. And about 1890 enteric-coated pills were introduced. This invention covers any and/or all enrobements, which provide a function even if that function is only decorative. Encapsulation technologies, including but not limited to liposomes, may better serve this invention but coated, enteric coated, encapsulated, and/or any enrobing technology may be used simultaneously, and/or individually, by design and/or intent. Encapsulations are important not only for protecting sensitive ingredients, but also for masking certain aromas and negative tasting agents.

Further, the inventor believes that employing any or all the above can reduce the high sugar content of so many of the drinks in existence today most primarily due to the need to mask and/or change/over-ride undesirable tastes.

Sources, Understandings, Referenced Patents

The inventor is familiar with organizations and large companies that are devoted to nothing but encapsulation technologies. At this writing the inventor will call attention to a few, as well as referencing prior art in the form of noteworthy patents.

The International Micro-encapsulation Society, founded in 1995, Glasgow, is dedicated to foster and promote communication and collaboration between amongst science professionals. They define micro-encapsulations as a process that allows liquid or solid substances to be covered by a barrier wall. The wall must be chemically inert to the content of the capsule and possess an adequate stability to mechanical, thermal, or chemical influence. Various barrier wall materials may be utilized during encapsulation, which are dependent upon the application.

The Wurster process is a coating technique that is well suited to uniformly coat or encapsulate individual particulate materials. The Wurster process is an internationally recognized coating technique for precision of film coat to particulate such as powders, crystals, or granules.

The coating of pharmaceutical and/or nutraceutical micro-encapsulations helps ensure and optimize stability and prolong shelf life of reactive ingredients.

Capsules may be coated for improved barrier properties. Coating is a most effective way of masking the taste or odor of a particular ingredient, making products more palatable. Enteric coatings can be adjusted most easily to controlled and/or timed release for the maximum health benefits. In the food industry micro-encapsulations are beneficial especially to encapsulate vitamins, minerals, and functional food ingredients. Thin or partial coatings are very effective in reducing the caking of certain materials.

The Southwestern Reserve Institute has been a leader in micro-encapsulation research, development, and prototype production through most of its 51-year history. SwRI scientists and engineers use physical and chemical encapsulation techniques along with various coating materials that offer specialized microcapsule release characteristics. During 1998, approximately 50 micro-encapsulation research projects were conducted for the food, nutraceutical (health food), pharmaceutical, cosmetic, personal care, consumer product, agrochemical, veterinary medicine, and chemical industries.

Consumer products make up one of the largest market sectors for the SwRI micro-encapsulation program. The Institute's contributions in micro-encapsulation technology have led to advances in detergents, bleaches, carpet cleaners, deodorants, antiperspirants, toothpastes, and paints. Microcapsules prepared for these applications range in size from less than a micrometer to several thousand micrometers.

SwRI uses a variety of micro-encapsulation technologies to produce edible coatings for food components. Encapsulation of acidulates, aromas, bacteria, flavors, nutritional oils and supplements, vitamins, minerals, dietary fibers, leavening agents, and peroxides is used for improved taste and odor masking, for controlled-release applications, or for improved thermal, oxidative, and shelf-life stability.

SwRI scientists, working with Enviroquest Ltd. of Cambridge, Ontario, Canada, successfully co-developed and co-patented a microencapsulated medicament for ingestion by honeybees and other beneficial insects. The product was tested in beehives against tracheal mites. In the study, encapsulated menthol was delivered to honeybees' blood (haemolymph) and killed the mites. The encapsulated menthol also showed excellent shelf life. Additional trials are scheduled, and U.S. Food and Drug Administration approval is pending. SwRI will continue to assist in the development and manufacture of the product.

SwRI scientists conduct micro-encapsulation research and development for a variety of applications, including industrial, agrochemical, food, and consumer products.

Bio Dar was established in 1984 as a United States and Israeli joint venture now under LycoRed, Koor Group of Companies. They are specialists in microencapsulated vitamins and minerals for the fortification of food products. Their specialty extends to technologies of how to keep the food additive particle from imparting an undesirable taste to the surrounding ingredients. This technology is most valuable for where the micro-encapsulations are mixed in with the other ingredients and this technology is critically important to this invention.

Further they deal with Carnetine, Amino Acids, Herbal Extracts, as well as other nutritional components where the role of micro-encapsulation is to avoid hygroscopicity, minimize interactions, and eliminate the oxidation of these materials. Further they have the ability to do multiplayer micro-encapsulations for mainly drug delivery. U.S. Pat. No. 4,749,575 to Rotman, (Bio-Dar Ltd. IL), titled Microencapsulated medicament in sweet matrix.

In addition to encapsulated, micro-encapsulated, microparticled, digestive and systemic uses, enzymes can also be used in fiber-water formulations containing encapsulated, micro-encapsulated, micro-particled, herbals (extracts and/or the like), vitamins, minerals, and various other diagnostics, therapeutics, dietary supplements, nutraceuticals, pharmaceuticals, and/or the like known to those skilled in the art, because, in combination, they provide a number of unique opportunities, including, but not limited to:

(1) Improved absorption
(2) Improved bio-availability
(3) Improved stability
(4) Maximized activity
(5) Balance the body various systems (example; PH, hormones)
(6) Diagnose Delivery Sequencing;

Within the present invention, an "effective amount" of a composition is that amount which produces a sadistically significant effect. For example, an "effective amount" for therapeutic uses is the amount of the composition comprising an active compound herein required to provide a clinically significant. Such effective amounts will be determined using routine optimization techniques and are dependent on the particular condition to be treated, the condition of the patient, the route of administration, the formulation, and the judgment of the practitioner and other factors evident to those skilled in the art.

The dosage of the compounds of the invention will vary according to the extent, and severity, of the need for treatment, the activity of the administered compound, the general health of the subject, and other considerations well known to the skilled artisan. The inventor here is hoping, that through this invention medicants and/or the like can be administered on a daily basis as an oral dose.

While dietary oral administration may be preferable in most instances (for reasons of ease, patient acceptability, and the like), alternative methods of administration may be appropriate. This can relate to any and/or all of this invention, which can be administered by enteral feeding (naso-gastric tubes and/or gastrostomy tube . . . detailed later). Additionally, it is possible that there be a split between delivery vehicles on the advice of a knowledgeable practitioner. For example it is possible to, as an example need part of the formula in a different format injected and then daily follow-ups orally . . . and/or the like with any combinations known to this best skilled in the delivery of such.

In another preferred method of the invention, the administration of the invention conceived as to be part of the diet (or as aforementioned in conjunction with another route), is intermittent rather than continuous. Thus, preferred protocols may include administering the invention once every other day, three days, once every week, optionally, in varying amounts, at each time of administration. Such forms of administration may be preferable to daily administration, or to a "consistent", several times a day dosage.

Thus, by "intermittent" administration is meant that the invention with the compounds and/or compositions containing the actives are provided to the subject only sporadically, with substantial periods between dosages, or until the results are assessed. Thus, there could be incremental intervals between administrations.

There might be situations where there is alternation between the administrations of one or more formulas designed to work in consort. Or if only a single dose is administered, there might be a substantial period, after dosage, until results are assessed. That is, while one day 1 multiple dosages may occur (or only one) there would be no dosage the next day, at least. Or if the dosage is on a daily basis, a substantial interval is permitted to elapse before results are assessed.

A single bolus dose is preferred over a multiplicity of smaller dosages in some instances. Preferred "intermittent" regimens would comprise administering the compounds or compositions every other day, every two days, every five days, or on days unevenly spaced but separated at least by a one day interval between days on which a dosage occurred. In summary, by "intermittent" dosage regime is meant either a single bolus dose or multiple dosages that comprise only a small proportion of the timeframe over which the subject is being treated. The timeframe over which treatment is administered is measured by the time between initial administration and assessment of the results. The inventor feels the aforesaid most specifically refers to those that are administered under the care of a medical professional and thus classified as such. Additionally, they might not even appear in the consumer marketplace, but be given directly by a health care practitioner, in a healthcare facility, or under a prescription, or under the advice of a healthcare practitioner as a medical food (described in detain in this filing) and/or more than one of the combinations above may best service the delivery.

The ability to manipulate substances in a carrier, such as is invented here, leaves much room for further options of controlling delivery. Just as an I.V. drip offers advantages so does the ability to sip, over time, a drink. This, in its own right, is considered a form of a continuous delivery.

Using this invention also provides the advantage of continuous dosing of one or more ingredients, over time, which is often preferred to intermittent bolus dosing. Two examples of continuous delivery, other than an IV drip, would be the implantable insulin pump, and subcutaneous and/or submucosal patches such as the estrogen patch.

These are based on metering the delivery of a substance to closely mimic the body's natural production of the said substance (e.g. insulin) and/or another medicant. Further, and it has been demonstrated that with the metered dose (given slowly over time) it may not be necessary to give as much of a medication etc. as would be necessary with a bolus dose ergo reducing and/or eliminating all together and, if not all unwanted side effects which may present. An understanding here is based on substances that, when administered in a bolus dose, may be harmful at one end of the spectrum and/or at the other end not as effective as compared to administering a small continuous dose. An example would be substances that may cause severe to mild gastric and/or metabolic upset.

Vitamin C is a good example, as it is not stored in the body, but instead excreted in the urine. Also if one is inclined to look at the example of an endurance ingredient, like even a simple sugar, whereby encapsulations (sized appropriate) will give a timed release of the glucose into the blood stream hopefully avoiding a rapid rise, and subsequent drop, of a blood sugar level. No doubt, we need sugar for metabolism, but not so large a dose at one time, which could upset the delicate insulin mechanism, by which the sudden drop off (per individual) can defeat the initial purpose. By encapsulating glucose you can get more of the effect of a slow release carbohydrate in a different form. (The inventor is fully aware that you cannot concentrate glucose, however later the inventor addresses encapsulations, which are larger and resemble beads, seeds, and/or the tapioca balls common in Asian drinks)

It is possible to have micro-micro-encapsulations within a specific micro encapsulation. This would resemble a ball within a ball. Each ball can be engineered so that it is contained within is the same active, a different active, and/or a combination of one or more actives.

In U.S. Pat. No. 5,209,978, to Kosaka et al. (Taisho Pharmaceutical Co., Ltd. (JP) issued May 11, 1993, titled "Seamless soft capsule and production of," we are taught that there now exists an invention of a soft capsule composed of a plurality of cells coalesced to each other and filling substances encapsulated in the individual cells, the walls of at least one of the cells being formed of a material different from a material forming the wall of at least one of the other cells, and being seamless, thus creating a soft capsule with a multi-cellular structure.

It is noted that the partitioning material is able to handle substances, which might react unfavorably with each other if the partitioning material was not properly adapted to the situation. And additionally, by being seamless, there is not the opportunity for leakage and/or air penetration, which would cause problems.

A multi-cellular soft capsule having its inside partitioned by a film was recently proposed (see Japanese Laid-Open Patent Publication No. 109520/1985). This patent document states that the multi-cellular soft capsule is obtained by partitioning a soft capsule shell composed of an upper film and a lower film, into two cells by means of a partitioning film, and filling different drugs into the two cells. As a result, two drugs, which do not mix, can be stably included in a single soft capsule. By using materials having different solubilities and dissolving speeds, it is possible to cause one part of a single capsule to be released and absorbed in the stomach and the other part, in the intestines. It is also possible to make one part of the capsule fast-releasing and the other part slow-releasing.

So to that end, and to those skilled in the art, and/or the advancement of scientific skills, it is, or will be conceived that there can be, more than just one ball inside another.

U.S. Pat. No. 6,022,500 to John et al., Feb. 8, 2000, (The United States of America as represented by the Secretary of the Army) titled; Polymer encapsulation and polymer microsphere composites has claimed the ability to encapsulate an active enzyme. The discovery is a novel method of encapsulating enzymes, other solutes or nanoparticles in a polymer matrix. The present invention relates to polymer microspheres suitable for the encapsulation, stabilization and release of biologically active molecules such as enzymes, drugs, biocides and the like. The present invention also relates to advanced materials, especially composites of polymers with organic or inorganic compounds. What is further most interesting is that the polymers may exhibit a preparation of high luminescent, (both photoluminescent and electroluminescent) qualities.

Other patents of reference are U.S. Pat. No. 4,711,784 (Yang/Warner Lambert); U.S. Pat. No. 5,024,842 (Edgren, Theeuwes/Alza Corp.); U.S. Pat. No. 5,051,261 (Mc Ginity, Chang/FMC Corp.); U.S. Pat. No. 5,009,819 (Popescu, Mertz/The Liposome Company); U.S. Pat. No. 5,653,996 (Hsu/Genentech CA); U.S. Pat. No. 5,891,465 (Keller/BioZone Laboratories Inc. CA); U.S. Pat. No. 6,007,838 (Alving, Owens, Wassef, Nabila, U.S.A. Dept. of the Sec. of the Army/Washington D.C.); U.S. Pat. No. 6,190,591 (van Lengerich/General Mills MN); U.S. Pat. No. 5,922,350 (Janoff et al./The Liposome Company NJ).

The Releasing of Encapsulations

It is further conceived, that this invention includes encapsulations, and/or micro-encapsulations, that may be uniformly released and/or timed released which may be in the form of liposomes, and/or any other form that fits under the category of encapsulations, and/or micro encapsulations. In addition, flavoring, coloring, aromatics, pharmaceutical and/or nutritionally active components can advantageously be encapsulated and/or nicroencapsulated to ensure stability.

It is conceived that whether uniformly released or not, controlled release, they may be nothing more than bursts of color and/or flavoring. These as an example, might be especially delightful to children. Encapsulations might separately, and/or additionally, provide what might be termed as an entertainment factor, especially if they are colored, and/or of different sizes, and/or shapes. First, the color red may be released in the mouth, then yellow, and resulting in a red-yellow and/or orange mix. This can be fun and/or educational. Further, if a double membrane is used then the encapsulations may be colored, varied, and/or consistent. The "beads" locked between all or part of the walls of the double membrane may or may not be fully transparent. Following suit, the same can occur separately and/or in combination as related to flavor. These encapsulations may follow all of the claims here for encapsulations. If, as an example, the encapsulation reacts with the saliva in the mouth then it is possible to take in a liquid with no color, and suddenly you have a colored mouth/tongue/even teeth. In this capacity it is possible to have the liquid adhere to the teeth and ergo you can potentially have a plaque disclosure functional fluid with or without additional nutritive elements. (It is conceived that additional internal diagnostically need substances can be consumed in the same fashion) Most often timed release, or sometimes referred to as controlled release, provides none of the aforementioned, and/or any, and/or all, of the just aforementioned, whereby they additionally may provide the ability to suspend the release of active ingredients until they reach the designated position along the gastro-intestinal tract. This is most valuable in the delivery of pharmaceuticals, nutraceuticals, OTC Drugs, diagnostics, enzymes, pre-biotic and/or pro-biotic formulations and/or the like.

Further, the encapsulations may be used to preserve and/or better deliver the active ingredients to the aforesaid. Further, they may, and/or may not, travel farther down the digestive tract to the gut for release, all at one time, and/or over a predestinated period. It is therefore to be claimed that any and/or all of the just aforesaid may be included.

The microcapsules can be formulated to release their contents when they are exposed to saliva either by fracturing and/or dissolving. Alternatively, the microcapsules can be formulated within the micro-beads, or other components whereby the microcapsules then release their contents, even up to several hours post ingestion, at a predetermined designated point along the digestive tract. In this way it is possible to precisely deliver a labile component.

Various and assorted encapsulated ingredients can be included in one encapsulation regardless of form. This can mean that there be several granules inside of one (1) encapsulation and/or micro-encapsulations, which goes of inside of a larger encapsulation. Encapsulation controls the stability, compatibility etc. of ingredients, as well as the timing of ingredient release etc. Again may be used for decorative purposes.

Encapsulations and swallowing: What must be kept in mind is that particles must not interfere with ones ability to swallow the liquid. Again, reminding that the viscosity altering gums and/or the delivery of actives by encapsulations/micro-encapsulations for swallowing purposes, and/or desirability, and/or necessity, is a component of the invention. This includes but not limited to the purpose of being swallowed in a way that will go virtually unnoticed by the user.

However, it is possible, and might also be desirable, to go noticed by the user by having a "swallowable" particle(s) deliberately to enhance the texture of the liquid. This enhancement of texture may also serve a valuable medical function addressing a swallowing disorder, or in another context address those on diets who need oral gratification of not just drinking but chewing to feel satisfied.

There are beverages, and even in non visible to the eye beverages, in cans in Asia. Additionally noted in Asia there are beverages, which incorporate small seeds (chia, poppy, etc.), that one swallows in conjunction with the ingested liquid. For example, in Asia there are beverages containing sesame seeds or other small seeds, which are commonly consumed, and seem to present no problem in swallowing. In the United States we have orange juice with pulp and this, likewise, presents no problem to the consumer. If we look at a thickened product we can project that there be many particle, encapsulations or nit that bring forth nutritive ingredients. This could resemble enriched noodles (like the alphabet) in soups.

However, the inventor has a range of intentions which will present a much lesser feeling of "particles in liquid" than the aforementioned, and certainly no greater than, or close to, the size and texture of the aforementioned, unless so desired for a specific use and under the guidance of those in the medical profession. While other particles are to be considered an inclusion in the invention, in this instance the inventor is specifically referring to a "swallowable" encapsulation(s).

Encapsulations Present to Ensure the Bio-availability of Ingredients, in Integrity, to the User:

Often, delicate and unstable ingredients are not bio-available to the user. Many actives, which are delivered to the oral cavity, or directly into the stomach, are altered and/or partially or wholly destroyed by the saliva and/or stomach acids and therefore become, in part or in total, bio-unavailable to the system or human system. Therefore, the process of specific design and execution of the encapsulations becomes critically important. Although the inventor may have an understanding and/or ideas in relation to how best to circumvent technical problems there are those skilled in the art of encapsulations and prior existing art, which are far more qualified. The inventor has noted some of the just said previously, but will include a list here of referenced patents specifically addressing this technology and the variations of.

1. U.S. Pat. No. 6,033,888 to Batich et al., (U. of FL. Gainsville), titled Process for microencapsulating cells. This patent addresses both the injectable and/or oral administration of encapsulations. The compositions and methods of the subject invention are illustrated herein with reference to encapsulation of certain bacteria. Bacteria, which produce a useful product can be encapsulated and introduced into a human or other animal. The encapsulation of bacteria is specifically exemplified herein by the encapsulation of *Oxalobacter formigenes*. The encapsulated *O. formigenes* can be introduced into a human or animal and the bacteria continue to produce and release enzyme but are not subject to attack from the immune system. For oral administration, multi-encapsulated microspheres of cellulose acetate phthalate in poly-2-vinylpyridine (pKa=3.5) were prepared to protect the enzymes from gastric juices. Polymeric matrix micro-encapsulation of microorganisms is a relatively new technology, which has potentially major implications in the treatment of various afflictions. Examples of afflictions in which treatment involving microcapsules could be advantageous are diabetes and urinary stone diseases.

a. Insulin dependent diabetes mellitus (IDDM) is a severe disease, which afflicts millions of Americans, causing substantial disruption of lifestyle and often resulting in severe health problems. The exact causes of IDDM have remained largely a mystery, despite years of intensive research on this disease. It is now widely recognized that IDDM is an autoimmune condition whereby the body's natural immunological defenses destroy the .beta.-cells of the pancreas. Beta.-cells are responsible for the production of insulin, and, once a substantial portion of the .beta.-cells are destroyed, those individuals afflicted with the disease must rely on exogenous sources of insulin, usually in the form of injections. The success of pancreas or islet cell transplantations is very limited because of immune responses typically mounted by the recipient against the foreign cells. Urolithiasis, or urinary stone disease, is a common urinary tract problem afflicting more than 10% of the U.S. population. Urinary tract stones are usually classified according to their composition, with the most frequently encountered (70%) being the calcium stone composed of calcium oxalate alone or calcium oxalate mixed with calcium phosphate. Although precipitation of calcium oxalate depends on a urine saturated with both calcium and oxalate ions in a metastable state, it has been argued that the oxalate ion concentration is more significant in the formation of urinary calcium oxalate stones. Thus, the management of oxalate in individuals susceptible to urolithiasis would seem especially important. The majority of oxalate in plasma and urine is derived from the endogenous metabolism of ascorbic acid, glyoxylate, and to a lesser degree, tryptophan. In addition, between 10% and 20% of the urinary oxalate is absorbed from the diet, especially through ingestion of leafy vegetables and plant materials, although there is disagreement in the literature about the relative amounts of diet and endogenous oxalate. Ingestion of ethylene glycol, diethylene glycol, xyhtol, and excess ascorbic acid can lead through metabolic conversions to disorders of excess oxalate. Use of methoxyfluraneas an anesthetic can also lead to oxalosis. Aspergillosis, infection with an oxalate-producing fungus, can lead to production and deposition of calcium oxalate. Other causes of excess oxalic acid include renal failure and intestinal disease. It is believed that lowering the oxalate levels in the plasma, and subsequently the urine, would decrease the incidence of calcium oxalate stone formation. Unfortunately, there are no known naturally occurring oxalate degrading or metabolizing enzymes in vertebrates. Catabolism of oxalic acid appears restricted to the plant kingdom.

2. U.S. Pat. No. 5,571,441 to Mark Andon (The P&G Co. Cincinnati, Ohio), titled Nutrient supplement compositions providing physiologic feedback brings forth the importance of being able to add nutrition to existing products. However this patent relies only on the novel composition, not on the novel delivery into water, a water-like composition, and in this case based on the patent issued on fiber-water via encapsulations with the benefits and versatility they bring forth. It is noted here that the inventor acknowledges the stated invention but perceives that under her "novelty" if one or more stimulants are added to a water composition water composition that they be encapsulated and released at different rates so that the consumer does not get that "buzz" or immediate release effect and then the drop off, but instead a steady controlled release overtime.

a. (The inventor here, Stillman, claims that while many substances have been encapsulated, no one has encapsulated stimulants with the specific intent, shall we say of preventing "the bolus dose jitters" and "unsteadyness" commonly associated with the "all at once ingestion" of such stimulants. (Also relating to caffeine which effects colon motility it may present an advantage to time release caffeine for that reason as well)

b. The importance in the Andon Patent is that it references the following: "Vitamin and mineral supplements for human and veterinary use are commonplace. Nutrient intake surveys have shown large segments of the world's population consumes substantially less than the recommended amounts of numerous vitamins and minerals. For example, in the U.S.A. 60%, or more, of females' age 20–29 years consume less than the recommended dietary allowance of vitamins A, E, B-6, folic acid, and the minerals calcium, magnesium, iron, and zinc. It is generally known that some diets, heavy physical exercise and disease conditions may require the intake of considerable quantities of vitamins and minerals apart from those generally available from what is considered a normal diet. Nutritional supplements are primarily important for those who have inadequate diets, however, individuals with a reduced ability to utilize or absorb vitamins and minerals from food, e.g., the elderly, also need nutritional supplementation.

c. A physiological signal that many people are accustomed to is the alertness response received by food-type tonics or bracers, such as caffeine. These materials can be useful for creating a perceived benefit and for establishing more regular use of nutritional supplements. These natural bracers, and in particular, the xanthine alkaloids (methylxanthines) are found in various plants. The methylxanthines are obtained by extraction of plants (e.g. coffee beans, cola nuts, tea plants). Plants containing methylxanthines are known to those skilled in the art. Preferred methylxanthines are 1,3,7-trimethylxanthine (caffeine), 1,3-dimethylxanthine (theophylline) and 3,7-dimethylxanthine (theobromine). Many people establish a consistent pattern of caffeine use due to its well-documented effects as a tonic. One or more caffeine containing food or beverages—cocoa, chocolate, coffee, tea, soft drinks—are consumed daily by most adults and children. Cocoa and chocolate contain only small amounts of caffeine and are not usually consumed for the same reason as coffee, tea, and soft drinks.

d. Although it is clear that many people consume caffeine and other related tonics, there are well-recognized problems with the usual caffeine containing foods. Many people consume much affricated coffee in the morning. Coffee is known to stimulate the gastric mucosa and increase stomach acid secretions, which contributes to heartburn and irritation of ulcers. Coffee is also bitter tasting, so some people consume caffeine in the form of soft drinks. The high acid content of soft drinks, phosphoric for colas and "pepper" type soft drinks and citric acid for fruit flavored type beverages is well documented to etch or erode the enamel of the tooth surface. In addition, cola and "pepper" type soft drinks contributed greatly to the total phosphorus intake of the diet which imbalances the calcium to phosphorus ratio and can cause a negative effect on bone metabolism. Tea is another widely consumed source of caffeine but it also has some negatives associated with it. Tea contains anti-thiamin factors, which stress the thiamin stores in the body and can lead to poor thiamin nutritional status. In addition, teas are often consumed with lemon and/or sugar. The lemon can increase the risk of dental erosion due to etching of the teeth from the high citric acid content and the sugar can provide a source of fermentable carbohydrate to the oral bacteria, which increases the risk of caries. Apart from the negative effect of caffeine containing beverages, many people look for alternative ways to provide alertness benefits.

e. It would be desirable to provide the sought after bracing effects of caffeine or other similar ingredients in a composition, which eliminates the negative effects of normal caffeine source carriers, and yet provides a convenient and effective composition for promoting good health.

f. Thus, an object of the current invention is to provide compositions of vitamins and/or minerals and a central nervous system tonic in a convenient dose form. These compositions would provide vitamin and mineral supplements with a noticeable physiologic response and also the desired alertness effects without the negative components associated with typical caffeine containing beverages. It is an object of this invention to provide nutritional supplements which provide the physiologically positive alertness effects of a bracer."

g. Some people avoid caffeine due to health reasons, i.e. the effect of caffeine on elevating blood pressure. It would be desirable, therefore, to have additional nutritional supplements, which provide a physiological signal other than those of methylxanthines. Green tea is believed to have a relaxing benefit owing to the presence of flavanols (i.e., the catechins and epicatechins). Green tea has had several physiologic benefits attributed to it. It is believed to lower blood pressure and have other soothing and healing effects. These benefits have been attributed to flavanols. Black tea contains polymerized flavanols, which do not impart the same degree of benefits of catechins and epicatechins.

h. Compositions comprising vitamins and/or minerals and flavanols would be useful as a convenient dose form for improving the diet while also providing a physiologic response and combined benefits of flavanols with those of vitamins and minerals to yield a more comprehensive product for the promotion of health.

i. It is further recognized that certain individuals seek the benefits of caffeine or similar ingredients, but closely control the amount of caffeine they ingest due to sensitivity to caffeine or because of caffeine's undesirable effects (i.e. the promotion of nervousness). For some people, the negative effects of caffeine may eventually outweigh the positive so that caffeine is avoided altogether. Tea contains caffeine. However, the caffeine in tea does not appear to be as physiologically available due to the presence of flavanols. It is well known that the flavanols, in particular the unoxidized flavanols, present in green tea, help to control the negative effects of caffeine. See, for example, French Patent No. 2,586,532 issued to Balansard et al.

j. Vitamin and mineral supplements having unique compositions containing a bracer, such as caffeine, along with the beneficial effects of flavanols or green tea would be useful for improving nutritional status and providing positive alertness benefits while limiting the negative effects.

k. Both caffeine and flavanol containing products are primarily consumed in the morning to obtain an alertness effect. Typically vitamins and minerals are also consumed in the morning. It would be more convenient if the nutritional supplements, methylxanthines and flavanols could be administered conjointly in a form, which would provide nutritional supplementation and alertness without negative effects. These nutrient supplement compositions would be useful in providing a physiologically positive alertness benefit while providing feedback beneficial in establishing more regular use of a supplement.

l. The uses of methylxanthines, and/or flavanols are known in pharmaceutical and therapeutic preparations. The methylxanthines have primarily been used to treat various problems such as asthma, abdominal complications, and migraine headaches. However methylxanthines and in particular, caffeine, is used to counteract the adverse effects (i.e. drowsiness) caused by other ingredients in the pharmaceutical preparation. The flavanols, have been used for centuries to combat numerous diseases and illnesses, both real and imaginary. While the beneficial effects of methylxanthines and flavanols, in particular caffeine and green tea are suggested by the literature, the use of these materials in conjunction with vitamin and mineral supplements or the co-administering of the materials with vitamins and minerals in a convenient form is not known.

m. It would be desirable, therefore, to have vitamin and mineral supplements containing flavanols and methylxanthines or flavanols alone wherein physiological feedback is achieved.

3. U.S. Pat. No. 5,681,606 to Hutchison, et al. (R. P. Scherer, Troy, Mich.), titled: Method of preparing a water-based beverage, it is noted, by the inventor as documentation of how viable it is to encapsulate ingredients to go into a water-based beverage. However, this is a separate unit to be added to the water-based beverage and not already present in the water-based beverage, as in Stillman, whereby the actives will be released once ingested by the consumer. This invention releases ingredients into the beverage, and makes a valid point for releasing at the bottom of the beverage inside the container, which in total concept is important in supporting, but is not the invention of Stillman, as the encapsulated ingredients release when in contact with the liquid. Extrapolation is as follows: "A method is disclosed of preparing a beverage in the form of a dilute aqueous solution, suspension or dispersion of an encapsulated product. The capsule is added to a potable liquid, and the capsule material breaks down when submerged in the liquid to release its contents and itself dissolve. A primary advantage of providing the product in this way is that it can be confined within the capsule in liquid form, and can therefore disperse or dissolve in water more readily. Additionally, the capsule would normally sink to the bottom of the body of water before releasing its contents, thereby ensuring that the contents are released within the body of water, and not at the surface thereof.

Overview of Changing Viscosities and the Importance of

Viscosity is an internal property of a fluid that offers resistance to flow. For example, pushing a spoon with a small force moves it easily through a bowl of water, but the same force moves mashed potatoes very slowly.

Viscosity changing additives, regardless of their source, present many advantages previously addressed. (Viscosity changes, especially in beverages, are also used for those with swallowing difficulties. Viscosity changes give the consumers a feeling of being full and will, in many cases, satisfy and/or ameliorate hunger pangs. (A thicker product is a viable consideration for dieters).

More noteworthy is the fact that several, viscosity-changing additives are classified as fiber ergo boosting the amount of health promoting and enhancing soluble dietary fiber. As an example, the gums fall into this category. Then to notice with each gum comes forth individual and/or overlapping healthful value(s).

The inventor is looking at the entire range of gums, working individually and/or in consort to achieve special qualities and desired effects. As an example, in conjunction with gelatin, or as a substitute for, additives, regardless of category may be impregnated into the gummy by those qualified in the art and/or encapsulations may be in held in the gummy (inventor's U.S. patent application Ser. No. 09/936,209 CIP of PCT/US 01/09171 titled: Method of Hydration: Infusion Packet System(s) Support Member(s) Delivery System(s) and Method(s) with Business Model(s) and Method(s). Gums, and gum systems, can improve mouth feel, content, and suspend encapsulations, as they can any particle(s), fleck(s) and/or the like. The same hold true for pulp (most commonly in citrus juices). An example is 1. Novartis® guar gum, Benefiber® which addresses bowel regularity.
2. Tic Gums (Belchamp, Md.), as an example, offers a wide range of gums which can be used alone and/or in combination such as:
   a. Agar is produced from red seaweed and comes in two species: Graciliaria, which forms firm gels, and, Gelidium, which forms soft gels.
   b. Agaroid®
      Agaroid® RS, line of readily soluble Agar systems, can be used to create gels and other textures. Agaroid RS can replace gelatin in many applications and are certified kosher.
   c. Alginate
      Alginate is a gel-forming gum extracted from brown seaweed.
   d. Gum Arabic
      Gum Arabic is used to encapsulate flavors, emulsify beverages, boost soluble dietary fiber, coat candy shells, and control water in baked goods.
   e. Aragum®
      Aragum® gum systems are built on the foundation of dried gum arabic and incorporate other gums to take advantage of unique synergies.
   f. Caragum
      Our Caragum line consists of gum systems specially designed to extend locust bean gum in a variety of applications.
   g. Carrageenan
      Carrageenan is extracted from red seaweed and is available in three different forms: kappa (gelling), iota (gelling), and lambda (non-gelling). Most often Carrageenan provides set to puddings, binds water in meat products, and improves mouthfeel in milkshakes.
   h. Colloids
      TIC Pretested® systems are formulated using various gums to take advantage of the functional properties of each individual ingredient as well as the synergies created when the ingredients are combined.
   i. Freedom Gum
      Eliminate or reduce the need for costly propylene glycol alginate in beverages and salad dressings.
   j. Gum Acacia
      Brings forth excellent emulsification and binding properties. Used as emulsifier of flavor emulsion concentrates, used in formulation of "cloud" emulsions, as a foam stabilizer in beer, as a clarifying agent in wines. Additionally gum acacia functions to lower cholesterol. A product recommendation from Tic Gums is their TIC PRETESTED® Colloid 1004 "T" Powder which dissolves in Cold Water, used in relation to citrus pulp which was developed for line of fruit drinks containing Pulp & Fat (emulsifies coconut cream & suspends pineapple pulp). Used at 0.15% to 0.30%. Heat Stable at low pH. Drinks, Pulp Suspension
   k. Guarcel®
      The Guarcel® offers relatively low-cost thickeners with the protein reactivity of cellulose gum. Guarcel improves suspension and stability characteristics.
   l. GuarNT®
      GuarNT® Bland products offer the thickening benefits of Guar Gum, without the grassy odor or mealy taste typically associated with Guar.
   m. Locust Bean Gum
      Locust Bean Gum retains moisture, reduces syneresis, and improves texture, and creates smooth meltdown.
   n. Nutriloid®
      Boost the soluble dietary fiber level, improves mouth feel, and modifies the texture of functional foods, all-natural, non-GMO Nutriloid gums. I about 85% soluble dietary fiber on a dry weight basis.
   o. Pectin Extracted from the rinds of citrus fruit, TIC Pretested® Pectin is an all-natural gelling agent usually used for jams and jellies, stabilizes acidified milk products, and adds mouthfeel in beverages. Both low methoxyl (LM) and high methoxyl grades of pectin are available.
p. Pre-Hydrated®
   Pre-Hydrated® Gums disperse without lumping, even with minimal agitation
q. Saladizer®
   Improve mouth feel and cling, stabilize emulsions, suspend spices, and reduce fat using our specially designed gum systems.
r. Ticagel™
   Specially formulated to yield distinct gelling and viscosity characteristics, our Ticagel™ line of thickeners and gel formers are used in a variety of applications. Current uses include improving mouthfeel of acidified beverages.
s. Ticaloid®
   Our unique TIC Pretested® systems are formulated using various gums to take advantage of the functional properties of each individual ingredient as well as the synergies created when the ingredients are combined.
t. Ticalose® CMC
   Create clear viscous solutions with our Ticalose® CMC. Also known as cellulose gum or carboxymethyl cellulose, Ticalose CMC is available in a range of viscosities and mesh sizes. Ticalose CMC thickens reduced sugar table syrups, improves texture.
u. Ticaxan® Xanthan
   Produced using fermentation, our Ticaxan® Xanthan is a multi-purpose thickener and stabilizer. Commonly used in salad dressings, Xanthan gum is tolerant to extreme heat, pH, and salt conditions.
v. Tragacanth Replacers
   TIC Gums has developed a full line of tragacanth replacers, which offers superior emulsion stability. They are relatively unaffected by pH and heat. Tragacanth replacers can thicken and emulsify.
   NEED the gray boxes off to the left
off
off
off Understanding Viscosity Perhaps the cart has been put before the horse however it is most important to be well versed on viscosity. There are many ways to measure viscosity, including attaching a torque wrench to a paddle and twisting it in a fluid, using a spring to push a rod into a fluid, and seeing how fast a fluid pours through a hole. Then there is the exercise, which uses one of the oldest and easiest ways: that is to simply see how fast a sphere falls through a fluid.

In this invention all encapsulations are not necessarily spheres, a sphere at this time shall serve as a good example. The faster the sphere falls, the lower the viscosity. This makes sense: if the fluid has a high viscosity it strongly resists flow, so the sphere falls slowly. If the fluid has a low viscosity, it offers less resistance to flow, so the ball falls faster.

The measurement involves determining the velocity of the falling sphere. Dropping each sphere through a measured distance of fluid, and measuring how long it takes to traverse the distance accomplish this. Thus, you know distance and time, so you also know velocity, which is distance/time.

The formula for determining the viscosity is impressive, decorated with Greek letters and a squared term, but simply amounts to multiplying some numbers and then dividing by some others:

$$\text{viscosity} = \eta = \frac{2(\Delta\rho)ga^2}{9v}$$

Delta p=difference in density between the sphere and the liquid
G=acceleration of gravity
A=radius of sphere
V=velocity=d/t=(distance sphere falls)/(time of it takes to fall)

This equation makes sense in that spheres that fall slowly have low velocities. This makes the denominator small, so the answer (viscosity) is large. Viscosity is measured in units of Pa s (Pascal seconds), which is a unit of pressure times a unit of time. This is not especially intuitive How does it relate to flowing liquids? One-way of looking at it is to realize that pressure is force per square area. This makes a little more sense: force applied to the fluid, acting for some length of time. [Note: the exercise uses kilograms, meters, and seconds, rather than grams, centimeters, and seconds. Viscosity can be measured in g-cm-s, with the resulting unit called the poise; 10 poise=1 Pa s. You may prefer those units to kg-m-s because densities are the more familiar grams per cubic centimeters.]

It is also critical to look at the density of the encapsulations (and/or any particles which may not contain encapsulations) for which they may vary due to one or more factors. Using spheres of different radii and densities and measuring the viscosities of at least two liquids gives a good idea of this unusual physical property and the power of an equation to predict behavior. For example, if group A uses a marble (density of about 2800 kg/m$^3$) and group B uses a steel ball bearing (7800 kg/m$^3$), and both measure the viscosity of the same liquid, they will find that the velocities differ, but the viscosities will be the same, within the error of measurement.

| | | Viscosity of Water | | |
|---|---|---|---|---|
| Temp | Absolute Viscosity | Kinematic Viscosity | | |
| °F. | Centipoises | Centistokes | SSU | ft$^2$/sec |
| 32 | 1.79 | 1.79 | 33.0 | 0.00001931 |
| 50 | 1.31 | 1.31 | 31.6 | 0.00001410 |
| 60 | 1.12 | 1.12 | 31.2 | 0.00001217 |
| 70 | 0.98 | 0.98 | 30.9 | 0.00001059 |
| 80 | 0.86 | 0.86 | 30.6 | 0.00000930 |
| 85 | 0.81 | 0.81 | 30.4 | 0.00000869 |
| 100 | 0.68 | 0.69 | 30.2 | 0.00000739 |
| 120 | 0.56 | 0.57 | 30.0 | 0.00000609 |
| 140 | 0.47 | 0.48 | 29.7 | 0.00000514 |
| 160 | 0.40 | 0.41 | 29.6 | 0.00000442 |
| 180 | 0.35 | 0.36 | 29.5 | 0.00000385 |
| 212 | 0.28 | 0.29 | 29.3 | 0.00000319 |

Understand viscosities as related to the valuables associated with the encapsulations and with the relation to the surrounding fiber-water is very critical in designing the to be invented products. As can be noted in the above chart the temperature of the liquid/water can change the viscosity. This will be taken into consideration by those knowledgeable in the art. With that understand the inventor will rely on the experts in such technologies as deemed necessary to create exactness/consistency in product(s).

With multiple viscosities in one clear container and each having a different color, it is possible to layer a drink in a container, best visible like a bottle, by filling it with layers of different viscosities (best if colored) and even if put in all together (or in a predetermined arrangement) with time the layers will settle according to viscosities. If the layers are also flavored, (the flavoring can or cannot be associated with the color) then it is possible to have a drink where first you get the red/cherry and then the orange/orange and then the yellow/lemon etc. Or the red can be lemon etc. When the bottle is still for a specific amount of time, the layers will sort out. Even a rainbow can be layered. What fun for children to drink from this bottle whereby they get all mixed up and then watch them settle again. Additionally different layers can bring forth different additives.

Understanding the "Lava Lamp" Concept as a Delivery System for a Beverage

The main association here is that you do not change the viscosity of the entire product, but selectively you use one or more viscosities that do not necessarily stay in suspension but move around at will, and/or in the hands of a consumer, as an example, or both. It is conceivable that much remains clear, while other portions may cloud, but all has a negligible taste factor. The delivery is the action along with ancillaries such as color, aroma etc. regardless of employed delivery system.

Aroma can come from the bottle cap the headspace/nitrogen (PepsiCo patents as noted in this document later). Aroma is certainly an important factor in appeal and not discounted at all by this inventor.

Further, color can denote grades/strengths of fiber, or just color for color's sake. Or the same holds true for viscosity modules, encapsulations, etc. Color can denote what is in each encapsulation(s) in terms of additives, quantities, and/or the like. Any coding system can be used.

In the 1960 an Englishman developed what was to be called a "Lava Lamp." To inventor Stillman this concept of float and changing elements can now be shifted to reside inside a beverage bottle serving to entertain and expanded so as to deliver added health benefits, along with hydration, is most intriguing.

The commercial name "Lava Lamp" is used here as a descriptive to presents a case whereby two contrastingly colored, immiscible liquids are contained in a bottle-like chamber. However the Lava Lamp needs a heat source, which was located in the base. The heat from the source causes one of the two liquids to in effect "boil," producing a slow but observable upward flow of large globules of the one liquid relative to the other. Upon moving away from the heat source, the globules cool and tend to settle toward the heat source. Thermal currents in the liquids produce an ever-changing geometry of the globules. Light directed through the bottle-like chamber enhances the visual effect produced. When the globules settle they are again reheated and the process repeats itself producing a continuously changing display until the heat is removed.

In the drink concept, here invented, the product in the container can be heated, (or chilled), which will transpose to affect the viscosities of the product inside. This will in effect affect the "globulization" of the particle mass inside. Those skilled in the art shall most efficiently design within the confines of the manufacturing and honor the integrity of the contained property.

Further it is conceived that the container, regardless of the material be so designed, and/or adjusted using the laws of physics, including but not limited to using the technologies covering heat and cold, light and dark, gravitational forces, etc. to "best fit" the intention of the movement.

The inventor notices that other devices utilize the influence of gravity to produce visual effects. One such device is of the type described in U.S. Pat. No. 3,564,740 to Calfee, in which a multi-compartment display device is provided with liquids of different specific gravities stored therein. The visual effect produced by the relative movement of the liquids is obtained by inverting the device like an hourglass to produce the gravity flow of the heavier liquid in the downward direction with the consequent upward displacement of a lighter liquid. The flow of liquids is accomplished by a "valving", or porting arrangement in barriers or partitions, which divide the several compartments of the display device, one from the other.

In U.S. Pat. No. 4,034,493 to Ball (Whamo-O Mfg. Co., San Gabriel, Calif.) titled; Fluid novelty device the inventor notices that Ball compares his invention to that of Calfee as follows. The relative flow of liquids of different specific gravities, utilized in the Calfee, (U.S. Pat. No. 3,564,740) can be utilized by the present invention, but with several important differences. In the first instance the beading or droplet forming action is provided by the liquids themselves as the heavier liquid flows around baffles and obstructions in its flow path without the use of ports or valves of any kind. In addition, because the invention utilizes a pair of plates defining a narrow chamber for the liquids, the color contrast and visual effect is maximized because each of the liquids abuts the inside surfaces of the plates and are viewed directly through the plates.

In Calfee one liquid flows through the other interiorly of the container walls and the view thereof is obscured to the extent that the line of sight to the drops of the first liquid passes through said other liquid. In the Ball patent a display device, consisting of a sealed chamber, defined by two closely spaced panes or plates of a transparent or translucent material. Liquids of different specific gravities and selected viscosities are located in the chamber. In operation, the device is inverted and the liquid of the heavier specific gravity flows through the liquid of the lighter specific gravity in distinct, spaced apart beads or droplets under the influence of gravity. The downward flow of the heavier liquid causes the upward displacement of the lighter liquid. A series of obstructions of various shapes and geometric configurations are interposed in the flow path of the heavier liquid to change its flow path and create the visual display.

It is also possible to add decoration to the drink, which may, or may not, bring forth one or more healthful additive. These may be in the form of dots, (not encapsulations) flecks, or anything that would be considered a particle that is visible. It may also be defined as a candy with or without the typical characteristics of a candy. U.S. Pat. No. 6,416,800 to Weber et al., issued Jul. 9, 2002, titled Fiber optic candy teaches an edible fiber optic light source is combined with confectioneries, in particular candy, to form a safe edible material possessing unusual combinations of internally generated colors and optical images. The basic design consists of a edible food pipes that may be placed within various confectioneries or foodstuffs that elicits light of various colors and intensities while standing untouched and even as the product is ingested. This effect may be use for frozen products, as the inventor has covered in fiber-water (U.S. Pat. No. 6,248,390) Popsicle® and ice cubes and ergo they are considered to be covered in this application as well.

Ingredient Categories:

In the present invention, the term "edible" means safe or fit to be eaten. The term "digestible" means to transform into an assimilable state.

Understanding Soluble Fiber

Fiber or "roughage" is a component of food that remains undigested as it passes through the gastrointestinal system. The vast majority of dietary fiber consists of polysaccharides of plant origin. The most obvious fiber is the cellulosic wall that surrounds plant cells. Many of these cells are actually called "fibers", hence the name "fiber" for this dietary component. However, there are actually two forms of fiber: insoluble fiber—the classic cellulosic material, and soluble fiber—water soluble polysaccharides that are not digested by human or carnivore digestive systems. Both types of fiber bind considerable water and, thus, have a softening effect on the stool. However, soluble fiber may, depending on the precise polysaccharides involved, be metabolized or partially metabolized directly by bacteria in the colon. Both type of fibers tend to increase motility within the gastrointestinal tract thus speeding transit time of wastes and lowering the risk of acute and chronic medical problems. Like water, fiber is essential for human health and is not metabolized by humans.

It has been discovered that dietary fiber appears to moderate the rate at which sugars and fats are absorbed from the intestine. The exact reason for this effect is not completely understood. In the case of simple sugars, slowed absorption translates to a more gradual rise in blood sugar following eating. This is important in the managing of diabetes and may also help prevent adult onset diabetes. In the case of fats, the fiber seems to help prevent damaging levels of cholesterol in the blood. This seems to be due to a binding of bile salts and cholesterol to the fiber so that these materials are excreted with the feces rather than being absorbed or reabsorbed. Studies show adequate fiber clearly lowers the risk of heart disease and tends to bind toxins, including toxic metals, allowing them to exit safely from the digestive system.

In fact, it has been suggested that deficiency in dietary fiber is related to numerous disease states, including colon cancer, heart disease, cerebral apoplexy, appendicitis, and diabetes. This is apart from those diseases more closely linked to constipation, such as intestinal toxemia, hemorrhoids, irritable bowel syndrome (IBS), colitis, diverticulitis, varicocele, and cholelithiasis (gall stones). It is believed that dietary fiber performs various useful physiological functions including reduction of serum cholesterol, limitation of insulin secretion, and acceleration of bowel evacuation. All these factors make fiber a very important nutrient substance, the sixth most important by some commentators, although it is not actually metabolized.

Any water-soluble carbohydrate polymer can act as dietary fiber as long as no human enzymes are capable of hydrolyzing these polysaccharides into simple sugars. Preferentially, the polymers should also not be readily metabolized by bacteria common in the human gut so they can continue to provide a "bulking" effect. However, some types of soluble fiber are metabolized by and do promote growth of beneficial bacteria. This generally has a positive effect, as the beneficial bacterial may also tend to lubricate the stool and/or prevent the growth of other bacteria that may release toxins (Prosky, Leon J. of AOAC Int'l. 82:223–35 [1999]).

Soluble fiber comes from a wide range of plant sources. Water-soluble plant pectins and pectic materials, galactomannans, arabanogalactans and water-soluble hemicelulose can act as soluble fiber. Many plant "mucilages," gums, and soluble polysaccharides found in grains, seeds, or stems such as psyllium, guar, oat (beta glucans), astragalus (gum traganth), gum ghatti, gum karaya (Sterculia gum); and gum acacia are also soluble fiber. Algal polysaccharides such as agar or carrageenan also behave as soluble fiber as do other indigestible carbohydrates, such as maltodextrins or dextrins, produced by chemical or enzymatic digestion (e.g., partial hydrolysis) of starch, gums and other carbohydrate polymers. Soluble cellulosic ethers and other derivatives such as carboxymethyl cellulose behave as soluble fiber as do indigestible carbohydrate polymers artificially prepared using bacterial enzymes In experimenting with various types of soluble fiber, the inventor noticed that a number of the more refined materials, such as lower molecular weight grades of mulin (for example see U.S. Pat. No. 5,968,365 to Laurenzo, et al., issued Oct. 19, 1999, titled Preparation of inulin products), specialized dextrins, maltodextrins and partially hydrolyzed guar gums. The preferred dextrins or maltodextrins are prepared by controlled hydrolysis of vegetable starches (e.g. potato or corn) as is described in U.S. Pat. No. 5,620,873 to Ohkuma et al., issued Apr. 15, 1997, titled Process for preparing dextrin containing food fiber. The hydrolyzed guar gum is of the type discussed in U.S. Pat. No. 5,260,279 to Greenberg, Norman A., issued Nov. 9, 1993 (Sandoz now Novartis), titled: Enteral nutrition and medical foods having soluble fiber (available in the United States as BENEFIBER from Novartis Nutrition of Minneapolis, Minn.; available in other countries as SUN-FIBER from Taiyo of Japan).

Non-digestible storage carbohydrates such as inulin are also important soluble fibers. A number of companies are now providing an entire range of "soluble fiber" materials of food grade. For example: TIC Gums of Belcamp, Md. provides gums which are considered also as a soluble fiber, Novartis Nutrition of Minneapolis, Minn., a guar gum trademarked in the U.S. as Benefiber® and Imperial Sensus of Sugar Land, Tex. provides inulin.

Any water-soluble carbohydrate polymer can act as dietary fiber as long as no human enzymes are capable of hydrolyzing these polysaccharides into simple sugars. Preferentially, the polymers should also not be readily metabolized by bacteria common in the human gut so they can continue to provide a "bulking" effect. However, some types of soluble fiber are metabolized by and do promote growth of beneficial bacteria. This generally has a positive effect, as the beneficial bacterial may also tend to lubricate the stool and/or prevent the growth of other bacteria that may release toxins. (Prosky, Leon J. of AOAC Int'l. 82:223–35(1999)).

Soluble fiber comes from a wide range of plant sources: water-soluble plant pectins and pectic mater, galactomannans, arabanogalactans and water-soluble hemicelulose can act as soluble fiber. Many plant "mucilages," gums, and soluble polysaccharides found in grains, seeds, or stems such as psyllium, guar, oat (beta glucans), astragalus (gum traganth), gum ghatti, gum karaya (Sterculia gum), and gum acacia are also soluble fiber. Algal polysaccharides such as agar or carrageenan also behave as soluble fiber as do other indigestible carbohydrates, such as maltodextrins or dextrins, produced by chemical or enzymatic digestion (e.g., partial hydrolysis) of starch, gums and other carbohydrate polymers. Soluble cellulosic ethers and other derivatives such as carboxymethyl cellulose behave as soluble fiber as do indigestible carbohydrate polymers artificially prepared using bacterial enzymes. Non-digestible storage carbohydrates such as inulin are also important soluble fibers.

It is permissible and often advantageous to blend an assortment of different soluble fibers to create any particular fiber-water as the foundation for this invention. In fact this invention may dictated the fiber(s) used and the quantity and/or the delivery. It is believed that the various soluble fibers have essentially identical properties when it comes to providing bulk and hydration to the stools. However, it is not yet clear which soluble fibers will prove superior in altering lipid or sugar absorption, etc. Of the soluble fibers presently available the indigestible dextrins, inulins and partially hydrolyzed guar gum appear to provide the most water clear solutions. However, many dextrins and inulins contain a small amount of a metabolizable component and have a slight sweet taste. Therefore, there can be an advantage of providing a portion of the soluble fiber in the form of hydrolyzed guar gum or some other flavorless and totally non-metabolizable compound. Even though some of these materials may produce a less clear solution, a combination with a clear soluble fiber can yield a solution that is both high in fiber and clarity and low in sweetness or other taste. Other soluble fibers can be combined to realize the advantages of the different fibers. Inulins have a slightly sweet taste and while not appreciably metabolized by humans, bacteria in the colon metabolize inulins. In some cases such colonic metabolism may provide a distinct advantage and would mitigate towards including inulins in the mixture. To be more specific, pectins (and gums) form a gel in the gastrointestinal track by absorbing water and swelling as much as 10 times its weight. They slow down the passage of food and thus they give us a feeling of being full. The "feeling full" feeling that they provide aids weight loss, which will be covered later in fiber-water for dieters. Pectins are good for diabetics because it slows down food absorption after meals while further removing unwanted metals and toxins from the body. Pectin is valuable during radiation therapy or X-rays, and it helps lower cholesterol, ergo lessens the risk of heart disease and gallstones.

An appropriate diet is an important part of the management of diabetes mellitus. Later it will be covered in detail, fiber-water for diabetics, whereby we want to keep any glucose portion at the lowest concentration. The goal is to maintain blood glucose levels as close to normal as possible and maintain normal lipid levels. Diets for persons with diabetes do not have to be sugar free. Dietary carbohydrates affect blood glucose levels more than other foods and need to be eaten in consistent amounts at meals and snacks each day. Diet-fiber-water and fiber-water for diabetics, if administered throughout the day in metered amounts, will aid in the targeted program and may even be packaged in 2,4,6,8, or more self contained units thus creating a "water a day program" with each water being time specific.

While it may seem out of order it is important here to touch upon one of the objects of the invention briefly and that is to create a pack a day be it 2 or more bottles designed to work in consort. Basically more than one bottle of a water composition (and/or a fiber-water composition) designed to be drunk throughout the day. The bottles may be marked as with numbers, colors, naming or the like. See object of the invention Further, additional additives would be in support of the diabetic needs for supplementation forming a solution or a vicious appropriate (jelly like) beverage with or without encapsulations of active ingredients.

Arabanoglactan (AG), a natural polysaccharide extracted from already harvested Larch trees from Larex Incorporated, with headquarters in St. Paul, Minn. markets several versions of their arabinoglactan. They are as follows:

1. ClearTrac™ AG is a natural prebiotic fiber which acts as a food source to stimulate growth of the friendly bacteria (Bifidobacteria, Lactobacilli) commonly found in the gastrointestinal tract (colon).

2. ImmunEnhancer™ AG is a natural polysaccharide offering a number of immunological stimulating properties related to the immune system including:
   Natural Killer (NK) cell and Macrophage activation
   Increased release of various cytokines including interferon gamma (IFN gamma), tumor necrosis factor alpha, interleukin-1 beta (IL-1beta) and IL-6
   Promotes healthy limits to cell replication.
3. Fiber-Aid AG is a natural pre-biotic fiber which acts as a food source to stimulate/promote an increase in the Bifidobacteria, Lactobacilli (good bacteria) found in the digestive tract/gastrointestinal tract (colon). In addition to the promotion of friendly bacteria FiberAid® AG has been shown to increase the production of short chain fatty acids (SCFA). SCFA are important in the colon as they reduce colon pH and help establish a beneficial colon environment. In particular butyrate has been shown to support healthy cell division in the colon. Also, a recent human clinical at the University of Minnesota demonstrated cholesterol reduction in hyperlipidemic individuals.
4. Larex® UF is Intended for biomedical applications and is greater than 99% pure Arabinogalactan with applications in:
   Biomedical Cell Separation—Used for density gradient blood cell and/organelle separation.
   Drug Conjugation—Enhanced drug delivery; Increases solubility, activity and delivery effectiveness of various water insoluble drugs such as Amphotericin B.

Cellulosels is good for hemorrhoids, varicose veins, colitis, and diverticulitis. It is excellent for removal of cancer-causing substances from the colon wall, constipation, and a boost for weight loss.

Hemicellulose is good for weight loss, constipation, and colon cancer. It fights carcinogens in the intestinal tract.

Lingnin is good for lowering cholesterol levels, protecting against colon cancer and preventing gall stone formation. It binds with bile acids to remove them. It is recommended for diabetics.

Gums and Mucilages are known to regulate blood glucose levels, aid in the lowering of cholesterol levels and help in the removal of toxins.

Matsutani of Japan markets a maltodextrin, Fibersol-2™, which is a soluble dietary fiber (90% min dsb). Fibersol-2™ is produced from cornstarch by pyrolysis and subsequent enzymatic treatment (similar to the process to manufacture conventional maltodextrins) to purposefully convert a portion of the normal alpha-1,4 glucose linkages to random 1,2-, 1,3-, and 1,4-alpha or beta linkages. The human digestive system effectively digests only alpha 1,4- linkages; therefore the other linkages render the molecules resistant to digestion. Thus, Fibersol-2™ is GRAS as maltodextrin, resistant to human digestion, and conforms to all working industrial and scientific definitions of dietary fiber Inulin The carbohydrate inulin, which occurs in over 36,000 plants, is all natural and non-digestible by the human digestive system. Entire populations have consumed inulin, for centuries, as a main staple in various food sources, such as onions, wheat, J. artichokes, asparagus, and others.

However, current consumption from natural sources is not large enough to provide an efficacious inulin dose (approximately 5 g/day minimum for improved physiological health) as a unique soluble dietary fiber and preferred food for healthy intestinal bacteria. (Good gut micro-flora such as bifidobacteria and lactobacilli).

1. In addition; inulin provides a myriad of health properties for which; under DSHEA, and further clarified by the FDA Apr. 29, 1998 in 21 CFR Part 101 Food Labeling: Nutrient Content Claims, Definition of Term: Healthy, statements of structure or function may be made for mainstream inulin-containing products, e.g.
  a. "Promotes growth of beneficial bacteria such as bifidobacteria", "bifidogemc",
  b. "Helps to maintain a normal, well balanced gut micro-flora",
  c. "Helps maintain intestinal flora",
  d. "Stimulates natural Bifidus flora",
  e. "Inulin is efficiently converted to short chain fatty acid",
  f. "Helps maintain cardiovascular function and a healthy circulatory system",
  g. "Helps promote urinary tract health",
  h. "Helps maintain a healthy cholesterol level",
  i. "Helps to regulate blood glucose level",
  j. "Helps maintain regularity",
  k. "Helps improve mineral bio-availability",
  l. "Supports the immune system", are allowed.
  m. Further impressive literature is replete with the benefits of inulin hailing its ability to:
  n. Suppress pathogenic gut microorganisms and their toxins,
  o. Prevent ulcerative colitis,
  p. and mal-absorption,
  q. Demonstrates positive influences on blood sugar regulation
  r. and also balance insulin for diabetics.
2. Further to improved
  a. Calcium absorption for osteoporosis
  b. and immune activation as related to disease prevention,
  c. Anti-tumor effects,
  d. Reduction in food allergies,
  e. and potential help for autoimmune diseases like
    i. Crohn's and
    ii. Rheumatoid arthritis.
3. In recent years, scientific evidence for reducing serum lipid levels in man, and animals, using inulin has grown. (Shown to lower LDL and raise HDL)

In food and/or beverage, inulin has neutral taste, odor, and color, and is ideal to be incorporated into an infusion packet blend.

The inventor has noted the following patents related to inulin as relevant; U.S. Pat. No. 5,972,415 to Brassart, et al., issued Oct. 26, 1999, titled Nutritive composition (Nestec S.A. CH); U.S. Pat. No. 5,792,754 to Green et. al., issued Aug. 11, 1998, titled Nutritional composition containing fibres (Nutricia NL). Of most relevance is U.S. Pat. No. 5,721,345 to Roberfroid, et al., issued Feb. 24, 1998, titled "Prevention Of Mammary Carcinogenesis and Breast Cancer Treatment." U.S. Pat. No. 5,550,113 to Mann, issued Aug. 27, 1996, titled "Blood Sugar Regulating Composition and Methods Relating Thereto."

Inulin is recommended sometimes for diabetics; it has a mildly sweet taste, and is filling like starchy foods, but because it is not absorbed, it does not affect blood sugar levels.

The inventor has just provided a short description, or some of the most applicable, and noteworthy to date, soluble fibers.

Understanding Water and the Importance of Hydration

Although water is not metabolized, it is essential for metabolism. Water serves a variety of functions in the body, including regulating temperature, protecting and cushioning vital organs, removing waste, and converting food into energy. A majority of our body is water, serving as the solvent for the chemical reactions of life. Thirst is one of the first signs of dehydration, but one cannot rely on thirst to tell when you need more water. Once dehydration begins, the thirst response becomes even less effective, particularly in older people, who are less likely to drink sufficient water. The reader's attention is drawn to "Problem: thirst, drinking behavior, and involuntary dehydration" by Dr. John E. Greenleaf, of NASA, (Medicine and Science in Sports and Exercise, 24:645 (1992)).

It is generally agreed that the average adult person should consume at least eight, 8 oz. glasses of water per day—more if the individual is undergoing stress, exercising strenuously, ill, or in very hot climates. Unfortunately, most people drink water only when parched, not consuming enough to completely address and/or reverse dehydration.

When the body is dehydrated, nutrients cannot be as readily delivered to the cells, nor waste products be as readily removed. With dehydration, viscosity of the blood is increased so that efficiency of circulation is decreased. Such impaired circulation can ultimately lead to vascular damage and disease. At the same time, because the dehydrated body seeks to reverse this situation, more water is removed from the bowel. This causes excessive compaction and hardness of digestive residues with resulting constipation and potential accumulations of toxins in the bowel (which toxins may ultimately be absorbed into the blood stream). Further, there is abundant evidence that constipation may lead to a myriad of medical problems related to the gastrointestinal track including colon cancer, possibly as a result of prolonged contact between cells of the colon and toxin laden feces. It is critically important to be able to regularly eliminate toxins from the body in a healthy person and far more critical in those with health challenges.

Understanding Mineral Waters

Definitions of Mineral Waters

Europeans as well as other cultures all over the world use and experience the health benefits of not just bathing in mineral waters, but additionally by drinking natural mineral waters. Over two thousand years ago the Etruscans and Romans drew their water from natural springs. In Europe drinking mineral water has been part of the standard life style for centuries. The following brief description of mineral waters, with some of their intrinsic health benefits in addition to hydration, is necessary, to better understand the new and novel proposed invention, functional fiber-waters.

The following is according to the Food and Drug Administration (FDA) of the United States:

"'Spring Water' must be derived for an underground formation from which water flows naturally to the surface of the earth. No particular physical/chemical properties are required other than those normally applied to drinking water". Spring waters are normally light waters with minimal mineral taste. Total dissolved solids (TDS) are allowed up to 249 mg/liter. The taste may vary depending on the origin of the water. Based on the composition of the ground, this will determine the amounts of mineral components that the water collects on its way from the source. If, for instance, the soil is rich in calcium and magnesium, it will result in hard water. On the contrary, a high altitude mountain source that flows direct into a bottling plant, will result in a pure and light water This such water may be recommended for delicate organisms such as newborn babies or people with sensitive kidneys.

"'Mineral Water' is Spring Water that contains at least 250 mg/liter to 500 mg/liter, which we can classify this water as 'Mineral—Low Mineral Content' or 'Light Mineral'. Recommended for anybody who wants to compromise the refreshing taste with a moderate replenishment of minerals such as athletes and/or outdoor workers.

Above 500 mg/liter, the water can be called just 'Mineral'. These waters (TDS between 501 and 1000 mg/liter) are already heavy waters where the taste is definitely affected by the chemical-physical content of the water. Recommended for people with moderate mineral deficiencies.

'Mineral Water'—High Mineral Content (TDS above 1000 mg/liter are heavy waters for people with stronger mineral deficiencies. In some cases, administration under medical supervision is recommended.

It is important to the inventor to have an understanding of ingredient categories that are especially sensitive to proper handling. In most cases they cannot just be place at will, in a liquid, and maintain their stability, bio-availability, ergo their effectiveness and integrity.

Sweeteners

When one thinks of sweeteners one usually thinks of sugar or fructose is from fruits/fruit sugar and lactose is from milk a Milan sugar. Many sweeteners were discovered accidentally Saccharin, Sucralose, Cyclamate, Acesulfame which has a sweet taste; and some people experience a bitter-metallic aftertaste (much like saccharin). Its onset of sweetness is rapid. The sweetness potency relative to sucrose is about 200, Aspartame (Nutrasweet®, provides 4 calories per gram. Since it is about 180 times as sweet as sugar, the amount of aspartame needed to achieve a given level of sweetness is less than 1% of the amount of sugar required. Thus 99.4% of the calories can be replaced and the list goes on.

The newest area of focus are the sweet proteins (Thaumatin (Tayte and Lyle UK); Brazzein (University of Wisconsin); Miraculin (BioResources Intl.) Mollein (University of Penna. Kirin Brewery)

The discussion best saved for actual product development future but to be included so that the practicing of (using) this invention may include one, or a combination of more than one, sweetener with a specific purpose, by design, as will be discovered later.

Understanding Pro-biotics and Pre-biotics

For thousands of years man has used bacteria to preserve food, but it was not until the end of the $17^{th}$ century that the existence of bacteria could be visually observed. The research today we know that various micro-organisms have different characteristics and can be applied for different purposes. Microbial technology can now be used, for example, to vary the nutrient content, flavor, consistency, and most valuable in keeping the quality of food high.

Important in this area is the fact that basic research during the last decades have demonstrated that the administration of viable cultures of certain gastrointestinal tract organisms have a positive effect on the recipient's health and well being. This has been demonstrated for both humans and animals.

The common prerequisite for a pro-biotic organism to be effective against various forms of gastrointestinal tract disorders, and/or building a healthy GI tract are that they should be able to pass through the acid barrier of the stomach, withstand the effects of bile salts, and be able to colonize the intestinal lining. A goal is to stimulate gastrointestinal epithelial cell development, which would result in longer and healthier intestinal villi, deeper crypts, and hence more efficient nutrient uptake.

Thus noting that both pro-biotics and pre-biotics are delicate/sensitive and up until recently, have not been able to be handled effectively long-term, without refrigeration.

With new encapsulation technologies available, we are now able to handle these organisms successfully. Once again they are not only valuable in human health but animal health as well.

Definition of pro-biotics, by Marcel B Roberfroid, From the Department of Pharmaceutical Sciences, Universite Catholique de Louvain, Brussels.

"A pro-biotic is a viable microbial dietary supplement that beneficially affects the host through its effects in the intestinal tract. Important health-related effects associated with pro-biotic administration include immune enhancement, (enhance host resistance to a broad spectrum of bacterial, viral, protozoal, and physiological challenges) and the alleviation of lactose intolerance and more have been reported in human studies. Some evidence suggests a role for pro-biotics in reducing the risk of rotavirus-induced diarrhea and especially colon cancer (which makes an excellent case for combining pro-biotics with soluble fiber which has been shown to bind to toxins, ergo removing said toxins from the colon).

Pre-biotics are non-digestible food ingredients that benefit the host by selectively stimulating the growth or activity of one or a limited number of bacteria in the colon. Work with pre-blotics has been with the inulin-type fructans, which have generated sufficient data for thorough evaluation regarding their possible use as functional food ingredients. Among the claims are constipation relief, suppression of diarrhea, and reduction of the risks of osteoporosis, atherosclerotic cardiovascular disease associated with dyslipideria and insulin resistance, obesity, and possibly type 2 Diabetes. It is conceived that by combining a combination of pro-biotics and pre-biotics that this combination might improve the survival of the bacteria crossing the upper part of the gastrointestinal tract, thereby enhancing their effects in the large bowel. In addition, their effects might be additive or even synergistic."

Pre-biotics are organisms and/or substances, which help to improve the environment of the intestinal tract. Pre-biotics are foods that contain live bacteria and are known to increase digestibility, speed recovery from diarrhea (especially guar gum), enhance immune function (arabinoglactan, a fiber, is a good choice), reduce certain cancers, and lower blood cholesterol levels, (again an excellent case for combining with fiber).

Pre-biotics are foods or nutrients that are used by specific bacteria and can be added to the diet to increase the chances of these particular bacteria growing and thriving in the intestine.

The bacteria that live in the intestines make up a very large, and very diverse population. The numbers of each kind of bacteria change, depending on age, diet, health status, and use of drugs and supplements. The bacteria that do thrive do so because they are able to adhere to the intestinal wall, and use the semi-digested food that is passing through the intestines. Because some bacteria have specific nutrient requirements, it has been proposed that adding these particular foods or nutrient to the diet could be a way of increasing the numbers of specific bacteria.

Just as an example set forth here, the inventor calls attention to U.S. Pat. No. 6,180,099 to Paul, (Metagenics, CA.), titled, "Method of using immunoglobulin and fiber-containing compositions for human health" identifies preferred and beneficial human intestinal microorganisms such as *Lactobacillus acidophilus, L. bulgaricus, L. casei, L. fermentum, L. salivaroes, L. brevis, L. leichmannii, L. plantarum, L. cellobiosus, Bifidobacterium adolescentis, B. infantis, B. longum, B. thermophilum,* and *B. bifidum.* More preferably, the beneficial human intestinal microorganism is selected from *L acidophilus* and *B. adolescentis.*

Understanding Antioxidants

Antioxidants help to protect the body from the formation of free radicals. Free radicals can cause damage to the cells, impairing the immune system and leading to infections and various degenerative diseases such as heart disease and cancer. Free radical damage is thought by scientists to be the basis for the aging process as well.

Antioxidants are defined as any substance inhibiting oxidation. Oxidation reactions can occur anywhere in our body, in any organ and/or cell. When oxidation reactions get out of control and slip past the constraints of the body's own protective mechanisms, this results in the formation of free radicals. Antioxidants help prevent the formation of free radicals, stop the domino effect of free radicals, and even repair, or "clean up", after the damage has been done.

These reactive molecules that damage tissue can be controlled through antioxidant supplementation. As with enzymes, these antioxidants can be taken separately or in combination(s). Taking anti-oxidants individually, as with enzymes might target specific an area more intensely. At times this is more if not as valuable as taking a combination of antioxidants that will affect several tissues in the body, while individual antioxidants would target specific areas. This invention acknowledges that both approaches are set forth of which the inventor believes necessary.

There are many antioxidants and more discovered as time and science continue to make discoveries. The main proven antioxidants are Vitamin C, Vitamin E, and Vitamin A. (.beta.carotene or a cartinoid mixture which is substantially equivalent in vitamin activity to quantity of .beta.carotene).

While Hoffman La Roche makes a water-soluble vitamin E that has no taste, Vitamin C, ascorbic acid, does have a taste. Further, too much Vitamin C at one time can cause gastric upset. Additionally, Vitamin C is not stored in the body. Therefore it may be of great advantage to encapsulate all or part of the ascorbic acid and also to consider time releasing. Vitamin A is not water-soluble and therefore in a fiber-water antioxidant composition, which may include those just said, and others, encapsulations once again, may be most desirable.

Airline travel as an example: It is a wide spread fact that dehydration is a major factor in airline travel, and passengers are urges to drink, hopefully 6–8 oz. It is advisable, that for every hour in flight to prevent such dehydration, passengers follow the guidelines aforesaid. It is not a wide spread fact that in the cabins of airplanes many free radical scavengers are present. Long flights especially wreck havoc on the body at best, and certainly do not provide enough fiber when one evaluates the airline meals. Ergo, not just fiber-water (which provides hydration and soluble fiber) but a target specific antioxidant fiberwater for airline travel, with or without supporting additional nutritional supplementation, is ideal.

There are other stressful emergency situations for which fiber-water is beneficial and now with additional additives is more target specific. This is not to be confused with a general population anti-stress situation but emergencies handled by the Red Cross, FEMA and like such agencies (governmental or privatized, or non-profit).

In U.S. Pat. No. 6,248,390, inventor Stilman clearly states the importance of such product(s). "When under stress humans and animals are known to reduce their consumption of water. Yet when the body is stressed by disease, additional water is required, yet this is exactly when many reduce their fluid intake. Further stress may influence people to prefer sugar-laden beverages (comfort food) or caffeine beverages for alertness—these types of beverages actually increase ones water requirement and may lead to dehydration. Thus, it is beneficial to provide fiber-water as opposed to plain water in emergency supplies to be used in case of natural disaster—fire, flood, storm, earthquake, or hurricane and it is suggested fiber-water be stocked by FEMA or its international counterparts. During such a disaster people are stressed and are often forced to move from their homes and everyday surroundings. Emergency situations often dictate a shortage of food and water and/or that food and water will be available at abnormal times. This combined with the general shortage of fresh fruits and vegetables, which are a key source of dietary fiber, during such an emergency naturally leads to loss of regularity. Emergency food drops rarely contain fresh fruits and vegetables. Having to deal with the emergency is bad enough. Adding severe constipation and dehydration simply makes a bad situation worse. Assuring ample supplies of fiber-water is intended (what happened here?) to alleviate many of these problems".

Anti-oxidants of importance include, but are not limited to, the following:

1. Alpha-Lipoic Acid, helps to neutralize the effects of free radicals.
2. Bilberry is a strong antioxidant that keeps capillary walls strong and flexible. Supports and strengthens collagen, inhibits growth of bacteria, anti-inflammatory, anti-aging, anti-carcinogenic.
3. Coenzyme Q10, is an immunological stimulant, increases circulation, anti-aging, and beneficial for cardiovascular system.
4. Cysteine, (an amino acid) detoxifier of alcohol, tobacco smoke, and environmental pollutants. Anti-aging.
5. Glutathione, defends against damage from smoking, exposure to radiation, cancer chemotherapy, and toxins such as alcohol. A detoxifier of heavy metals and drugs, it aids in the treatment of blood and liver disorders.
6. Melatonin, is an antioxidant/free radical scavenger
7. Selenium, guards the cells of blood, heart, liver, and lungs. It stimulates antibody response to infection.
8. Vitamin C, free radical scavenger. It increases the synthesis of interferon (natural antiviral substance produced by the body).
9. Vitamin E, prevents the oxidation of lipids and protects the heart.

Understanding Enzymes for the Purpose of Encapsulating, with or without Viscosity Changes Enzymes are the powerhouses of every living cell. They either start chemical reactions, or they make them run faster.

Enzymes sustain life. The late Dr. Edward Howell, a physician and pioneer in enzyme research, called enzymes the "sparks of life". These energized protein molecules play a necessary role in virtually all of the biochemical activities that go on in the body. They are essential for digesting food, for stimulating the brain, for providing cellular energy, and for repairing all tissues, organs, and cells. Life as we know it could not exist without the action of enzymes, even in the presence of sufficient amounts of vitamins, minerals, water, and other nutrients.

An enzyme is a complex protein molecule originanting from living cells and capable of producing certain chemical changes in organic substances by catalytic action, such as in digestion. In fact enzymes are best known for their ability to improve digestion by breaking down proteins, fats, and carbohydrates in our food. In this way, digestive enzymes improve health by allowing the nutrients in our foods to be extracted, absorbed, and carried through the bloodstream to the various organs and cells of the body. This is why improving digestion can benefit so many conditions that at first do not appear to have anything to do with digestion (such as allergies, acne, aging, headaches, gout, etc.). By augmenting the body's enzymes, supplemental digestive enzymes free pancreatic enzymes to perform other health functions in the body, such as boosting immune function, decreasing inflammation, and improving circulation. Further, digestive enzymes are essential for proper detoxification and for maintaining healthy flora in the colon.

In the book, "The Complete Book of Enzyme Therapy," Dr. Anthony Cichoke presents a practical guide to using the natural power of enzymes to maximize health and combat a host of common disorders, including, but not limited to, digestion. Dr. Cichoke is a strong advocate of including plenty of water (on a daily basis) while avoiding, coffee, soft drinks, alcohol, artificial fruit drinks, and canned juices. (Page 436) On page 437, Dr. Cichoke stresses the importance of safe water. Chlorinated or fluoridated water in excessive amounts can kill the "good" bacteria living in the intestinal tract which can also increase free-radical formation in the blood, leading to tissue damage and accelerated aging.

Enzymes make digestion possible allowing the user to drink the fiber-water enzyme composition before, during, or after a meal with the specific intent of the invention being: "digesting fiber enriching water". By the nature of the specific enzymes used to break down food, especially protein, as in the popular Atkins protein diet, the enzymes will help digest and break down the proteins while providing hydration along with the fiber that these diets so critically lack.

Enzymes go far beyond the breakdown of protein, being essential for everything that occurs in the body, including, but not limited to, digestion, breathing and circulation. Your body uses enzymes to fight disease and inflammation and to slow the aging process. Supplemental enzymes aid digestion, dissolve blood clots, and fight back pain; however as we age the numbers of our enzymes and their activity levels decrease.

Enzymes remain unchanged even after an action is complete, and because they have so many applications, it is better to classify enzymes based on what they do, what substances they act upon (substrates) and the reaction they start or accelerate. Enzymes are very substrate specific; some work best within a specific pH range—a measure of acidity and alkalinity. There are six main groups of enzymes, each having fundamentally different activities:

1. Hydrolyses consists of
   a. Proteases which breakdown the peptide bonds in proteins
   b. Amylases break down carbohydrates,
   c. Lipases break down fats (lipids), improves fat utilization, a digestive aid,
2. Isomerases break down the rearrangement of chemical groups within the same molecule.
3. Ligases catalyze the formation of a bond between two substrate molecules through the use of an energy source.
   a. Lyases split the double bonds between atoms with the accumulation or disassociation of chemical groups.
   b. Oxidoreductases make oxidation and reduction possible.
   c. Transferases transfer chemical groups from one molecule to the other. Again, enzymes are best known for their treatment in their ability to aid digestion and ease digestive problems.

Systemic enzyme therapy takes the use of enzymes one step further by allowing the enzyme to enter the blood stream intact and be carried to every cell in the body in order to be effective. In this way, systemic enzyme therapy can fight inflammation and stimulate the body's own enzymatic processes, decrease pain and swelling, combat free radicals, improve circulation, and bolster immunity.

Systemic enzyme therapy is an integrative, holistic approach to health and healing. When made for systemic use and are to be taken orally (opposed to injection and/or topical application) they are enterically coated or protected in some way so they can pass through the acidic stomach intact. Microbial enzymes can be designed and produced to be acid resistant and, therefore, can resist the low pH of the stomach and pass onto the small intestine to do their work.

There are at least three methods by which enzymes are absorbed into the small intestine:

1. Pynocytosis,
2. Transcellular absorption (persorption) and/or
3. Transported by the lymphatic system.

Complete Book of Enzyme Therapy by Dr. Anthony Cichoke Avery Press, 1999, pages 37–54. Dr. Cichoke says, "Enzyme depletion is one of the greatest tragedies in today's society. If your food has been cooked and/or processed, it is enzyme dead. Fewer than 10% of Americans eat 2 servings of fruit or 3 servings of vegetables a day."

Enzymes are amino acids. They are the structural units of all proteins. There are approximately 20 different amino acids, which occur in each enzyme in different numbers amounts and combinations. The body can make many of these amino acids by itself, but nine of these amino acids, called the essential amino acids, cannot be made by the body and must be obtained from diet and/or supplementation. Further, stress (including disease or injury) may cause increased demand for certain amino acids. They are:

1. Alanine: which can reduce cholesterol (when combined with argine and glycine) effects the stabilization of blood glucose, enhances fat metabolism
2. Arginine: fights hypertension, (according to cardiologist Dr. John Cooke of Stanford, about 9 grams of arginine a day are recommended. To that end he has developed the "Heart Bar"—a medical food containing significant grams of arginine). Additionally, arginine accelerates wound healing, enhances thymus activity, increases fat metabolism, aids insulin production and glucose tolerance.
3. Asparagines: fights chronic fatigue, cirrhosis, and drug addiction.
4. Aspartic acid: plays an important role in metabolism, increases endurance, treats drug addiction, cirrhosis, fatigue.
5. Cystein: promotes healing and improves disease resistance, detoxifies the body.
6. Glutamic acid: Influences brain health, detoxifies body.
7. Glutamine: treats alcoholism, helps maintain gastrointestinal health, prevents malabsorption.
8. Glycene, detoxifies liver, part of glucose tolerance factor.
9. Histidine: needed for tissue growth and repair and blood cell production, treats digestive disorders, arthritis, and allergies.

10. Isoleucine: aids healing from burns.
11. Leucine: aids healing from burns
12. Lysine: fights herpes, aids calcium absorption, tissue repair, and collagen formation, essential for growth in infants, maintains nitrogen equilibrium, and in adults plays a role in enzyme, hormone, and antibody production, treats cold sores.
13. Methionine: helps prevent liver and artery fat build up, maintains blood flow to kidneys, heart, brain, thus helps protect cells from free radicals, detoxifies harmful agents, aids digestion, helps prevent brittle hair, aids muscle weakness, fights osteoporosis and allergies.
14. Phenylalanine: prevents and treats depression, treats hyperactivity and attention deficit disorders, produces neurotransmitters, improves memory, aids weight loss, elevates mood, powerful pain reliever.
15. Proline: needed for formation and maintenance of collagen and healthy skin.
16. Serine: involved in biosynthesis of pyrimidine, purine (uric acid compounds), creatine (a nitrogen compound found mainly in muscle tissue), and porphyrin (organic compounds), forms cystine (an amino acid) with homocystine.
17. Threonine: aids digestion, improves absorption and assimilation of nutrients, important to formation of collagen and elastin, helps control epileptic seizures.
18. Tryptophan: important in energy production, glycolysis (the energy producing process in which sugar is broken down to lactic acid) tissue respiration, and fat synthesis, relieves pain, aids sleep, precursor of niacin and seritonin.
19. Tyrosine: helps form antibodies and nourish blood, treats Parkinson's disease, narcolepsy, and hypertension, a melanin precursor, functions in a synthesis of hormones (tyrosine and epinephrine), and neurotransmitters (norepinephrine, dopamine).
20. Valine: speeds healing from burns, aids normal metabolism, important to muscular coordination, mental energy, and nervous system function.

The inventor envisions one or more amino acids which can be encapsulated solely or in combination with other ingredients with specific release times so that they are complimentary Enzymes are often divided into two groups: systemic and/or metabolic enzymes and digestive enzymes.

Digestive Enzymes

Digestive enzymes are secreted along the gastrointestinal tract and break down foods so that the nutrients are more readily absorbed into the bloodstream for use in various bodily functions. There are three main categories of digestive enzymes: amylase, protease, and lipase. Amylase, found in saliva and in the pancreatic and intestinal juices, breaks down carbohydrates. Different types of amylase break down specific types of sugars. For example lactase breaks down milk sugar (lactose), maltase breaks down malt sugar (maltose), and sucrase breaks down cane and beet sugar (sucrose). Protease, found in the stomach juices, and also in the pancreatic and intestinal juices helps to digest protein. Lipase, found in the stomach and pancreatic juices, also present in fats in foods, aids in fat digestion.

Digestive enzymes are very important on a regular basis. While the body manufactures a supply of enzymes, it can also obtain enzymes from food. Unfortunately, enzymes are extremely sensitive to heat. (Even low to moderate heat (118 degrees F. (48 degrees C.) or above) destroys most enzymes in food, so to obtain enzymes for food one must eat raw foods. Unfortunately, the eating of raw food is not prevalent in out society today. Research has shown that as we grow older, the body's ability to produce enzymes decreases. At the same time, mal-absorption of nutrients, tissue breakdown, and adverse health conditions increase.

The alternative is to take enzyme supplements, which reduce the stress on the body, etc Today digestive enzymes are available over the counter in tablet, liquid, capsule, form.

It is the object of this invention to provide digestive enzymes, separately and/or in combination with each other. If they are micro-encapsulated there is a greater potential for stability and potency. Further they may be combined with other ingredients to compliment such as peppermint which is know to be good for digestion.

Systemic Enzymes

Many people are familiar with enzymes as digestive aids. In addition it is very important to include the systemic enzymes and systemic enzymes in combinations because many enzymes can also be used to treat a wide variety of conditions through systemic enzyme therapy and/or through the aforesaid use of combinations.

Systemic enzymes can be taken in formulations made with any and/or all sorts of dietary supplements such as: phyto-nutrients, vitamins, minerals, herbs, anti-inflammatory agents nutraceuticals, pharmaceuticals, etc. Again, development and combinations rely on the technologies to best deliver, while ensuring stability and bio-availability to the consumer. From the categories just described and mainly those which are considered "nutritive", (especially phyto-nutrients those coming from plants), in combination with systemic enzymes form what is called and have been described as Enzyme Absorption System Enhancers (EASE). These combinations are beneficial as they improve the absorption and bio-availability of other nutrients, maximize enzyme activity when combined with these nutrients, reduce the drain of the bodies own digestive enzymes, etc.

In systemic enzyme therapy, the enzymes are distributed throughout the body to help restore the body to health. Some of the conditions which can be treated with systemic enzyme therapy include; arthritis (and other inflammatory conditions), back pain, premature aging, circulatory problems, herpes, injuries, systemic myofacial pain, multiple sclerosis (MS), skin problems, gynecological problems, lupus, erythematosus, and other auto-immune diseases, viruses, and weight problems.

There is much literature on the aforementioned coming from Germany, Japan, and Italy, along with the U.S. on the use of enzyme therapy. The inventor calls attention to the fact that in addition to new applications, which are being discovered constantly in systemic enzyme therapy, they are being discovered in all categories whereby the delivery system becomes critical.

SUMMARY OF THE INVENTION

The inventor has called attention to the fact that this invention goes in new and novel ways beyond fiber-water, and therefore inventive additional aspects are here forth created/products that are water-like, taste water-like compositions, just like Fiber-Water, but with the addition of the ability to change the viscosity, add encapsulations, particles (flecks, dots, specks and/or the like) emulsify, suspend, create special effects, all with the specific purpose of creating "healthy" while creating visually appealing, "entertaining" water-like fiber-waters (drinks), and/or the like, for general desirability/use, and/or for specific use, dietary use and/or medical use.

Of great importance to the inventor, and is present in all her filings, is that there are sound scientific principle(s) behind the inventiveness, the inventiveness will be consistent, and that the intent of the inventiveness will be available and/or bio-available to the user on a an individual, as well as a "duplicatable" and "replicatable", basis.

With all the dollars spent on all aspects of media today the inventor would be hard pressed to feel she could capture a portion of the market place unless the products are so unique, valuable, and/or distinguishable from what the media is promoting/telling consumers that they should drink.

To this end the inventor, with this invention, is able to combine "healthy" and in many instances added entertainment, especially for children, in the water beverage category. If the process is enjoyable to the consumer/user, as well as healthy, then there is a chance to capture a consumer while making a difference. It is a lofty goal to hope to reduce the number of soft drinks, over-sugared drinks and juices, that are consumed at such a high rate. Although there is hope and sales are beginning to reflect this new trend. To that the inventor is encouraged.

So while this inventor has filed PCT WO 01/70591 Al titled: Infusion Packet with useful and decorative elements, Support Member, and Delivery System she has also filed US CIP of PCT/US01/09171 Method of Hydration, Infusion Packet System(s) Support Member(s), Delivery System(s) and Method(s) with business model(s) and Method(s). Sometimes it is not just the drink, but also the way in which it is presented and/or delivered that carries, along with the drink, just what it takes to capture a consumer by looks, additives, and/or the like.

The inventor here understands what is involved, what it costs a company to launch a new product(s) especially in Ready to Drink (RTD) Form. Such drinks we often predominately select by what is new, considered fashionable, and/or established (a brand) such as a Coke or a Pepsi, Sprite, Mountain Dew, So-Be, Snapple, Mystic, A&W Root Beer, just to name a few.

Drink selections now have bent towards adding ingredients for which the company is hoping that the consumer will select by the effect (stimulating, relaxing) that they promise the user. Mentioned above, and further here, we note waters with caffeine, nicotine, chlorophyll, and a myriad of vitamins, herbs, "other" substances and additives (some considered nutritional) addressing "a feeling" effect are coming to market. Vitamins seem to be a "hot ticket", as if it is even desirable to get your vitamins in a water product.

What the inventor has noticed, so prominently, is that major companies like a Coca Cola, etc. launch different drinks in different parts of the world. It is obvious that certain flavors, "degrees of sweetness" etc. is more popular in certain areas of the world. Sometimes this is due to ethnic preferences. Sometimes certain ingredients are not always and/or readily available, or too costly, especially when desirous to expand to distant regions. This invention hopes to address much of the aforesaid by not really having flavor, but by providing the foundational taste of water, which is accepted worldwide. (Note: Under the guidelines of flavoring water the FDA says it is still water if the flavor constituent is 1% or less).

However, as flavor enhancers in a bottled drink there are other technologies that come to the forefront. The company, Sensations, has impregnated into the plastic sports cap, aromas that align with flavor. U.S. Pat. No. 6,102,224 to Sun, (PepsiCo. (NC), titled: Aroma release cap, whereby a method and apparatus is described, so that when the bottle cap is removed from the bottle, using scratch and sniff material/technology (creating friction), aroma is released. Further PepsiCo also controls the technology to add aroma to the nitrogen in the head-space of the bottle.

Clearly it is the goal of the inventor to bring forth a whole new category of drinking, based on the invention fiber-water called Hydraceuticals™ "Hydration with a Healthy Twist"™.

GENERAL OVERVIEW OF THE INVENTION

Just as the inventor has contemplated new and novel ways to go beyond water with fiber-water, she now is dedicated to using fiber-water as the base for new compositions whereby, creatively, using encapsulations and viscosity modifications as delivery vehicles so as design products targeting "specific desires" and/or "special needs".

These new water compositions will include, but not be limited to compositions addressing, as examples; obesity, diabetes, heart health, improved general health and well being, stress, depression, pain, fostering a healthy digestive tract, and the binding and removing of toxins from the body, thus intending to reduce the incidences of cancer etc. Further looking at immune enhancing, anti-bacterial and anti-viral, compositions. Further looking at products for babies, children, teenagers, seniors, pregnant mothers, stress, athletic and sports needs, all based on one, or a combination of soluble fibers delivered in pure, safe, water. Integrity will be reflected by the choice of systems, how they are integrated, and the additional scientifically researched and developed active ingredients. Manipulating via viscosity changes and encapsulations, mainly, will reflect and affect the results. Most important to the inventor, is how to create within the novelty and newness of this invention, "special added-value Fiber-Waters" for humans and/or animals which may be drunk, used for enteral feedings, and/or spooned.

The inventor realized that for those afflicted with a myriad of health challenges (acute/chronic) there must be an easier answer as to how to deliver target specific ingredients. Recognizing that people by nature are lazy and want convenience and, also by nature, individuals (users) don't take things that are good for them (look at smoking), or if they do it is not on a regular basis. "Taking with regularity" is critical for many supplements, even fiber-water, which a consumer cannot gain the maximum benefit, (although every little bit helps), in just one serving now and then. Individuals procrastinate and there's always an excuse. That is why the inventor chose to use water as the delivery system for the fiber and beyond. Some individuals fear taking pills and capsules, and/or find taking them is somewhat distasteful. Others may have difficulty swallowing. Others find that the ingredients are so strong that they come up on them, as in an acid reflux situation. Another problem is that they look so ugly and distasteful. Then too many ingredients, especially vitamins and minerals, carry an undesirable odor and/or taste. Water is needed by everyone daily to live, fiber to live healthier, and now expanding to service an individual's needs and desires so that not just life span, but health span will increase.

In such cases, for a product to be palatable, manufacturers have resorted to using extra sweeteners, mainly sugar, and/or chemical additives. Regardless of the havoc the sugar plays in the body, all the extra calories alone are a major issue, along with what this sugar does to your teeth. However, sometimes it is necessary to add sweetener, but not to overwhelm. We think of sweeteners as being sugar in one form or another. Sometimes a sweetener (sugar/sugar substitute may be necessary to counteract the use of organic and/or inorganic acids necessary for production of a safe product with extended shelf life. Many new sweeteners have recently come to market and shall be used as deemed appropriate by those skilled in the art. The significance here is that it is not the intention of the inventor to make a sugar loaded product, when in fact it is the direct opposite. It is also factual that great pains will be taken to accomplish the aforesaid.

For some of the drinks proposed, it is essential for the condition that they are targeting to add glucose but that will be done in moderation. It has been so far established the importance of hydration and fiber, and now perhaps glucose in "designed/designated and specific amounts", in accord with achieving maximum benefits appropriate to specific conditions, and including but not limited to other additives.

Using encapsulations and viscosity changes, along with the presentation of additives, may be added to the drink without adding significant taste and/or calories. Ramifications, including but not limited to, preventing sharp rises and fall-offs in blood glucose levels which are known to cause mood swings, depression, cravings, headaches, hyperactivity (especially in children) and, most particularly, significant calories which can lead to weight gain and/or be a precursor for problematic health issues in the future (e.g. diabetes), etc.

Many individuals who need to take supplementation on a regular daily basis might and/or will gain more benefits from taking the additive(s) throughout the day. How many people actually take supplements with them when they leave home for the day? Even if they do they are not always carried appropriately, and/or "go stale" and unclean in a desk drawer at work. AND with what liquid, and do they ingest enough water period, not considering the importance of being sure that a substantial amount of safe water is used to help these supplements travel through the system. Interesting is that the inventor has observed individuals who may take up to ten (10) or more supplements in the morning, and even more when they get home in the evening. Others leave home and forget their necessary and/or desired supplements? When they get home, many times they are pre-occupied, and/or too tired, and/or believe that they shouldn't take certain nutrients in the evening, especially before bedtime.

A commitment of this invention is to avoid unnecessary additives chemicals whenever possible, and most critically, use small amounts of sugar (a durative of, in combination with any form of sweetener) only when necessary and required for specific use. Thus the invention, functional water(s) or water(s) for specific dietary use, and/or medically recognized conditions is designed to be safe, convenient, purposeful, and as ethical as possible in the area of medically sensitive or reactionary effects.

The inventor is presenting a radically new, completely shelf-stable, ready-to-drink totally nutritional functional fiber-water product. Functional fiber-waters for specific use(s) and/or medical use(s) is revolutionary in the realm of the buying public's ability to finally gain access to ethical functional water products designed for the users specific desires, dietary supplementations, and/or medical use, with one or more additives, with a specific intent, along with encapsulations, viscosity changes, and/or both. Not only is fiber-water, and fiber-water extensions, for humans, but also for their pets, some of who may need this product as much, if not more, than their human counterparts.

By providing in addition to safe water and soluble fiber, the addition of various popular, safe and completely approved functional ingredients, a product of exceptional value and versatility is created for consumers. Then by varying that ability, once again, to include various additional elements/components along with one or more functional ingredients, the existing fiber-water invention is enhanced. Then again, the variations offer the basic same product for multiple usages by varying their process conditions, including, but not limited to, viscosity changes and encapsulations. Now in doing all of the above, various such water products can be obtained that specifically target the nutritional and health goals, as well as needs and/or be condition specific as related to health improvement and/or challenges, in both healthy individuals and those needing health improvement in humans, and/or animals.

Diet refers either to the types of foods a person eats or the practices they use to control the types and amounts of food eaten to promote weight control, as to gain or loss, good health, or to help control or reverse disease. A healthy diet contains all the energy, protein, vitamins, minerals, and other essential nutrients, including fiber, and fluids, and most essentially, water, the single most critical ingredient the body needs on a daily basis and cannot do without . . .

The invention (U.S. Pat. No. 6,248,390), fiber-water, is quintessential to the Continuation In Parts (CIP) titled: "Functional Fiber-Waters, Waters for Specific Dietary Use and Medical Use." The word "function" used herein, as described in Webster's Dictionary, means:

1. The kind of action or activity proper to any person or thing;
2. The purpose for which something is designed or exists.
3. It is further denoted to mean, a relation between two or more elements in which one or more elements are assigned to one or more other elements.

While it is conceived that these products be available mainstream in the same bottles and packages that mainstream waters, juices, and sodas are found in, and may be found for purchase in the same locations, it is also conceived that they be packaged differently/accordingly and sold in, or by, medical institutions, and/or establishments. Further they may even be sold under a doctor's request (medical food) and/or by prescription. As just one example Fiber-water, with the additional focus on diet control, is reflected in this present application concerning a water composition, more specifically water and fiber, and encapsulated related ingredients, with or with out a minimal amount of sweetener, designed to assist humans and/or animals with their diet specific needs and goals. There are additives, known by those in the art of weight control, that are not commonly used and/or approved for use except under medical supervision, ergo the correct labeling and product distribution channels will be followed.

Water has a viscosity of 3 centipoises, as opposed to orange juice or milk, which may have centipoises between 50–100. By increasing the viscosity of the fiber-water with a low viscosity fiber (permits using more fiber) along with the gelling qualities of pectin or guar gum, or the addition of one or more other kinds of soluble fiber, gelling agent(s), the fiber-water will gain more substance, which to many users be more appealing, and in some cases, easier to ingest (swallowing problem than a liquid with the viscosity of water itself). It may even be "spoonable". If colored and/or decorated etc. the preparation will have greater consumer appeal yet it is really almost just like water, fiber-water.

While gelatin can be used, carrying with it known specific beneficial properties, (e.g. Knox gelatin by The Nabisco Company, claiming that gelatin provides building blocks for collagen—the chief structural protein in cartilage and bone and also claims to enhance for fingernail strength, it is not without its disadvantages. For example, gelatin is expensive, sets up rather slowly, and water products containing gelatin could be undesirable for some religions, such as Jews and Moslems as it is often manufactured from pig products. In U.S. Pat. No. 5,002,934 to Norton et al., issued Mar. 26, 1991, titled; Aqueous gel comprising carrageenan, it is demonstrated that without the use of gelatin, relatively strong low melting gels can be made.

It is also conceivable that some thickeners may be appropriate by themselves, and/or in combination with gelling agents, so long as they comply with the integrity of the invention. Thickeners include, but are not limited to, propylene glycol alginate, xanthan gum, starch, modified starch, gellan gum and carboxyethyl cellulose. These additives certainly contribute, among other qualities, to a more food-like substance, and can actually be, and/or perceived as being, more filling when ingested.

This inventor, and therefore this invention, will be most sensitive to babies, children, teens, adults, seniors, and those, regardless of age, with specific health desires, challenges, and/or needs.

Compositions with encapsulations, viscosity changes, or both may be packaged in expected bottles (glass or plastic), box, plastic, paper, pouches, and/or the like. The addition of color, flavor, aroma and shape of the product within its specifically designed contained confinement, attractive packaging using target specific graphics, would be most effective for inducing an individual to maintain needed fiber and water (hydration) and additives of value on a daily basis.

This invention can further deliver additional active ingredients, desired and/or needed, so that an individual does not have to take a tablet, capsule, soft-gel, etc., which may create discomfort in swallowing and, separately but additionally, lower the risk of not drinking enough safe water at the same time. Often noted: people will toss back into their mouths handfuls of supplements, and/or medications, sometimes with no water at all, or only enough to allow them to enter the stomach. This practice can be very dangerous in general, and may lead to choking, or other adverse medical conditions.

OBJECT OF THE INVENTION

We have established early on the importance of fiber in addressing many areas of health. Best to review here with examples of specific combination of potential fiber-water compositional product. This, in total is a huge market as we look at the unique selling positions and the loyal consumers who choose to, need to, or both address their health and/or the health of one under their direct care. The inventor is aware that it is most frustrating at best for those who are becoming educated, knowledgeable, and willing, not to have ethical products be made available. One size does not always fit all. It has been estimated that about one in nineteen individuals in our society has a health condition that definitely requires special attention. This is a loyal and dedicated consumer. In many cases this makes the need for adequate fiber and water even more important to these individuals, along with the specific additions, and in the novel delivery methods. Due to modern medicine's success in combating disease, and with a better understanding of aging, and our ability to medically and dietarily address the aforesaid, we are living longer. But can we live healthier? The inventor's goal is to provide those opportunities through safe fresh pure water, and make them ethical as well as attractive in greater hopes that consumers will comply.

1. The object of the invention is to present a fiber-water composition with added encapsulations regardless of size, shape, color, material(s) and/or all and/or the like, simultaneously with hydration.

To present such encapsulations regardless of composition(s) releasing potential(s) capability that will serve to protect sensitive ingredients, direct their release, visible and/or non visible to the eye, yet "swallowable" and/or "spoonable".

2. The object of the invention is to present a fiber-water composition with one, or more than one, viscosity changes, simultaneously with hydration.

3. The object of the invention is to present a fiber water composition employing both encapsulations and viscosity changes, simultaneously with hydration.

4. The object of the invention is to present a fiber-water composition using encapsulations, viscosities, and/or both which move around in the bottle (a lava lamp effect) using such possibilities as the introduction of heat/cold, light/dark, shaking rolling, stirring to create different effects and combinations, simultaneously with hydration. This can be done for delivery purposes and/or entertainment purposes.

5. The object of the invention is to present a fiber water composition that contain particles, flecks, and/or any "descriptive" of the like, that add active substances and/or decorative elements to the product, simultaneously with hydration. The just said may be in suspension and/or settle and move when the bottle is moved in any direction and/or by any means 6. The object of the invention is to present a fiber-water composition with additives in a bottle with a form such as a character, which does not pass through the bottle into the drinkers/"spooners" mouth to be considered dangerous (except if small enough and designed as such {alphabets in alphabet soup}), and/or does not block the opening from drinking and/or pouring of that is the chosen pathway of delivery, simultaneously with hydration.

The objects may be representational, and/or just a shape(s), and/or may be more than one. One might think of a ship in the bottle, or a snow filled paperweight with an affixed character(s) and moving particles surrounding separately and/or simultaneously.

If one considers a "spoonable" product, like a Jello® or a soup then these particles may have meaning like in alphabet soup, or be tiny characters, miniatures, whereby they are not drunk but spooned and possibly chewed, and/or the like.

7. The object of the invention is to present a fiber-water composition that addresses airline travel beyond just the needed water (hydration) and fiber. (Example: deplete in airline foods) with specific anti-oxidants, (mainly A, C, and E) needed to counteract the free radicals in the cabins for flight personnel and passengers a like. Fiber-Water PLUS for Airline travel, simultaneously with hydration.

8. The object of the invention is to present a fiber-water composition with enhanced additives under the guidelines of this invention that is most useful in emergency (stress) situations serviced by such institutions as the Red Cross, FEMA, and/or the like, simultaneously with hydration.

While it is to be noted that there is an enhanced fiber-water for general stress this composition specifically addresses emergency situations.

Besides, universal use as a hydrating and fiber providing material, fortified fiber-water with the additives will be even more helpful as a single product and especially useful in situations of stress. It is believed that stress, both physiologically and psychologically wrecks havoc on the body and alters or effects bowel regularity as well as other bodily functions.

When under stress humans and animals are known to reduce their consumption of water. Yet when the body is stressed by disease, additional water is required, yet this is exactly when many reduce their fluid intake. Further stress may influence people to prefer sugar-laden beverages (comfort food) or caffeine beverages for alertness—these types of beverages actually increase ones water requirement and may lead to dehydration.

Thus, it is beneficial to provide fiber-water and/or the fortified fiberwater(s) (more categorically target specific) as opposed to plain water in emergency supplies to be used in case of natural disaster—fire, flood, storm, earthquake, or hurricane and it is suggested fiber-water be stocked by FEMA or its international counterparts.

During such a disaster people are stressed and are often forced to move from their homes and everyday surroundings. Emergency situations often dictate a shortage of food and water and/or that food and water will be available at abnormal times. This combined with the general shortage of fresh fruits and vegetables, which are a key source of dietary fiber and other important nutrients, during such an emergency naturally impacts health status, animals too.

It is also conceivable as for any part of the invention to have a vial of fortifications to the basic fiberwater and that they may be mixed in. These may present in vials and/or the like. It certainly allows more product versatility to a posing situation. (In the inventors infusion packet filing this is in depth but this is not in dry form but in a liquid vial, packet etc and specifically for the base product fiber-water.

9. The object of the invention is to present a fiberwater composition designed to specifically address digestive support, simultaneously with hydration: Digestive Support FiberWater
   a. The importance of addressing digestive disorders:
      i. The inventor is concerned with the over abundance of degenerative digestive conditions so prevalent in the US. Today, 70 million American suffer from digestive diseases, 15 percent on a daily basis (NIDDK 1997). An even larger population, approximately 118 million, experience heartburn or are afflicted with gastro-esophageal reflux disease (GERD) at least once a month. Even more potentially alarming is the projected 35 percent increase in the number of adults 50–64 who will be afflicted with digestive problems. It is estimated in America that 90 million people use antacids or other stomach relief medicines (Euromonitor, 1998). Next to headaches stomach problems are one of the most self-treated ailments in the U.S. (American Pharmaceutical Assoc., 1997).
      ii. A principal function of the gastrointestinal tract is to process and absorb food. The stomach, which is both a storage and digestive organ, works to optimize the conditions for the digestion and absorption of food in the small intestine. Following the stomach, is the large bowel (colon), then is the small intestine, which comprises three regions: the duodenum, jejunum, and ileum. A major function of the small intestine is one of absorption of digested nutrients.
      iii. The passage of a meal through the, gastrointestinal tract, which leads to digestion and absorption of nutrients, is controlled by a complex system of inhibitory and stimulatory motility mechanisms which are set in motion by the composition of the meal ingested. Specific receptors for fats, and proteins, and the osmolality, acidity and particle size of the meal activate propulsive and inhibitory reactions, which modulate transit and thus absorption. The rate of passage through the small intestine is of great significance for the rate and extent of absorption from the small intestine.
      iv. Disruption of the normal digestive and absorptive processes frequently manifests as a variety of syndromes, such as, for example malnutrition, weight loss, diarrhea, steatorrhea, vitamin deficiency, electrolyte imbalance, and the like.
      v. The small intestine is also an important site for the absorption of pharmacological agents. The proximal part of the small intestine has the greatest capacity for absorption of drugs. Intestinal absorption of drugs is influenced to a great extent by many of the same basic factors that affect the digestion and absorption of nutrients, water and electrolytes.
      vi. While many of the fibers address digestion and improve and support gastrointestinal health the inventor chooses to go beyond their sole ability alone to contribute to better digestion and the improving and/or sustaining a healthy gut.
      vii. Further, one of the strongest health links for nutraceuticals is to treat digestive problems.
      viii. So as to gain a better perspective, and a more layman appreciation of a portion of the invention, the inventor presents a water composition which not only hydrates along with delivering soluble fiber (some fibers are more inclined to benefit good gut health such as inulin/those which act as a pre-biotic/pro-biotic {to be discussed in depth}), but now to enhance with encapsulated ingredients specifically designed to supply additional additives that promote a healthy gut. Additionally also targeted at addressing the symptoms of gastro intestinal upset/indigestion, best in a natural way however pharmaceutically if deemed necessary.
      ix. The inventor has covered digestive and systemic enzymes and their delicate nature, yet important function in the body. There are other ingredients that are known in the art to support digestion and/or aid in indigestion. Those may be encapsulated as well so that the taste may be masked as needed. In the cases of indigestion known helpful additives include, but are not limited to the following: alfalfa, aloe, anise, catnip, chamomile, fennel, fenugreek, goldenseal, ginger, peppermint, hydrochloric acid (sometimes), garlic, B complex especially B1 and B12, L Glutamine, to list just but a few.
      x. Further, by time releasing the encapsulation(s) all at the same time and/or sequencing, be they the same ingredient or different ingredients this will allow the ingredients to be delivered to a specific targeted area of the Gastrointestinal Tract.
      xi. U.S. Pat. No. 5,977,175 to Lin (Cedars-Sinai Medical Center Los Angeles Calif.), issued Nov. 2, 1999, titled: Methods and compositions for improving digestion and absorption in the small intestine. The abstract as follows; "The present invention provides methods and compositions for slowing gastrointestinal transit and prolonging residence time to optimize presentation and absorption of ingested nutrients and/or pharmacologically active agents in the small intestine to prevent and/or reduce ineffectiveness thereof due to mal-absorption. The present invention further provides methods and compositions for enhancing the bio-availability and therapeutic effectiveness of pharmacologically active agents. What Lin points out is critical in relation to soluble fiber which is known to slow transit time through the colon not just to allow the binding of toxins so as to remove them from the colon but to slow the transit time for the absorption of the additive, "drug" and/or the like. Encapsulations and/or viscosity changes in the deliver system may further enhance target specific delivery.

xii. The size as well as the components, perhaps in the form of particles inside of particles then inside of said components, (whether they are considered encapsulations or not) is in the inventiveness here described in this filing (with or with out viscosity changes or not) will depend on many factors and known to those skilled in the art of structuring, composing, and formulation.

xiii. Promoting good gut health U.S. Pat. No. 5,605,697 to Asano (Fujisawa Pharm. C., Ltd. Osaka JP.), issued Feb. 25, 1997, titled: Bifidobacterium growth promotant. Abstrct teaches as follows follows: This invention relates to a bifidobacterium growth promotant comprising gluconic acid, a nontoxic salt thereof and/or glucono-.delta.-lactone as an active ingredient. The bifidobacterium growth promotant of this invention has selective bifidobacterial growth promoting-activity and, at the same time, inhibits growth of deleterious bacteria. Moreover, its rate of digestion and absorption in the upper alimentary tract is so low that the promotant has very satisfactory characteristics as a bifidus factor. Therefore, the bifidobacterium growth promotant of this invention can be used per se or as an additive for various foods and drink to provide functional foods and drinks, thus being of great value from the standpoint of health improvement. This prior art proves the new finding that an organic acid has the activity to promote the growth of bifidobacteria.

xiv. Additionally U.S. Pat. No. 5,698,437 to Masuda, issued Dec. 16, 1997, titled Agent for proliferation of bifidobacterium is noteworthy.

10. The object of the invention is to present a fiberwater composition designed to specifically address overweight (appetite suppression, obesity and/or "dieting"), simultaneously with hydration: Diet Support Fiber-Water a. Fiber-Water composition with enhanced abilities designed to specifically address appetite suppression/weight loss/weight control.

i. First to note is how mind boggling it is to know that literally over a billion dollars annually is spent on pharmaceutical drugs, over the counter supplements (OTC) medications, with their guarded "all natural promises", shakes and herbal concoctions, along with each diet Guru's claim to have the ultimate answer in league with their philosophy of "why" and "how" to lose weight. We are bombarded with presentations everywhere including but not limited to the advertisements on television (infomercials) print advertisements, direct marketing and/or the like, all costing an enormous amount of money to produce. They may also provide the plan by which to accomplish a weight loss goal and, in many instances, have available products under their name produced. (Robert Atkins as one who purports a low carb/no carb diet for weight loss. In fact 35,000,000 Americans are on such diets. Additionally, another 80,000,000 Americans are on some sort of weight loss diet at any one time.

ii. There are organizations worldwide like Weight Watchers, and Jenny Craig along with a domestic chain of about 2,500 locations (US), centers, called Diet Centers.

iii. The inventor is most concerned with "general population obesity", but with a "special" focus on childhood obesity (CO). CO may not just catapult into adult obesity, but set the child up for major health problems later in life, such as: diabetes, heart problems, stress fractures, psychological abuse etc. The biggest rise in childhood obesity has been in the US, but European countries are following the trend. About one in seven children in France, and one in five children in Italy, is now overweight. To understand this problem, and how significant it is the inventor calls attention to the following:

(1) 61 percent of U.S. adults overweight. Dec. 15, 2000.

(2) The condition of being overweight is due to excess body fat. Strictly speaking, the term obesity is used to denote body weight that is 20 percent, or more, over the ideal weight as determined from life insurance company statistics for age, body-type, gender, and height. If a person's weight is not considered normal for his, or her, height and gender, he or she should try to lose weight to improve health. Weight loss of 10 percent of total body weight is associated with improvements in health.

(3) It has been demonstrated that babies who are fed excessive amounts of food become fat, often remain overweight into adulthood.

(4) Further many babies, children, and/or adults have been given food to feel better, or told that if they want to feel better they should eat more, and the inventor says "notice" EAT MORE NOT DRINK MORE.

(5) Obesity has contributed greatly to one of the major health challenges today in humans and animals, weight control including weight loss, reduction of obesity, and weight maintenance.

(6) This inventor is concerned with the many potentially serious health hazards in being overweight, as mentioned and also includes looking at the potential for being at greater risk for coronary thrombosis and stroke because of arteriosclerosis. Such high-risk people are more likely to develop diabetes mellitus and high blood pressure or hurt themselves seriously in accidents, develop osteoarthritis, particularly of the knees hips, and ankles, and have complications following surgery, such as venous thrombosis and chest infections.

(7) Obesity increases the risk of diabetes and cardiovascular disease and causes severe social and psychological problems in millions of Americans.

iv. Therefore it is the belief, and goal, of the inventor to use an easy to administer effective "obesity addressing solution" (fiber-water {U.S. Pat. No. 6,248,390} addresses this problem), and now by this addition to the just said invention the inventor, will provide enhancement(s) for this purpose thus allowing more versatility to the treatment with the delivery systems of encapsulations and viscosity changing abilities, independent and/or in consort).

v. While psychological factors may, or may not, play an important role in gaining and/or loosing weight, they must be considered as well. There has become a tremendous focus on oral gratification as a part of addressing this issue. For many they just need to have "their mouth going". It is even noted that when smokers give up smoking they put on weight. Drug addicts go to smoking and/or eating. However, it is well established that although disciplinary dieting may result in weight loss, such loss is rarely long lasting due to hunger, or more so to the "drive to eat". This drive may be accompanied by the need for oral gratification. In the beginning a mother's breast, or the bottle, gave us nourishment, oral gratification, and satisfaction. By providing a functional water, or functional water program, especially for those addressing the problem of weight loss and/or weight maintenance, it is possible to also address this need for oral gratification.
  (1) With that in mind it is not just the additives to the fiber-water via the methodologies described, but the very fact that the dieter is given something that is pleasing, while playing to, and ergo appealing to this "oral gratification needy population".
  (2) A slightly thicker viscosity, which basically goes un-noticed, or slightly noticed, or very noticeable as planned, is one way. Who would want to drink, and/or spoon thick water . . . perhaps one would say "yuck". But it is here that the inventor cannot emphasize enough that, and covered in her issued fiber-water patent U.S. Pat. No. 6,248,390, fiber-water, and now this novel enhanced fiber water, is also used for imbibing and reconstituting other products. Direct quotation for the abstract is as follows: "A shelf stable, ready to use, essentially tasteless and odorless water-like fluid for humans/animals comprised of safe water and a significant quantity of one or more water-soluble dietary fibers. Fiber-water, is intended to be consumed by drinking, or by enteral feeding alone, and/or in combination. The inventive liquid may be consumed directly hot or cold or after use, at any required temperature, in the preparation/reconstitution of beverages or liquid food product (e.g. coffee, tea, concentrates such as "HAWAIIAN PUNCH.RTM.", frozen concentrates such as lemonade/orange juice, soups and pet food). It can be used to enrich foods with soluble fiber through cooking, moistening, reconstituting or imbibing dried foods (e.g. oatmeal, rice, dried fruits, powdered soups, powdered beverages, powdered milks, nutritional shakes, "GATORADE.RTM./TANG.RTM./KOOL-AID.RTM." products, gelatins, custards, puddings, and pet food). Fiber-Water can be consumed in the frozen state either indirectly by adding it to a beverage as a cube or crushed "ice", or directly by licking a frozen "POPSICLE.RTM." product). Fiber-water is safe water fiber enriched intending to be a replacement and/or adjunct to other water to ensure proper hydration while at the same time provide significant soluble fiber."
  (3) So in addition to the formula(s) for addressing obesity, additional fiber-water formulas might not just be supportive but necessary. Categorically, an example would be a stress reducing formula, a mood improver, an anti-depressant, and/or the like.
  (4) U.S. Pat. No. 6,013,622 to Bruno et al. (Nutriceutical Technology Corporation (Bridgewater, N.J.); Research Foundation of State University of New York (Stony Brook, N.Y.), issued Jan. 11, 2000, titled Method of regulating appetite and metabolism
  (5) U.S. Pat. No. 4,784,861 to Gori (CCA Indust. Inc. (East Rutherford, N.J.), issued Nov. 18, 1988, titled: Weight-control formulation, which additionally goes extensively into the benefits of fibers.
  (6) By helping control appetite we now may have discovered a way to address and control childhood and adult obesity as disclosed in U.S. Pat. No. 5,505,981 Method for Imparting Ability of Preventing Obesity and Imparting Glucose Tolerance to Foods and Sugar Preparations Exhibiting Such Preventative Effects.

vi. By designing a plan of action to sip, and/or at the other extreme spoon fiber-water, an enhanced functional fiber-water(s) throughout a protracted period of time, there exists the likely hood that the dieting individual will have something to hold (keeping roaming hands free from selecting food) and additionally, something addressing oral gratification. This is separate from the actual effect of the contents upon the individual, which again, used frequently throughout the day, brings forth additional merit. In many instances the additional functional ingredients may work better in a constant delivery mode, as opposed to a "bolus" dose taken hours apart and/or skipped in par, and/or even forgotten.
  While it is a separate subject, the inventor is most sensitive to those with eating disorders.
  It may benefit individuals with such known eating disorders as anorexia or bulimia since these individuals typically drink water because it fills them up without providing calories.
  Hopefully by these additions to Fiber-water they would serve to not only help preserve proper functioning of the gastrointestinal tract while other treatment is hopefully undertaken, but additionally add other needed nutrients.

vii. Those with eating disorders often from sever dehydration and/or are constantly drink water to ameliorate the hunger pains and satisfy. If in any conceivable way the practice of this invention addresses this disorder by providing hydration, nutrition, even if not providing the calories needed, it is still a step towards improvement, and should be taken as serious, and valuable.

viii. The inventor has looked closely at the following, and is hopeful that with not just these waters in this invention, but with her infusion packets in PCT/US01/09171 and/or her infusion packets in formulation with Fiber-Water (U.S. Pat. No. 6,248,390) and/or these new and novel "consistency regulated" invented waters, with or without the encapsulated additives, will tend towards making a significant impact on the health of our population in general, and especially with our younger.

(1) To the inventor the following should drive home the importance of this invention, along with, perhaps even more alarming statistics and findings:
  (a) Obesity rates have risen in tandem with soft-drink consumption. (The National Institutes of Health recommends that people who are trying to lose or control their weight should drink water instead of soft drinks with sugar).

The Problematical Increased Prevalence of Sugar in the American Diet

The big food companies and fast food chains still produce beverages and food products with an enormous amount of sugars, and most of all soda pop adds unnecessary, non-nutritious calories to the diet.

In fact America is drowning in sugar.

WASHINGTON—The Center for Science in the Public Interest (CSPI) and dozens of leading health experts and/ organizations today petitioned the Food and Drug Administration (FDA) to require that food labels declare how much sugar is added to soft drinks, ice cream, and other foods.

The petition also asks the FDA to set a maximum recommended daily intake (Daily Value) for added sugars and require labels to disclose the percentage of the Daily Value a food provides.

Michael Jacobson, executive director of CSPI, said today at a Washington press conference, "Sugar consumption has been going through the roof. It has increased by 28% percent since 1983, fueling the soaring obesity rates and other health problems. It's vital that the FDA require labels that would enable consumers to monitor—and reduce—their sugar intake."

Marion Nestle, chair of the Department of Nutrition and Food Studies at New York University, said, "Because sugary foods often replace more healthful foods, diets high in sugar are almost certainly contributing to osteoporosis, cancer, and heart disease. It's high time that the food label informed consumers of a food's contribution to a recommended limit for added sugars." Nestle was managing editor of the 1988 Surgeon General's Report on Diet and Health.

United States Department of Agriculture (USDA) surveys show that sugar consumption has increased almost every year since 1982. Most of that sugar came from cane and beet sugar and corn syrup and corn sugar. Much of the increase was due to the consumption of soft drinks.

"Health officials must take prudent action to stem the dilution of the American diet with sugar's empty calories. Declaring on food labels the amount of added sugars would help consumers cut the sugar and improve their diets," said Mohammad Akhter, the executive director of the American Public Health Association.

USDA advises people who eat a 2,000-calorie healthful diet to try to limit themselves to about 10 teaspoons of added sugars per day. In fact, the average American does not eat a healthful diet, but consumes 20 teaspoons of added sugars per day.

A teenage male who eats a healthful diet could eat about 18 teaspoons of added sugars, according to USDA. Most teenage males do not eat a healthful diet, because they consume an average of 34 teaspoons of sugar per day.

CSPI is asking the FDA to adopt USDA's figure of 10 teaspoons (40 grams) as the Daily Value for added sugars. Daily Values are used on Nutrition Facts labels to indicate the recommended maximum intakes of fat, sodium, and other nutrients.

Many individual foods provide large fractions of the USDA's Re-commended sugar limits. For instance, a typical cup of fruit yogurt provide 70% of a day's worth of added sugar; a cup of regular ice-cream provide 60%, a 12-ounce COLA provides 103%, a large McDonald's Shake 120 percent, a large Mr. Misty Slush at Dairy Queen 280%.

One of the biggest problems with high-sugar foods is that they are replacing more foods that are healthful. According to USDA data, people who eat diets high in sugar get less calcium, fiber, foliate, vitamin A, vitamin C, vitamin E, zinc, magnesium, iron, and other nutrients. They also consume fewer fruits and vegetables.

"If you're drinking soda pop instead of low fat milk or orange juice, or eating a candy bar instead of a piece of fruit, you're missing a chance to cut your risk of osteoporosis, cancer, or heart disease," said Bonnie Liebman, CSPI nutrition director.

Liquid Candy, as soft drink are called are harming America's Health. The inventor also believes that all the sugar laden new age beverages such as the So Be Drink line and many of the flavored teas, botanicals, and the like are just as guilty as the soft drinks. Granted they do not have the phosphoric acid of the colas but the sugar level is just as high if not higher.

In 1997, Americans spent over $54 billion on soft drinks. The industry produced 14 billion gallons of soft drinks, twice as much as in 1974. That is the equivalent to 576, 12-ounce servings per year, or 1.6 12-ounce cans per day for every man, woman, and child.

12- to 19-year-old boys who consume soda pop drink an average of 2 12-ounce sodas per day (868 cans per year). Girls drink about one-fourth less.

Bigger serving sizes spur consumption. In the 1950s, Coca-Cola sold only a 6½-ounce bottle. That grew into the 12-ounce can, which is now being supplanted by 20-ounce bottles ( . . . and then there's 7-Eleven's 64-ounce 600-calorie Double Gulp—the "Pop Belly Special").

Soda pop is Americans' single biggest source of refined sugars, providing the average person with one-third of all sugar. Twelve- to 19-year-old boys get 44% of their 34 teaspoons of sugar a day from soft drinks. Girls get 40% of their 24 teaspoons of sugar from soda. Because some people drink little soda pop, the percentages are higher among actual drinkers.

Soft drinks provide the average 12- to 19-year-old male with about 15 teaspoons of sugar a day and the average female with about 10 teaspoons a day.

In 12- to 19-year-olds, soft drinks provide 9% of boys' calories and 8% of girls' calories. Those percentages are triple (boys) or double (girls) what they were in 1977–78. Those figures include teens, which consumed little or no soda pop.

As teens have doubled, or tripled their consumption of soft drinks, they drank 40% less milk. Twenty years ago, boys consumed twice as much milk as soft drinks, and girls consumed 50% more milk than soft drinks. Now, boys and girls, consume twice as much soda pop as milk.

Teenage girls consume only 60% of the recommended amount of calcium, with soda-pop drinkers consuming almost one-fifth less calcium than non-drinkers. It is crucial for females in their teens and twenties to build up bone mass to reduce the risk of osteoporosis later in life. Preliminary research suggests that drinking soda pop, instead of milk, can contribute to broken bones in children and adolescents.

Among frequent consumers, regular soft drinks promote tooth decay because they bathe the teeth with sugar-water for long periods of time.

Diets high in carbohydrate may promote heart disease in "insulin resistant" people by raising triglyceride levels in blood. Sugar, such as that in soda pop, has a greater effect than other carbohydrates.

Soft drinks may increase the recurrence of kidney stones. The National Institute of Diabetes and Digestive and kidney Diseases (NIDDK) includes cola beverages on a list of foods that doctors may advise patients to avoid.

Nutritional Harm of Soft Drinks

Heavy soft-drink consumption also correlated with low intake of magnesium, ascorbic acid, riboflavin, and vitamin A. Calcium continued to be a special problem for female soft-drink consumers.

Dietary surveys of teenagers found that in 1996:

Only 34% of boys and 33% of girls consumed the number of servings of vegetables recommended by USDA's Food Pyramid.

Only 11% of boys and 16% of girls consumed the recommended amount of fruit.

Only 29% of boys and 10% of girls consumed the recommended amount of dairy foods.

Most boys and girls did not meet the recommended amounts of grain and protein foods.

Those surveys also found that few 12- to 19-year-olds consumed recommended amounts of certain nutrients, including:

calcium: only 36% of boys and 14% of girls consumed 100% of the Recommended Dietary Allowance (RDA).

vitamin A: only 36% of boys and 31% of girls consumed 100% of the RDA.

magnesium: only 34% of boys and 18% of girls consumed 100% of the RDA.

Colas provide male teens in the 90th-percentile of soft-drink consumption with as much caffeine as is in 1½ cups of coffee; for females the figure is one cup. Caffeine, a mildly addictive stimulant drug, is added to most Colas, Dr Pepper, some orange sodas, and other soft drinks. Caffeine's addictiveness may be one reason why six of the seven most popular soft drinks contain caffeine. However the inventor notes that caffeine has specific use, and may be used with specific intentions and not just put into beverages, indiscriminately to addict consumers to their product. Caffeine does not contribute to the taste factor in the inventor's opinion and presents, in fact as bitter.

The artificial sweetener saccharin, which is now used only in a few brands, has been linked in human studies to urinary-bladder cancer and in animal studies to cancers of the bladder and other organs. Several cancer experts have questioned the safety of acesulfame-K, which is used in the new Pepsi One.

ix. It is the object of this invention to present additional benefits to fiber-water, which in and of itself, by the nature of soluble fiber(s) addresses appetite suppression/feeling of fullness, ergo weight control and/or dieting while simultaneously satisfying hydration requirements especially important to dieters.

x. In weight loss, weight management, or weight maintenance, diet fiber-water(s) would be water providing adequate hydration, adequate fiber, and perhaps, a minimal amount of a "sugar" and/or a sweetener, and/or a combination of both. The glucose/sugar/sweetener would be for the purpose of modulating glucose levels wherein significant fluctuations in blood sugar can now be kept at bay. In other words, "take the edge off of hunger". Certainly when ones blood sugar falls the symptoms including, but not limited to, extreme hunger, ergo most likely results in overeating and/or food bingeing. (The inventor here is not referring to those who eat for psychological reasons)

xi. A minimal amount of glucose added to the fiber in water is valuable and even to be considered necessary for many reasons, including, but not limited to, a feeling of satisfaction when ingesting/digesting, in helping to support/regulate blood glucose levels during a weight loss, or maintenance program. Also to aid with feelings of depression, stress (a hint of sweet brings satisfaction), and to ensure that, as in fiber-water, adequate water and fiber are consumed. By varying the ratios of both caloric (to accomplish the aforesaid), low caloric, and non-caloric sweeteners, the inventor provides "formulation room" to effect taste and therefore relating affirmatively to the consumer's, perceived and/ or actual, satisfaction.

xii. Further, to maintain a functional water-like drink with very low inclusion of glucose it is necessary to take into consideration the taste of the additional ingredients. It is to this end that encapsulations be included following the guidelines of this invention and the abilities of the art. The viscosity, and/or more than one viscosity, as mentioned, of the fiber-water-glucose/sweetener composition may be altered to better support the desired response(s), with or without encapsulations, or for other commonly known reasons, including but not limited to individuals with swallowing difficulties.

xiii. A swallowing disorder may be caused by allergies, anxiety, bacterial infection, cancer of the esophagus, fear, genetic problems, goiter, hiatial hernia, hormone imbalance, nervous disorder, stress, swollen lymph nodes, thyroid disorder, tonsillitis etc. Further, Jello® like beverages have a great appeal to children and even the elderly as they enjoy the texture and possibility of flavors and colors. A thickening and/or gelling agent to give an enhanced body to the water for the purpose of creating a more food like or filing feeling' is especially desired by those on a weight loss program. Some of these thickening agents and/or gelatins have, by their intrinsic nature, nutritional value. Knox® gelatin by Nabisco® was mentioned earlier but to note that, in addition to fingernails, gelatin provides building blocks for collagen, the chief structural protein in bone and cartilage.

xiv. The present inventor is concerned with providing a composition that can be extremely beneficial to humans (animals too) who are looking to reduce their weight. Then at formulating a plan as to how to implement that plan, including but not limited to the selection of a "functional water" specially deigned to meet the needs and desires. This may readily be a platform for a daily individual, (large container/bottle of one litter or more in contents) to be drunk throughout the day and/or an integrated, multi-bottled/ packaged (Two (2) or more containers synergistically functioning in consort) water program. This is also for those who have already started a weight loss program and/or wish to maintain life long regimen of healthy drinking. It is believed that plus or minus 1–5 gr. of sugar (dextrose, sucrose, fructose etc.) will only add 4 calories per gram to the liquid, in this case 8 oz. (240 ml.). Therefore a total of plus or minus 4 to 20 calories per 8 oz. is what is considered reasonable, but may exceed by design. (Sugar is often referred to as in Brix. One degree Brix is equal to 1% sugar solution per 100 ml.)

xv. With the further addition of flavoring(s), aroma(s), and coloring(s), a diet-fiber-water that includes scientifically studied additives for this specific use, is considered far more ethical than drink selections consisting of water and sugar laden liquid diet supplements that add far too many calories, for one thing, and actually contribute to one, or more than one, potentially serious dietary problems, rather than alleviate them. (The inventor, personally, does not advocate nutritionally fortified diet beverages for continued use, as one must eat meals and regulate the body normally accordingly) However if it is in dry form, to be reconstituted, then with this invention it may be meritorious.

xvi. With the proper administration of a fiber, water, glucose/sweetener composition consumed throughout the day, and on a daily basis, positive results have been observed noting a sufficient reduction in appetite along with and a more regulated/even metabolism.

xvi. U.S. Pat. No. 5,344,824 to Ohkuma et al., issued Sep. 6, 1994, titled; Method for reducing insulin secretion . . . A method for reducing insulin secretion without negatively affecting/influencing blood glucose levels in an animal Abstract: A food composite for saving insulin secretion comprising a refined product of pyrodextrin obtained as an active ingredient through a process of decomposing starch or starch hydrolyzate by heating in the presence of an acid or without acid.

xviii. U.S. Pat. No. 5,505,981 to Wakabayashi et al., issued Apr. 9, 1996 titled; Method for imparting ability of preventing obesity and impaired glucose tolerance to foods and food sugar preparations exhibiting such preventative effects.

xix. It is the goal of this invention to provide the vehicles/delivery system relating to the placement of additives in order to produce a most scientific and ethical product, while giving the consumer the highest in quality, consistency, appeal, and value.

xx. While this invention purports that the addition of said functional components will reside within the encapsulations, it is also conceived that one or more than one of the non-active/active components, in addition to the fiber, will reside in the liquid itself, outside of the encapsulations. The value in doing the aforementioned is multi-purposeful. As an example some minerals might enhance the flavor of the water regardless of the total dissolved solids and/or salts but for a certain specific need, more of that mineral might be needed. If put in the "general water" aka "background water" the taste would not be acceptable, ergo encapsulating that mineral would allow more to be delivered without changing the taste. In the case of Astroade, (Dr. John Greenleaf NASA), the re-hydration drink of the astronauts, which is very high in sodium, this could provide a viable solution. Further, some of the (in this example) minerals could be timed release while some could be used immediately upon ingestion. In the case of some minerals as an example, the water composition would still taste like water (even if you went into a higher mineral category [above a TDA of 500]) and the minerals will enhance the taste and provide nutritive value as well. Note: The inventor has already discussed fiber (including but not limited to the gums) as in relation to what she would define as a "more textured" water composition.

xxi. It is also a part of this invention in total, and not just for the fiber-water for weight loss purposes, that the encapsulations/micro-encapsulations while they may be released in the mouth, they may also be coated to drop within 60–240 minutes, (1–4 hours) post ingestion, thus allowing the active ingredients to be placed farther down along the gastrointestinal tract. In the case of a diet fiberwater, ingredients known in the art to ameliorate hunger and/or give a feeling of fullness ergo having extra value if they are not just immediately released but released at timed intervals. Qualities of mood regulating waters, stress addressing waters, relaxing waters, etc. may be incorporated into the program in the same packages container and/or multiple containers packaged together and/or selected by the choice of the consumer.

xxii. It is even possible to encapsulate small amounts of sugar(s) to be released in this fashion, however they would be larger in size and most likely visible to the eye (perhaps even colorful) that could address fluctuations in blood sugar levels ergo would help ameliorate mood swings, hunger, and/or the like conditions resulting from blood sugar "lows" with or without other additives which have been recognized/endorsed/prescribed by health care professionals and supporting science has validated.

xxiii. Other additives, which are contemplated by the inventor have been well researched with sound ethical, and recognizable, scientific studies behind them and deemed "functional" and known to support weight loss without side effects include but are not limited to:
  (1) Chromium Picolinate reduces sugar cravings by stabilizing the metabolism of simple carbohydrates.
  (2) Vitamin C necessary for glandular function, speeds up a slow metabolism.
  (3) Choline and insitol help the body burn fat.
  (4) Gamma-aminobutyric acid (GABA) suppresses cravings and has antidipressant qualities.
  (5) L. Arginine, L'Ornithine plus L'Lysine are amino acids which are known to decrease body fat and best combined with 50 mg. B6 and 100 mg. Vitamin C for better absorption.
  (6) L'Carnitine has the ability to break up fat deposits and aids in weight loss.
  (7) L'Glutamnine lessens carbohydrate cravings.
  (8) L'Phenylalanine is an appetite suppressant which tells your brain that you are not hungry
  (9) L'Tyrosine suppresses cravings and has anti-depressant qualities
  (10) Zinc enhances the effectiveness of insulin and boosts immune function.

xxiv. U.S. Pat. No. 6,403,657 to Hinz, issued Jun. 11, 2002, titled: Comprehensive pharmacologic therapy for treatment of obesity abstracts the following: The comprehensive pharmacologic therapy for treatment of obesity is a procedure which involves the administration of a desired therapeutic range of Diethylpropion and/or Phentermine in combination with a SSRI medication and nutritional supplementation for brief and long durations which may be 12 months or more. The preferred procedure involves the administration of drugs in combination which are identified as: Citalopram (Celexa) and Phentermine; Citalopram (Celexa) and Diethylpropion; Citalopram (Celexa), Phentermine, and Diethylpropion. In addition nutritional supplementation such as a multivitamin, 5-Hydroxytryptophan, vitamin B6, vitamin C, Tyrosine, Calcium, and Lysine may be used to enhance the performance of the weight loss treatment program. (The inventor here is specifically interested in the encapsulations of the nutritional supplementation of the aforesaid).

11. The object of the invention is to present a fiber-water composition designed to support heart health, simultaneously with hydration: Hearth Healthy Fiber-Water.
  a. If one has elevated cholesterol, for which statistics have shown one (1) in every five (5) adults has, fiber-water (U.S. Pat. No. 6,148,390) with its inclusion of significant soluble fiber has been shown to be of great benefit in lowering such an elevated level.

i. Studies also show that adequate fiber clearly lowers the risk of heart disease and tends to bind toxins, including toxic metals, allowing them to exit safely from the digestive system.

ii. Further, and of major significance, is that in the case of fats the fiber seems to help prevent damaging levels of cholesterol in the blood. This seems to be due to a binding of bile salts and cholesterol to the fiber so that these materials are excreted with the feces, rather than being absorbed or reabsorbed.

iii. Additionally, if we address a way of lowering cholesterol, in addition to soluble fiber/fiber-water as a way to reduce cholesterol level, some natural additions should be considered, and presented within the confines of the "new and novel" of this invention. In the same alternative one can give consideration to a pharmaceutical addition, but the inventor here prefers to use nutritional enhancing additives where ever and when ever possible due to many of the consequences that go with pharmaceuticals. Such nutritive enhancing agents include but are not limited to the following:

(1) Coenzyme Q10, which has been shown to oxygenate heart tissue.

(2) Calcium and magnesium are important in the proper functioning of the cardiac muscle (The inventor is impressed with the magnesium gluconate and the calcium lactate gluconate both by Glucona America, (Janesvile Wis.). They go readily into solution without imparting a taste at recommended levels. It is therefore possible that they can go into fiber-water (U.S. Pat. No. 6,248, 390) and fall within the limits of that patent (TDS). In this filing they do not have to be encapsulated and may reside in the foundational liquid itself, with or without a viscosity change. (Note; If additional palatable and/or non-palatable, water soluble or non-soluble forms of calciums and/or magnesiums are used they will have to be encapsulated most probably . . . Again referencing a previous example "if a significantly higher amount is needed, an amount is best delivered in time release fashion, and/or whereby taste becomes an important factor encaspsulations are a consideration".

(3) Garlic (now exists the odorless varieties) lower blood pressure and thins the blood.

(4) Vitamin E (water soluble by Hoffman La Roche, C H) does not affect the taste of water, and may be used in the basic fiberwater (U.S. Pat. No. 6,248, 390) itself without changing the taste of the composition. Vitamin E strengthens the heart muscle, improves circulation, it is also an anti-oxidant (5) Niacin, lowers cholesterol and improves circulation.

(6) L'Carnatine has been shown to reduce fat and triglycerate levels in the blood. Increases oxygen uptake and stress tolerance.

(7) Additionally, in therapeutic doses potassium, selenium, lecithin, Superoxide dismutase (SOD), taurine, Melatonin, and all the B vitamins are just some of the nutrients that affect the heart in a positive way if used properly.8.The object of the invention is to present a fiber-water composition designed specifically for diabetics. In the case of simple sugars, slowed absorption translates to a more gradual rise in blood sugar following eating. This is important in the managing of diabetes and may also help prevent adult onset diabetes.

iv. U.S. Pat. No. 5,612,026 to Diehl, (P&G Co. Cincinnatti, Ohio), issued Mar. 18, 1997, tided: Cholesterol lowering drink-mix compositions. In this patent a gum, specifically xanthin gum, is used as the cholesterol lowering agent/gum. (Xanthan Gum Xanthan gum is a polysaccharide gum produce by the bacterium Xathomonas compestris. Xanthan gum is a cream-colored, free-flowing, odorless powder, which dissolves in water to provide highly viscous solutions at low concentrations. The Merck Index, Tenth Edition, published by Merck & Co., No. 9868, (1983). Xanthan gum is available commercially under the tradename Keltrol.RTM., by the Kelco Division of Monsanto & Co., San Diego Calif.) The art teaches that: a drink mix composition comprising a therapeutically effective dose of an anion exchange resin; from about 0.05 g to about 1.25 g of xanthan gum; and from about 0.3 g to about 1.75 g of edible, water soluble salt at a level (wherein the gelation rate of the drink mix composition in an aqueous solution is reduced; and wherein further the compositions are in a form mixable with a liquid to form a suspension of the anion exchange resin, xanthan gum and edible, water soluble salt) has a positive effect on cholesterol lowering.

12. The object of the invention is to present a fiber-water composition designed especially for diabetics, simultaneously with hydration: Fiber-Water for Diabetics a. Obesity is a major cause of a dramatic rise in diabetes. Perhaps because of widespread obesity in the US, diabetes has increased dramatically over the past decade, a new nationwide study has found. Between 1990 and 1998, diabetes increased by 70% among individuals aged 30 to 39, by 40% among those aged 40 to 49, and by 31% among those aged 50 to 59, the findings indicate. Diabetes increased across all regions, demographic groups and nearly all states, according to the researchers.

b. It has been discovered that dietary fiber appears to moderate the rate at which sugars and fats are absorbed from the intestine, thus providing the ability to stabilize the blood sugar. This stabilization is extremely valuable to those hoping to achieve and maintain weight loss.

c. U.S. Pat. No. 5,505,981 is an invention, which presents to a method for the ability of preventing obesity and impaired glucose tolerance to ingested foods and preparation exhibiting such preventative effects. There have been developed various agents for inhibiting an increase in the blood-sugar levels and excess insulin-secretion for preventing healthy people from suffering from obesity and/or diabetes or for treating patients requiring the control of blood sugar level such as those suffering from diabetes. As such agents, there have been known, for instance, Acarbose (available from Bayer Yakuhi Ltd.) and AO-128 (available from Takeda Chemical Industries Ltd.) which are substances having an effect of inhibiting the gastrointestinal absorption of sugar and starch and inhibitors for enzymes involved in digestion, however, both of them are medicines and the ingestion or intake thereof for the preventive purpose becomes a cause of various problems. For instance, they suffer from a problem of safety, since they would be dangerous because of possible side effects, including, but not limited to, elongating coagulation time. The invention of said patent teaches us that the prevention of obesity and impaired glucose tolerance can be insured through the inhibition of increases in blood sugar level and insulin-secretion in response to the oral ingestion of sugary substances such as sugars and starches. The inventors of this invention have demonstrated to us that indigestible dextrin is excellent for this purpose. The dosage give would be 1 g to 30 gr. per unit of food of 8 oz. to 12 oz. Therefore for this purpose we would adapt that range.

d. A study conducted and reported in the New England Journal of Medicine, May, 2000 encourages all type 2 Diabetics to have at least 50 grams of fiber a day.

e. Critically important may be the effect of fiber-water(s) on both type one, type two (adult onset and juvenile) and/or borderline diabetics as disclosed in U.S. Pat. No. 5,344,824, titled: Method for Reducing Insulin Secretion.

f. Beside reducing obesity these additives are helpful additives for diabetics:
  i. L'Carnitine which mobilizes fat
  ii. Chromium Picolonate which improves insulin's efficiency which lowers blood sugar levels
  iii. Taurine aids in the release of insulin
  iv. All the B vitamins, along with Vitamins A, C, and E.
  v. Calcium for Ph balance
  vi. Magnesium important for Ph balance and enzyme systems
  vi. Maganese is needed for repair of the pancreas. Also a co-factor in key enzymes of glucose metabolism
  viii. Garlic stabilizes blood sugar
  ix. Alpha lipoic acid: A powerful anti-oxidant has been shown to improve diabetic neuropathy and to improve insulin sensitivity. (600 mg. One to three times as day)
  x. Brewers Yeast (BY) As far back as 1853, reported yet still today that chromium rich BY can be useful (9 grams per day)
  xi. Evening Primrose Oil, improve nerve function and relieve pain symptoms.

13. The object of the invention is to present a fiber-water composition designed to support bone and/or joint health, simultaneously with hydration: Bone and/or Joint Supporting Fiber-Water.
  a. Osteoporosis is a progressive disease in which the bones gradually become weaker and weaker, causing changes in posture and making the individual more susceptible to bone fractures. Osteoporosis is an age related condition that causes a loss of bone mass and increased brittleness in the remaining bone tissue. Osteoporosis currently affects 25 million Americans. Osteoporosis affects 15–20 million Americans and in people over the age of 50 it is linked to 1.5 million fractures a year. The cost of this disease is thought to surpass $18 billion a year and is on the rise. The older you are, the greater your risk. Bone mass—the amount of mineral in the bone begins to become less dense as you age.
  b. Because of the physiological, nutritional, and hormonal differences between males and females, osteoporosis primarily affects women. Also women are at a greater risk also because women have less bone tissue and lose bone more rapidly because of the changes associated with hormones/menopause. Caucasian and Asian women are even more prone to the disease. Small-boned, thin women are also at increased risk. Lifestyle plays an important role as well. Smoking, excessive consumption of alcohol, inadequate consumption of calcium, and little, or no, weight bearing exercise increases risk. The National Osteoporosis Foundation (NOF recommends 1000 mg of calcium a day for men and pre/postmenopausal women taking ERT, and 1500 mg a day for post-menopausal women not on Hormone/estrogen replacement therapy (ERT) and for all men and women over age 65.
  c. Bone is subject to constant breakdown and resynthesis in a complex process mediated by osteoblasts, which produce new bone, and osteoclasts, which destroy bone. The activities of these cells are regulated by a large number of cytokines and growth factors, many of which have now been identified and cloned.
  d. There is a plethora of conditions, which are characterized by the need to enhance bone formation. Perhaps the most obvious is the case of bone fractures, where it would be desirable to stimulate bone growth and to hasten and complete bone repair. Agents that enhance bone formation would also be useful in facial reconstruction procedures.
  e. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis.
  f. U.S. Pat. No. 6,410,521 to Mundy, et al. (OsteoScreen, Inc., San Antonio, Tex.), issued Jun. 25, 2002, titled: Nutritional supplements for stimulating bone growth This art presents a food or food supplement which comprises a compound that enhances bone growth in vertebrates wherein the food or foodstuff is formulated so as to provide the desired bone growth enhancing effect using red yeast rice. The ultimate goal of the methods and compositions of the invention is to treat or ameliorate bone disorders in vertebrate subjects, particularly mammals, and more particularly humans.
     As used herein, "treat" or "treatment" include a postponement of development of bone deficit symptoms and/or a reduction in the severity of such symptoms that will or are expected to develop. The terms further include ameliorating existing bone or cartilage deficit symptoms, preventing additional symptoms, ameliorating or preventing the underlying metabolic causes of symptoms, preventing or reversing bone resorption and/or encouraging bone growth. Thus, the terms denote that a beneficial result has been conferred on a vertebrate subject with a cartilage, bone or skeletal deficit, or with the potential to develop such deficit. By "bone deficit" is meant an imbalance in the ratio of bone formation to bone resorption, such that, if unmodified, the subject will exhibit less bone than desirable, or the subject's bones will be less intact and coherent than desited. Bone deficit may also result from fracture, from surgical intervention or from dental or periodontal disease. By "cartilage defect" is meant damaged cartilage, less cartilage than desired, or cartilage that is less intact and coherent than desired. "Bone disorders" includes both bone deficits and cartilage defects.

Representative uses of the compounds of the present invention include: repair of bone defects and deficiencies, such as those occurring in closed, open and non-union fractures; prophylactic use in closed and open fracture reduction; promotion of bone healing in plastic surgery; stimulation of bone in growth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis or disuse osteoporosis and arthritis, or any condition that benefits from stimulation of bone formation. The compounds of the present invention can also be useful in repair of congenital, trauma-induced or surgical resection of bone (for instance, for cancer treatment), and in cosmetic surgery. Further, the compounds of the present invention can be used for limiting or treating cartilage defects or disorders, and may be useful in wound healing or tissue repair.

g. Additionally there is nutritional support, which can be most helpful in addition to the known effectiveness of calcium and/or to support calcium uptake in addition to magnesium and boron.
   i. L'Lysine and L'Arginene aid calcium absorption and help support connective tissue strength.
   ii. Sulfur is necessary for calcium uptake and also serves to increase bone and connective tissue strength.
   iii. Vitamins A, E, D important in retarding the aging process
   iv. Zinc Important for calcium uptake and immune function
   v. Chromium Picolonate; Improves insulin efficiency, which improved bone density
   vi. Maganese; Vital in mineral absorption
   vii. Vitamin C; Important for collagen and connective tissue formation
   Addressing joint health the inventor will not go into a lengthy dissertation, but just to mention that there are supplements, with sound science, that if taken regularly, which is problematic in and of itself, (and covered in this writing) not just joint pain, but the joint quality and joint socket can be addressed as well. Nutritive substances that can help include but not limited to balanced supplementation of minerals, Since the body's connective tissue and cartilage include a natural compound called glucosamine, Glucosamine has been clinically studied to build joint cartilage. Glucosanmine sulfate is the preferred form of supplemental glucosamine as it has been shown to be up to 98% absorbable, so more glucosamine reaches the joint structures. Devil's Claw Complex contains standardized extracts of devil's claw root, which supports joint health and acts as an antioxidant; nettle leaf, which supports circulation; and ginger root, which has antioxidant effects. Cherries are a source of flavonoids, natural compounds that contribute to the integrity of capillaries, collagen structures, eyes, joints, and arteries. The anthocyanidin and proanthocyanidin flavonoids in cherries also have antioxidant properties to help disarm free radicals, which can damage healthy cells.

14. The object of the invention is to present a fiber-water composition designed to support the immune system: Immune Enhancing Fiber-Water, simultaneously with hydration.
   a. Our bodies are constantly at war, under assault 24-hours a day from infection and toxins. The fact that we survive at all is due to our immune system—a fascinating network of chemicals and cells that protect the body. The immune system is your body's defense against invaders. It can be divided into two sub-groups—the innate immune system (which covers three areas) and the adaptive immune system.
      i. The Innate Immune system
         (1) The skin and mucosal membranes. The skin and the lining of the body cavities that open to the outside must provide a protective barrier. The entrance to the organs like the gut and the reproductive tract needs to prevent invasion by any pathogenic micro-organisms. The oil or 'sebum produced by the skin keeps its pH slightly acidic which controls the growth of any organisms on the skin. The mucosal membranes secrete a variety of fluids, such as saliva by the gastro-intestinal tract and mucus in the respiratory tract, which provide a defense against pathogenic micro-organisms. The body carries its own natural 'flora' of micro-organisms.
         (2) Secreted soluble proteins: These proteins and enzymes, such as lysozyme, c-reactive protein, interferons and the complement system, are present in the body secretions and fluids and attack different micro-organisms in a variety of ways, often by dissolving their protective layer
         (3) Cells: Most of the white blood cells, called granulocytes (including neutrophils, basophils and cosinophils), alongside others called macrophages, mast cells and natural killer (NK) cells, have a role in initial defense. They arrive at the site of damage or infection and either eat up the invading organisms (known generally as 'antigens') by a process called phagocytosis, or release chemicals toxic to the invader. Some of them also play a part in killing abnormal cells or tidying up the debris after such a fight. The Adaptive Immune system
      ii. The adaptive immune system: is more complex and has the ability both to recognize different 'antigens' by a group of proteins across its cell surface (a bit like a chemical fingerprint) and to retain a memory of them so that the next time the antigen invades the fighting response is quicker. Every organism will have its own individual group of proteins, known as the major histocompatability complex (MHC). Human cells have their own, also known as the HLA (human leucocyte antigen complex) and this is the 'tissue typing' which is done when you need to be matched to someone for an organ transplant.
         (1) Cells called lymphocytes include: Plasma cells and B cells—The plasma cells secrete and the memory cells 'wear' molecules called imunoglobulins or antibodies. These molecules are grouped either as IgG, IgA, IgM, IgE and IgD depending on their exact function and location in the body. They act by passing messages about the invader to other cells, which will then attack it, or by attaching themselves to the antigen itself. T cells—these particularly help in the fight against intracellular pathogens such as viruses and also help to prevent the growth of 'altered self' cells such as cancer cells. They work by recognizing the MHC and the antigen. There are a variety of different T cells including helper T cells, cytotoxic cells and memory cells.

(2) Antigen-presenting cells: These are cells that have begun to process antigens and include macrophages and B cells. They then present the antigen to the T cell, which will continue the attack.

(3) Secreted chemicals: Chemicals such as antibody, complement and cytokines are secreted by different cells around the body and have a role in the complex recognition and attack on antigens. The lymphocytes are produced by lymphoid tissue around the body. The primary lymphoid organs are the bone marrow and the thymus, providing the development and maturation of the lymphocytes. The lymphoid tissue is connected by the 'lymphatic drainage system'—a system of vessels, which allow the lymph fluid to dram back to the venous blood system via the 'lymph nodes'. These nodes provide somewhere for the lymphocytes, along with other cells, to attack the antigens. It is these nodes, which you notice as being 'swollen glands' when, for example, you have a throat infection. The bone marrow and the thymus, the primary lymphoid organs, are responsible for the development and maturation of the lymphocytes. The secondary lymphoid tissues are the lymph glands, spleen and the 'mucosal associated lymphoid tissue' (MALT), which includes the tonsils appendix and 'Peyers patches' in the intestine. There is also some very diffuse lymphoid tissue in the wall of the intestine and in the lungs.http://www.bbc.co.uk/health/immune/—top b. Modern conventional medicine battles diseases directly by means of drugs, surgery, radiation, and other therapies, but true health, believed by the inventor, can be obtained by maintaining a properly functioning immune system. (This will include anti-bacterial, anti-viral compositions separately and/or combined)

c. U.S. Pat. No. 6,328,967 to Rivera (Allergenics Inc. San Francisco Cailf.), issued Dec. 11, 2001, titled: Delivery System to modulate immune response. This invention is directed generally to a method of selecting and/or selectively modulating an immune response by administering a microencapsulated immunogen.

1. An immunogenic response is most predictably induced by using a protein as the immunogen. In immunotherapy, the protein is frequently administered parenterally, for example by injection. While injections are inconvenient and uncomfortable to many patients, they have heretofore been a common route of administration because protease enzymes, and acid in the stomach, and enzymes in the small intestines degrade orally administered protein. It has been demonstrated that oral administration of a soluble protein such as the model antigen ovalbumin (OVA) results in the induction of immune tolerance, characterized by the loss of either antibody or T cell response to the protein antigen. Here presented is a method of better selecting and selectively modulating a particular immune response from the complex immune repertoire to better respond to different antigenic stimuli in different conditions requiring treatment. This invention provides methods and compositions to induce an enhanced general or selective immune response. An Immynogen delivery system comprises a microsphere of an immunogen bound to an inert particle having a mesh size greater than about 35 mesh. The microsphere is administered to the small intestine of a mammal. The microsphere is preferably administered orally and contains one or more enteric coatings and may be administered in a gel capsule. In one embodiment the inert particle has a mesh size greater than about 40 mesh and may be a nonpareil, a silica powder, a salt crystal or a sugar crystal.

d. Soluble fiber is known to bind to heavy metals, and other toxins, and remove them from the body. However, while that is a start, this invention goes beyond just that. It is the purpose here to deliver prescription medications if needed (including Over the Counter {OTC} products as well), but most important is to strengthen the immune system, whether it is damaged as a result of disease, stress, inadequate nutrition, poor living habits, chemotherapy, or a combination of one or more of these factors.

i. Vitamin A is the best anti-infection vitamin and very important in defending he health of the organism. (If used properly, and in moderation it is not toxic)

ii. Vitamin C is considered by this inventor to be the most important vitamin for the immune system. It is essential for the formation of adrenal hormones and the production of lympocytes. It also has a direct effect on bacteria and viruses. Vitamin C, if taken as a supplement, and in this case used in the enhanced water for increasing immunity it should be augmented with bioflavinoids (natural plant substances that enhance the absorption and reinforce the action of this vitamin.

iii. Zinc boosts the immune response and promotes the healing of wounds when used in the appropriate dose (100 milligrams or less a day, over that may depress the immune system). Zinc also helps protect the liver.

iv. Geranium is a trace mineral that is beneficial to the immune system, v. Pro-blotics and pre-blotics are important bacteria to restore and protect vi. Co-enzyme Q10 supports the immune system vii. Garlic stimulates the immune system viii. Amino acids and antioxidants for which literature is replete 15. The object of the invention is to present a fiber-water composition designed to reduce bad breath, body odors, and fecal odors, simultaneously with hydration: Odor reducing Fiber-Water a. Volatile sulfur compounds, mainly H.su.2S and CH.sub.# SH, generated in the oral cavity have been documented to be among the cause of bad breath. Generally, the presence of these compounds is most noticeable after long periods of reduced saliva flow and abstinence from food or liquids, resulting in morning breath. Typically, serious dieters have the same problem and additionally when in a state of ketosis, their breath smells like soured juicy fruit gum. Therefore it is a well-intended extension of the diet-fiber-water for weight loss to include an ingredient(s) with proven science to address this condition. Personal motivation for the ingestion of this functional water may be more to address bad breath and/or body odors than the fore-mentioned reasons.

b. Nabisco, Inc., (Parsippany, N.J.) U.S. Pat. No. 6,030,605 to D'Ameila et al., issued Feb. 29, 2000, tided: Breath freshening compositions and methods using them, teaches us that a physically acceptable zinc compound, including zinc salts). The preferred zinc compounds for use in accordance with the present invention are zinc gluconate and zinc lactate. U.S. Pat. No. 5,405,836 to Richar et al. (Nabisco®), issued Apr. 11, 1995, tided: Pet foods with water-soluble zinc compound coating for controlling malodorous breath, uses a water-soluble zinc coating in pet foods to control malodorous breath.

c. U.S. Pat. No. 5,900,251 to Raissen et al. (Breath Assure®, Inc., Calabasas, Calif.), issued May 4, 1999, tided: Internal breath freshener and digestive aid, provides an herbal or herbal extract for the control and treatment of breath odors and with the added benefit of improving digestion. The ingredients selected are ginger, licorice, chamomile, parsley seed oil, and sunflower seed oil in a delivery system. Persimmons have been use for the purpose of addressing foul breath also.

d. The most exciting to date and for which the inventor is including is Champex® by Ricom of Japan, Maypro® US distributor (NY) is a mushroom derivative which has been demonstrated to reduce breath, body and fecal odors. Mushroom (*Agaricus bisporus*) has enjoyed a long association with food culture and cuisine throughout the world over the centuries and it has a long history of being cultivated for human consumption for more than 2,000 years. In fact, annual consumption per nation amounted to be approximately 526,060 tons in the USA 220,428 tons in Germany, 139,536 tons in France. World production of *A. bisporus* in 1980 was reported 884,000 tons per annum and it is estimated that current production is over 1,000,000 tons.

Given that *A. bisporus* has been consumed world wide, there should be no doubt as to its safety as a daily food. The safety of *A. bisporus* has been confirmed by an oral chronic study entitled "Carcinogenucity examination of *A. bisporus*, edible mushroom, in rats", in which a diet containing a 30% dry powder of *A. bisporus* was given to CD rats for 500 days. Champex is made from the extract of *A. bisporus* with other inert natural ingredients. Champex, the natural extract derived from a white mushroom (*Agalicus bisporus*) reduces mouth, body and fecal odors by suppressing putrid substances in the intestine. At the recent study, it has also determined that Champex retards the progression of renal failure by detoxifying the blood.

i. There are two major causes of mouth odors. One is decaying food debris between the teeth, on the mucous membrane or in the esophagus. This type (odors in the mouth cavity) is generated as time elapses. Another is the foul odor that is absorbed from the intestinal tract into the blood, then breathed out from the lungs as foul breath. In other words, foul mouth odors are a mixture of odors from the mouth and intestines.

ii. The cause of body odors . . . These odors are composed of putrid intestinal chemicals that are absorbed into the blood and excreted through the sweat glands.

iii. The cause of fecal odors . . . More than 100 trillion bacteria exist in the intestines. They create foul-smelling chemicals by decomposing the proteins and fats in ingested foods. Major representative putrefaction bacteria are Welch bacillus and *Escerichia coli,* which create such foul-smelling chemicals as ammonia, indoles, skatoles, triptamine, mercaptan, hydrogen sulfide, and amines. Fecal odors originated from the rotten odors caused by such putrid chemicals.

iv. Delivering Champex; while encapsulation is not always necessary it may be most desirable and efficient in larger doses and/or with timed releasing activity do to the aforesaid and the to be said.

v. Supression of the 3 catagories of odors . . . Consumed internally, Champex reacts with odor-causing chemicals in the mouth as well as in the intestines to suppress foul breath, body odors, and fecal odors.

vi. It is also noted that Champex cleans the blood . . . Champex suppresses those putrid substances in the intestines that are transmitted from the intestinal canal into the blood, thereby preventing the blood from being tainted.

vii. Physiological activity. Champex reduces functional burdens on the kidneys and liver, suppressing the progression of renal failure and hyperammonemia, while toning and improving them. Champex has been determined to suppress the progression of renal failure and hepatic encephalopathy. It also suppresses the generation of active oxygen and the allergen leucotriene, both of which are closely associated with disease and aging. Champex reduces functional burdens on the kidneys and liver, suppressing the progression of renal failure and hyperammonemia, while toning and improving them. Champex has been determined to suppress the progression of renal failure and hepatic encephalopathy. It also suppresses the generation of active oxygen and the allergen leucotriene, both of which are closely associated with disease and aging.

vii. Beauty nutrition ingredients . . . Champex contains many of the minerals and amino acids that people tend to lack these days, as well as glucide such as nucleic acid, mannitol, hemi-cellulose that act as physiological activators to develop proper immunity. Many of these components are unique to mushrooms and are considered effective in dissolving cholesterol, lowering blood pressure, and bolstering immunity against viruses.

16. The object of the invention is to present a fiberwater composition for the removal of toxins from the body, support the immune for preventative measures, address existing cancer, simultaneously with hydration: Toxin Cleansing Fiber-Water.

a. Two in five people will be affected by cancer at some stage in their lives. In the US one person dies from cancer every minute and another 3,000,000 have cancer. Cancer is not one disease but many, all with some similar features but all with distinctive characteristics, which varies according to the cancer's type and location. There are over 200 types of cancer, but all start in the same way. The control signals in a normal cell in the body go wrong, resulting in an abnormal cell. Cells normally divide in a controlled way, but abnormal cells keep on dividing and dividing and this forms a lump. This cluster of abnormal cells is called a tumor. Some tumors are benign, or harmless, and often don't need treatment. But malignant tumors—the cancers—can spread. They may be dangerous because they can invade nearby parts of the body and stop them working properly. Cells from malignant tumors can break away and travel to other parts of the body, where they can form new groups of abnormal cells, called secondary growths. The cells grow and spread and this varies from person to person.

b. Soluble fiber binds to heavy metals and, along with toxins, removes then from the body.

i. High fiber diet can cut cancer risk by 40%: study Jun. 26, 2001 London, (Reuters)—A high fiber diet can slash the risk of developing deadly cancers by as much as 40%, scientists said Saturday. Results from the biggest ever study into diet and cancer, involving 400,000 people from nine countries and presented at an international conference in France, showed fiber was particularly important in reducing cancer of the colon and rectum." These are the first positive results for the benefits of fiber from such a large group. We placed 400,000 people on the study into five sets according to their consumption of fiber," Professor Sheila Bingham of the Dunn Human Nutrition Unit at Cambridge University said in a statement released in London." The group eating the most fiber reduced their risk of colorectal cancer by as much as 40%," she added. The findings were part of the EPIC (European Prospective Investigation of Cancer and Nutrition) study that was reported at the European Conference on Nutrition and Care in Lyon, France. Medical experts believe up to 30% of all cancers in the developed world are associated with nutritional factors and could be avoided by better-balanced diets. The People are advised to eat five portions of fruit and vegetables a day to achieve optimum health and avoid cancer. "These finding are important because of the sheer scope of the EPIC study. They put fiber firmly back on the menu as an important part of a healthy diet," said Professor Gordon McVie, the director general of the Cancer Research Campaign, which sponsored Bingham's research.

Carcinogenesis and Immune Response in Cancer
 The body is composed of billions of cells, which are all subject to free radical damage and mutations caused by various carcinogens. Free radicals and carcinogens cause cells to become mutated and abnormal. The immune surveillance system plays a critical role in prevention of cancer by recognizing the formation of these abnormal cells. T-cells in particular are valuable for their ability to distinguish the mutated cells from normal cells. Yet, when the immune system is suppressed, the mutated carcinoma cells are not recognized by the immune surveillance system and the cells grow uncontrollably and become cancerous. Cancer cells release several kinds of immune suppressive factors, which inhibit antigen and macrophage activity. T-cells in a suppressed immune system do not recognize cancer cells. The suppressed macrophage cells fail to produce IL-12 and thus the Th0 cells cannot proliferate or differentiate into Th1/Th2 cells. The suppressed Th1 cells cannot exert their anti-tumor effects which include production of IL-2 and IFN-?. Finally, the anti-cancer immune response fails when the proliferation of CTL, LAK or NK cells fails. Cancer is a disease of the immune system whereby immune suppression allows cancerous cells to not be recognized and grow uncontrollably. Thus, reversing and restoring the suppressed immune system should be a very important part of cancer treatment.

The inventor presents qualified research to show the connection between obesity and cancer. As has been addressed fiberwater addresses obesity as well as demonstrating that soluble fiber binds to toxins and removes them from the colon. Now additionally the next generation, new and novel fiberwater(s) with their viscosity changes and encapsulated ingredients.

ii. On the connection between obesity and cancer Americans Don't Know Obesity Increases Cancer Risk and, Researchers Express Alarm at New Survey Findings: WASHINGTON, DC—Speaking at a press conference at the AICR/WCRF International Research Conference on Food, Nutrition and Cancer, Professor W. P. T. James, chairman of the International Obesity Task Force, said, "We are used to thinking about the obesity epidemic on one hand and the cancer epidemic on the other. We need to think of them as linked." A new survey commissioned by AICR, however, indicates that although Americans are deeply concerned about both obesity and cancer, remarkably few are aware of the link between the two. Asked to name major risk factors for developing cancer, only 6 percent of 1,025 Americans surveyed mentioned overweight and obesity. They were more likely to mention exposure to certain chemicals (22 percent), high-fat diets (18 percent), exposure to the sun (18 percent), family history (11 percent) and alcohol (7 percent). Later in the survey, Americans were read a list of chronic diseases and specifically asked which ones are significantly affected by overweight and obesity. The great majority were able to identify heart disease (89 percent) and diabetes (86 percent) as conditions made more likely by being overweight or obese. Only 25 percent, however, were aware that overweight and obesity increase cancer risk. Citing a report issued by the International Agency for Research on Cancer, an agency of the World Health Organization, James estimated that being overweight and inactive accounts for one-quarter to one-third of worldwide cases of breast cancer, colon cancer, endometrial cancer, kidney cancer and esophageal cancer. "That's somewhere between 102,000 and 135,000 cases in the U.S. alone," he said. This link is important, James noted. "People need to be aware of it if they are to take steps to reduce their risk of getting cancer," he said. Conversely, the rapid increase in the number of people who are obese in the U.S. and worldwide could have a dire long-term effect on cancer rates. Unless people take the necessary steps, James said, we are headed for a steep escalation in cancer cases. James reported that one billion people are overweight (Body Mass Index over 25) and, of that group, 300 million are obese (Body Mass Index over 30) worldwide. According to the Centers for Disease Control and Prevention, 61 percent of American adults are now classified as overweight or obese and 27 percent are considered obese. Conducted between Jun. 27 and Jun. 30, 2002, the Harris survey entailed polling 1,025 adults aged 18 and over, using an unrestricted Random Digit Dialing technique that significantly reduces bias and ensures that respondents with both listed and unlisted telephone numbers are reached. The margin of error for the total sample is 3.1 percent. The American Institute for Cancer Research (AICR) is the nation's third largest cancer charity, focusing exclusively on the link between diet and cancer. The Institute provides a wide range of education programs that help millions of Americans learn to make dietary changes for lower cancer risk c. This inventor, institutions worldwide, private researchers, as well as The European Conference on Nutrition and Cancer, is looking at the impact of different types of food/supplements as related to the disease. The nutritional support listed are to be considered for those who have been diagnosed with the disease as well as, or even more so, for those in which cancer is in their family genetically, and/or to enhance their chances of avoiding the condition. Using fiberwater as a base, and with controlling the viscosities as well, with the dosage released via encapsulations, along with supportive scientific supplementation given, which by this invention is protected so as to be stable and bio-available to the user, the following is a mere suggestion of such supplementation:
  i. Commonly known include: Coenzyme Q 10, Dimethylglycine (DMG), garlic, Melatonin, Natural Beta Carotine or cartenoid complex, Proteolytic enzymes, Selenium, Shark Cartledge, Superoxide dismutase (SOD), Vitamin A (People with cancer require a higher amount emulsion safer at higher doses) Vitamin B Complex, Vitamin C with bioflavnoids (promotes the production of interferon in the body) Grape Seed extract), Taurine (Functions as a foundation for tissue and/organ repair) L Carnitine, and more.(it is important to note that the inventor believes that the form of delivery is very important to efficacy)
  ii. Not as commonly known include:
    (1) Active Hexose Correlated Compound (AHCC) (Ricom, Japan) is an extract of the mycelia from several species of basidiomycete mushrooms. It is derived from a highly specialized manufacturing process allowing for optimal bioavailabilty (due to its low molecular weight).
      (a) Research Association symposiums. Clinical studies have shown AHCC to significantly increase immune response, activate macrophage activity, NK and LAK cells, increase production of cytokines including TNF-Error! Unknown switch argument., IFN-Error! Unknown switch argument., IL-1, IL2, & IL-12. Studies show AHCC increases the quality of life for patients with: cancer, AIDS, chronic fatigue, and other immune disorders. Decreases viral loads by 85% or more in Hepatitis C patients (Fred Pescatore, MD in NY & TX, and Lawrence Kempf, MD in NY have noticed these benefits in as little as 2–3 months.)
      (b) AHCC decreases white blood cell reduction and anemia seen during chemotherapy.
      (c) AHCC restores and reverses a suppressed immune status by stimulating and activating the immune system and finally wiping out cancerous cells.
      (d) The Institute for Genetic Medicine at Hokkaido University found that the macrophage population harvested from AHCC peritoneal treated rats increased twice as much as rats in the control group, for both normal rats and in tumor-bearing rats. This result demonstrated that AHCC increased the proliferation and activation of macrophages. (The 4th Symposium of AHCC Research Association, June 1997).
      (e) In summary, the results of the basic and clinical research indicated AHCC is a powerful anti-tumor substance, which works by activating and enhancing the cells of the immune system. The powerful immune regulating effects of AHCC could be used in a variety of immune related diseases. Since 1986, the AHCC Research Association has been examining and discussing the effects of AHCC on cancer, hepatitis, and ailments involving immune dysfunction. Research is now underway at more than 150 institutes, including national research centers and university hospitals in Japan and the US. Each year since 1994, over 300 medical doctors and researchers have gathered in Sapporo, Japan for the AHCC conference. AHCC has been the subject of some 325 clinical studies conducted at prestigious Japanese institutions such as Hokkaido University, I(yorin University, and Teikyo University. More clinical trials will be completed at Harvard University, University of California at Davis, Columbia Presbyterian University, Thomas Jefferson University, and NY Medical College. Over 700 hospitals and medical centers in Japan recommend AHCC as part of an ongoing immune enhancement program.
    iii. Genistine Concentrated Polysaccharide (GCP) (Amino UP Chemical Co., Ltd. Japan) is a natural anti-tumor substance. GCP™ is a nutritional supplement made by the Amino Up Chemical Company in Sapporo, Japan. It is a mixture of a mushroom and soybean extract. Research on GCP™ has shown it can reduce prostate cancer cell growth and the formation of blood vessels in prostate tumors. GCP is a novel functional health additive produced by fermination of soybean isoflavone extracts with basidiomycetes.

d. U.S. Pat. No. 6,410,061 to Moore et al. (Purdue Research Foundation Lafayette Ind.), issued Jun. 25, 2002, titled: Tea catechins as cancer specific proliferation inhibitors abstracts: The invention described herein encompasses a methods and compositions of treating cancer or solid tumors comprising the administration of a therapeutically effective amount of catechins, a group of polyphenols found in green tea, to a mammal in need of such therapy. Compositions of catechins include but not limited to, epigallocatechin gallate (EGCg), epicatechin (EC), epicatechin gallate (ECG), epigallocatechin (EGC). The unique compositions of the invention contain various combinations of the catechins, alone or in combination with each other or other therapeutic agents and are used to treat primary and metastatic cancers in humans. The invention also encompasses the varying modes of administration of the therapeutic compounds.
  i. The invention described herein encompasses a method of treating cancer or solid tumors comprising the administration of a therapeutically effective amount of catechins, a group of polyphenols found in green tea, to a mammal in need of such therapy.

ii. In accordance with the present invention, the catechins can be used alone or in combination with other known therapeutic agents or techniques to either improve the quality of life of the patient, or to treat cancer or solid tumors. The catechins can be used before, during, or after the administration of one or more known chemotherapeutic agents, including antitumor agents.

iii. In addition, the catechins can be used before, during, or after radiation treatment.

iv. In another embodiment, the compositions of the invention are sterile pharmaceutical compositions suitable for intravenous injection or infusion. In another embodiment, the invention encompasses a composition suitable for oral delivery, comprising catechins and a pharmaceutically acceptable excipient or carrier. A preferred embodiment comprises a sustained release composition to maintain the circulating levels of said composition at a certain minimum level for therapeutic efficacy over a specified time period.

17. The object of the invention is to present a fiber-water composition designed for addressing general stress: Anti-Stress Fiber-Water, simultaneously with hydration.

a. It is the object of this functional Fiber-water to provide anti-stress (calming) agents, which can address the situation as best as possible considering that there are no known drugs that are able to fundamentally inhibit or reduce stress. There are drugs, such as anti-anxiety agents and sleeping pills for temporarily alleviating somatic reactions when exposed to stress and are considered to be an effective means of dealing with stress. Also there are various relaxation techniques for the mind and body which been proposed as ways of effectively controlling stress so prevent destruction of the body's homostasis. Stress disorders and other related disorders are believed to comprise a condition in which stress destroys the ability to maintain homeostasis by the body.

b. Stress is quite prevalent in modern society, and those diseases caused by stress, namely somatic disorders as well as stress disorders such as neurosis and depression, are increasing. In modern society, people under go various kinds of stress caused by being exposed to highly advanced and complicated scientific technology, or drastically changing social circumstances. Particularly, in the internationalized and industrialized and computerized society, complex human relationships are formed, causing mental stress. It has been reported that a variety of symptoms are caused by mental stress.

It is also recognized that mental stress has a great influence on all the systems of the body especially the circulatory system. Further stress affects the immune system.

c. Various drugs have been developed and marketed for this and overlapping conditions however not with our serious side effects, acute, chronic or even temporary. They can cause both physical and psychological dependence. Regular use over a long period of time may result in tolerance, which means people have to take larger and larger doses to get the same effects. When regular users stop using large doses of these drugs suddenly, they may develop physical withdrawal symptoms ranging from restlessness, insomnia and anxiety, to convulsions and death. When users become psychologically dependent, they feel as if they need the drug to function. Finding and using the drug becomes the main focus in life.

d. Sedative-hypnotics are drugs, which depress or slow down the body's functions. Often these drugs are referred to as tranquilizers and sleeping pills or sometimes just as sedatives. Their effects range from calming down anxious people to promoting sleep. Both tranquilizers and sleeping pills can have either effect, depending on how much is taken. At high doses or when they are abused, many of these drugs can even cause unconsciousness and death.

e. Barbiturates and benzodiazepines are the two major categories of sedative-hypnotics. The drugs in each of these groups are similar in chemical structure. Some well-known barbiturates are secobarbital (Seconal) and pentobarbital (Nembutal). Diazepam (Valium), chlordiazepoxide (Librium), and chlorazepate (Tranxene) are examples of benzodiazepines. A few sedative-hypnotics do not fit in either category. They include methaqualone (Quaalude), ethchlorvynol (Placidyl), chloral hydrate Noctec), and mebrobamate (Miltown). All of these drugs can be dangerous when they are not taken according to a physician's instructions.

i. Barbiturates are often called "barbs" and "downers." Barbiturates that are commonly abused include amobarbital (Amytal), pentobarbital (Nembutal), and secobarbital (Seconal).

(1) Small amounts produce calmness and relax muscles. Somewhat larger doses can cause slurred speech, staggering gait, poor judgment, and slow, uncertain reflexes. Barbiturate overdose is a factor in nearly one-third of all reported drug-related deaths. These include suicides and accidental drug poisonings. Accidental deaths sometimes occur when a user takes one dose, becomes confused and unintentionally takes additional or larger doses.

(2) With barbiturates there is less difference between the amount that produces sleep and the amount that kills. Furthermore, barbiturate withdrawal can be more serious than heroin withdrawal. These effects make it dangerous to drive a car or operate machinery. Large doses can cause unconsciousness and death.

f. Other sedative-hypnotics which are abused include glutethimide (Doriden), ethchlorvynol (Placidyl), and methaqualone (Sopor, Quaalude).

g. Methaqualone ("Sopors,""ludes") was originally prescribed to reduce anxiety during the day and as a sleeping aid. It is one of the most commonly abused drugs and can cause both physical and psychological dependence. The dangers from abusing methaqualone include injury or death from car accidents caused by faulty judgment and drowsiness, and convulsions, coma, and death from overdose.

h. There are also pills manufactured to look like real sedative-hypnotics and mimic their effects. Sometimes look-alikes contain over-the-counter drugs such as antihistamines and decongestants, which tend to cause drowsiness. The negative effects can include nausea, stomach cramps, lack of coordination, temporary memory loss, becoming out of touch with the surroundings, and anxious behavior.

i. Alcohol and sedative-hypnotics taken together, alcohol can kill. The use of barbiturates and other sedative-hypnotics with other drugs that slow down the body, such as alcohol, multiplies their effects and greatly increases the risk of death. Overdose deaths can occur when barbiturates and alcohol are used together, either deliberately or accidentally.

j. Babies born to mothers who abuse sedatives during their pregnancy may be physically dependent on the drugs and show withdrawal symptoms shortly after they are born. Their symptoms may include breathing problems, feeding difficulties, disturbed sleep, sweating, irritability, and fever. Many sedative-hypnotics pass through the placenta easily and have caused birth defects and behavioral problems in babies born to women who have abused these drugs during their pregnancy.

k. The inventor is hopeful that unless absolutely necessary and under a doctors care the public will turn to more natural means totally or at least at a first go around. Foods/beverages by category and then the ingredients in these products have been have been developed for the purpose of preventing and reducing stress or fatigue as related to stress. Typical examples of these include the category of:
   i. Sports drinks: They do not prevent or reduce stress and fatigue directly.
   ii. Tonics, on the other hand, contain extracts from several medical plants in addition to vitamins and amino acids. These are expected to have physiological effects such as central nervous system stimulation, increased blood flow, cardiac effects and activation of endocrine system. However, many of the physiological effects of these natural drugs are based on old legends, and none are known, on a scientific basis, to prevent or reduce stress. (Formulation into a tonic, a concentrate, a decoction, an elixir, and/or the like are all to be considered as a form of delivery for this invention and covered later in this writing.)

l. More recently, there have been numerous reports, which stated that stress affliction, and numerous mental disorders are all pronounced emotional disorders, indicating research results that show that these disorders are closely linked with decreased immunological function of the body. Although the concept of mental anguish being a cause of illness is itself quite old, only recently has attention been focused on this concept in scientific fields as well.

m. Considerable immunological research has been conducted on the relationship between stress and cancer in particular. However, there are no known specific compounds that inhibit the onset, and metastasis, of cancer caused by stress. However, long-term efforts will most likely be required due to fulfill the social demand as mentioned above, which can be taken repeatedly throughout the day and/or daily and/or as part of a program without any problems with safety, and which can mitigate and hopefully prevent mental and physical symptoms caused by stress.

n. U.S. Pat. No. 6,410,685 to Masuyama, et al. (Calpis Co.Ltd., Toyko, JP), issued Jun. 25, 2002, titled: Anti-stress agents and functional foods, reports that when one undergoes stress, anglotensive II increases, and intracorporeal sodium due to sodium reabsorbancy becomes excess, which causes rise in blood pressure (Osamu Mobara et al.: Taisha, 28, 2, 323, 1991). Based on such findings, studies have been made on the effect of enalapril and alacepril, which are angiotensin converting enzyme inhibitors and used as antihypertensive agents, on hypertension caused by stress (The American Journal of Cardiology; 68, 15, 1362(1991), Internal Medicine; 32, 9, 691(1993)). However, it is considered that suffering stress not only causes rise in blood pressure, but also influences various factors to cause stomach ulcer, ischemic heart diseases, cerebrovascular diseases, hyperlipemia, or the like. Therefore, though stress is regarded as one of the causes of hypertension, it is not believed that the anti-stress effect is achieved merely by suppressing the rise in blood pressure.

o. U.S. Pat. No. 6,265,450 to Asami et al. (Suntory Limited Osaka JP.) (Itano Foods (Tokushima, JP.), issued Jul. 24, 2001, titled Anti-stress composition presents an anti-stress composition having for its active ingredient astaxanthin and/or its ester. This composition can be in the form of a pharmaceutical, functional food, or beverage and/or so forth.

18. The object of the invention is to present a fiber-water composition designed for regulating mood: Fiber-water for mood regulations, simultaneously with hydration.
   a. Soluble fiber is known to moderate the pos-prandial rise in blood sugar levels, ergo prevent mood swings in those who tend to have repetitive peaks and valleys in their blood glucose levels. It is desirable to add additional ingredients to the fiber-water to enhance this effect. (moderating moods with small amounts of glucose is considered invented), however, sometimes just a sweetener fools the body into believing that there is sugar (aka a placebo effect) and that is also invented.
   b. If encapsulated and/or regulations with viscosity (or both) changes (with or without glucose and/or sweetener) so that the affect of the fiber and the affect of the viscosity (be it the property of the fiber or no, or both) and the "releasability", differentials of the encapsulations (if deemed appropriate to this formulation) all serve to present formulators the delivery variables (delivery systems) which in turn has the capabilities of making a most desired and needed product.
   c. U.S. Pat. No. 6,410,522 to Ruenberg (Heifa, I L), issued Jun. 25, 2002, titled: Anti-depressant, stress suppressor and mood improver; calls attention to the present invention which relates to a composition having an effect of alleviating symptoms associated with depression and mental and emotional stress.
   d. A method for improving symptoms of depression, mental & emotional stress and mood in a subject in need thereof by reducing the blood cortisol level and serotonin reuptake in the brain of said subject, comprising administering an effective amount of the composition to said subject.
   e. Herein presented a pharmaceutical or nutritional composition for treating depression, for suppressing mental & emotional stress and for improving mood comprising Phosphatidyl-L-serine and Phosphatidic acid or salts thereof as the effective ingredients, comprising at least 20% (w/w) Phosphatidyl-L-serine out of the total phospholipid content of the composition and at least 3% (w/w) of Phosphatidic acid out of the total phospholipid content of the composition, wherein the Phosphatidyl-L-serine and Phosphatidic acid have a structural fatty acid chain derived from at least one raw material lecithin selected from the group consisting of soy bean lecithin, rapeseed lecithin, and egg yolk lecithin, and which is produced by reaction with Phospholipase-D.
   f. As an agent for preventing and mitigating mental and physical symptoms caused by stress, chemically synthesized medicaments such as a tranquilizer, an anti-anxiety agent, and sleeping pills are presently used. However, these medicaments have habituation and side effect problems, so that it is not preferable to use them daily for the purpose of preventing mental and physical symptoms caused by stress. Accordingly, an anti-stress agent that can be taken repeatedly and daily without any problems with safety, and that can mitigate and prevent mental and physical symptoms caused by stress are desired and are under development.

g. For example, there are proposals such as an anti-stress agent containing as an effective ingredient L-theanine contained in tea leaves (Japanese Laid-open Patent Application No. 6-100442), an anti-stress composition containing imidazole compounds such as anserine, valenine, n-methylhistidine, or r-methylhistidine h. Japanese Laid-open Patent Application No. 9-20660), and anti-stress food containing a composition of glutathione and antioxidant Japanese Laid-open Patent Application No. 8-275752).

i. There is also a report on stress reducing effect of fragrance (Fragrance Journal: 1991–11, p44–49). However, there has not been reported that a tripeptide has the effect of mitigating and preventing mental and physical symptoms caused by stress.

j. This inventor believes in aromatherapy and the fact that certain aromas have be, back to ancient times, associated with moods. Lavender is especially known to be considered relaxing and stress 19. The object of the invention is to present a fiber-water composition to increase alertness focused on delivering a stimulating effect, Stimulating Fiber-Water, simultaneously with hydration.

a. Stimulants were a name originally given to several groups of drugs that tend to increase alertness and physical activity. The groups include pharmaceuticals such as amphetamines and the street drugs commonly called "uppers" or "speed," and cocaine. (Cocaine's recent notoriety belies the fact that the drug has been used as a stimulant by people for thousands of years. Its properties as a stimulant have led people in the past to use it in a number of patent medicines and even in soft drinks).
    i. The more widely abused stimulants are amphetamines and cocaine. Cocaine has limited commercial use and its sale and possession are strictly controlled.
    ii. Amphetamines are sometimes prescribed by physicians therefore their availability makes them prime candidates for misuse. Used properly, amphetamines increase alertness and physical ability. They are often prescribed to counter the effects of narcolepsy, a rare disorder marked by episodes of uncontrollable sleep, and to help children with minimal brain dysfunction. Amphetamines increase the heart and respiration rates, increase blood pressure, dilate the pupils of the eyes, and decrease appetite. Other side effects include anxiety, blurred vision, sleeplessness, and dizziness. Abuse of amphetamines can cause irregular heartbeat and even physical collapse. Amphetamines are psychologically addictive. Users become dependent on the drug to avoid the "down" feeling they often experience when the drug's effect wears off. This dependence can lead a user to turn to stronger stimulants such as cocaine, or to larger doses of amphetamines to maintain a "high".
    iii. That boost we get from that morning cup of coffee is the result of the caffeine that naturally occurs in coffee. Caffeine is a common stimulant and is found not only in coffee and tea, but also in soft drinks and other foods. It can also be bought over-the-counter in tablet form. Too much caffeine can cause anxiousness, headaches, and the "jitters." Caffeine is also addictive and a person who abruptly stops drinking coffee may experience withdrawal symptoms. HERE COMES CAFFEINATED WATER: Caffeinated waters have been on the market for several years under such names as "Water Joe" and "H2O ZIP" etc., which dispurse the caffeine throughout the water. While there are some who sip water, the inventor has noticed that when caffeine is in the water the drinker tends to guzzle the entire bottle for the "NOW" stimulation effect. Coffee drinkers on the other hand seem to "sip" which may be due to the fact that it is too hot to drink all at once, the same with tea.
    iv. This inventor perceives that there is a place for a stimulant including but not just limited to caffeine, yet caffeine is exampled here.
    v.
      (1) To have a sustained release form of caffeine it is here invented that all or a portion, (some of the caffeine be in solution in the fiberwater), of the caffeine be encapsulated with one or more release timed advantages. Ergo caffeine can be released even over a multiple of hours if coated as such.
      (2) Further and so invented here is the ability to use caffeine fiber-water most advantageous combined with fiber-water to support colon motility. Caffeine increases colon motility, thus combined with fiber and used for a specific condition (gastrointestinal track related) this fiber-water caffeine water-like drink can have healthy benefits for general and/or specific humans and/or animals on a continuous regular and/or an as needed basis.
  b. There are many herbs and/or herbal combination that can stimulate and act in the same way that the consumer perceives caffeine to act. Some are thermogenic and speed up the body's metabolism. Ephedra, and Ma Hung, have both been used extensively in basically weight loss products and considered controversial, however Dr. Alan Fleischner, (reputation: Albert M. Fleischner, Ph.D., has a doctorate in Pharmaceutical Chemistry from Rutgers University and has had over thirty years experience in the pharmaceutical industry with firms such as Schering Corporation, Lehn & Fink Division of Sterling Drugs, Bradley Pharmaceutical Corporation, Amerchol Division of CPC and the Goen Group companies, has a number of published papers and two previously granted patents and has several patents pending) in his U.S. Pat. No. 6,420,350 to Fleischner; Albert M. (Goen Group Inc. Cedar Knolls N.J.), issued Jul. 16, 2002, titled weight loss product, abstract: Supplement compositions designed to support weight loss and increase energy teaches that the combination of ephedrine and caffeine increases fat loss, maintains muscle mass, prevents the fall of HDL cholesterol during weight loss, increases insulin sensitivity, reduces lipogenesis and is safe. With the addition of glucosamine sulfate, the new and useful formula is further enhanced.
  c. U.S. Pat. No. 6,416,806 to Zhou, issued Jul. 9, 2002, titled: Herbal caffeine replacement composition. This invention will give the same effect but will not have the same drawbacks. The invention relates to a caffeine replacement composition and various food products such as beverages and the like, which incorporate the same.
    i. As set forth above, a wide variety of food products include caffeine, which is desirable to many people for the alertness enhancing affect of the caffeine. In light of the well-documented disadvantages of caffeine and caffeine addiction, the present invention is intended to provide an herbal replacement, which provides similar alertness enhancement without the disadvantages. Further, compositions are provided as coffee replacement compositions, both in concentrated and diluted or beverage-strength form, which possess substantially the same flavor characteristics as coffee and provide substantially similar alertness benefits through a combination of herbal extracts selected according to the invention.
    ii. In accordance with the present invention, the two critical ingredients to the caffeine replacement composition are Ginkgo biloba extract and kudzu extract which, in appropriate proportions and ratios to each other, serve to advantageously enhance alertness of a person consuming same, typically for approximately the same period of time as an equal serving of caffeine.
    iii. Ginkgo biloba is known to provide improved memory and cerebral circulation, and is also advantageous as an anti-oxidant. However, Ginkgo biloba does not provide any rapidly occurring alertness enhancement. Further, Ginkgo biloba has a very bitter taste and in high doses cannot be tolerated as an ingredient in beverages. For example, in a six-ounce beverage, no more than about 20 milligrams of Ginkgo biloba can be tolerated in terms of taste. Kudzu, which is also known as Pueraria, has a friendly taste and provides almost instant enhancement to alertness. However, this enhancement diminishes quickly and, depending upon the dose, can lose effect within about one half hour to one hour.
    iv. It has now been found in accordance with the present invention that a combination of Ginkgo biloba and kudzu advantageously serves to moderate the bitter flavor of Ginkgo biloba, and the combination serves to provide for an instant and sustained improvement in alertness. The composition according to the invention in typical strengths provides for enhanced alertness for about 2 to 6 hours. This makes the composition surprisingly well suited for use as a caffeine replacement in various food products, especially in a coffee replacement beverage.
20. The object of the invention is to present a fiber-water composition containing nicotine (Nicotine Fiber-Water), simultaneously with hydration.
    a. Nicotine is also now delivered in water in a product called Nico-Water™. Once again it is in solution, and the drinkers observed consuming this product tend to guzzle the entire container. Worse they may choose to guzzle consecutive bottles, as might also occur with caffeinated water. By encapsulating all, or part of these type of ingredients we reduce the potential of unwanted side effects and also moderate the delivery.
    b. It is well known in the literature that it is beneficial to take 25 mg. of Vitamin C with every cigarette as nicotine depletes vitamin C. Ergo we have the invention fiber-water with nicotine and vitamin C. Again we can time release at pre-determined intervals and for very similar and/or different distinctive reasons and advantages
    1. So invented here is to have a sustained release form of nicotine (encapsulated) with one or more release timed advantages. Ergo nicotine can be released even over a multiple of hours if coated as such. Or some of the nicotine may be present in the solution (fiberwater), itself while additional nicotine it is here invented. Either form may include antioxidants, especially Vitamin C to counteract the negative effects of the nicotine. The antioxidants may be present in the general Fiber-water solution, or encapsulated, or both.
    c. The inventor calls attention to the following intellectual properties for which the use of nicotine, positively , be is physiologically or psychologically advantageous. The recent discoveries of the benefits of nicotine are referenced in the following:
        i. U.S. Pat. No. 4,953,572 to Rose, et al., issued Sep. 4, 1990, titled: Method and apparatus for aiding in the reduction of incidence of tobacco smoking. This intellectual property stresses the potential of nicotine poisoning and discusses several techniques, which can be used to control the rate of absorption on nicotine by the body. The inventor here feels that encapsulation in fiber-water alone and/or following the same delivery as above described in relation to putting caffeine in fiberwater,
        ii. U.S. Pat. No. 5,810,018 to Monte, issued Sep. 22, 1998, tided: Method, composition and apparatus for reducing the incidence of cigarette smoking calls attention to the ability of how to uses nicotine and caffeine together in an oral spray device. Quoting Monte, "While scopolamine or any other alkaloid or stimulant can be utilized in the practice of the invention, caffeine is presently preferred because it is often less likely than other alkaloids or stimulants to become habit forming.
            (1) . The liquid carrier in the spray solution is water, alcohol, or any other desired liquid. The liquid carrier is, however, typically an aqueous solution. When caffeine is the stimulant utilized in conjunction with nicotine, the liquid carrier is preferably an alcohol—water mixture because caffeine is at its maximum solubility in such a mixture. The sequence of solutions preferred in the use of the invention gradually decreases the amount of nicotine in each solution and increases the amount of caffeine. Eventually, a solution is used which contains only caffeine and does not contain nicotine. Solutions, which contain only caffeine and do not contain nicotine do not include a sequestering agent and also preferably include ascorbic acid, which improves the solubility of the caffeine. The amount, by weight, of ascorbic acid used is preferably over twice the amount, by weight, of caffeine present in the liquid solution". Using fiber-water and nicotine as a program to reduce the nicotine craving is if one were to look at a series of 10 or more single servings of a product that gradually reduced the quantity of nicotine over time while also supplying additional nutritional support. It is possible to use the encapsulations, with their controlled release to gently and progressively be of help to those desirous of kicking the nicotine habit.
        iii. There are also other means of addressing nicotine withdrawal known in the art. U.S. Pat. No. 4,778,677 to Ebbesen, issued Oct. 18, 1988, tided: Method for treatment of nicotine craving teaches that a combination of glucose, potassium and caffeine may be a method for treating the cravings of nicotine.

By using fiber-water as a carrier and other supporting nutritional ingredients, particularly in the solution fiberwater, with encapsulations in a controlled release form, the inventor can present a product and/or also an entire program to replace the nicotine. Again Vitamin C is important along with other antioxidants.

21. The object of the invention is to present a fiber-water composition designed for those with fatigue, simultaneously with hydration: Fatigue reducing Fiber water (also addressing Fatigue Syndrome (CFS), and/or the symptomology (the general feeling of fatigue/CFS and not diagnosed).
    a. The inventor is very aware of fatigue, (tiredness) and that fatigue comes from and/or is associated with many conditions, which in some instances are overlapping. Tiredness is not uncommon to dieters. It can be due to restricted calories/nutrients and/or both. However there are many reasons for fatigue such as lack of sleep and/or proper sleep, stress, a myriad of psychological reasons, and a myriad of physical conditions. Pain drains energy and causes exhaustion as another example.
    b. CFS, which has become an epidemic, is on the rise. Since this is one of the disorders that require at least 8 (8 oz) glasses of water everyday fiber-water and ir fiber-water with additional additives is ideal. In general, in order to receive a diagnosis of chronic fatigue syndrome, a patient must satisfy two criteria:
        i. Have severe chronic fatigue of six months or longer duration with other known medical conditions excluded by clinical diagnosis, and
        ii. Concurrently have four or more of the following symptoms: substantial impairment in short-term memory or concentration, sore throat, tender lymph nodes, muscle pain, multi-joint pain without swelling or redness, headaches of a new type, pattern or severity, un-refreshing sleep, and post-exertional malaise lasting more than 24 hours.
        iii. A variety of vitamin supplements, medications, and other substances have been described as having potential therapeutic benefits for chronic fatigue syndrome (CFS) patients. Since no cause for CFS has been identified, the therapies for this disorder are directed at relief of symptoms. The physician, together with the patient, will develop an individually tailored program that provides the greatest perceived benefit, based on some combination of the therapies discussed in this section.

22. The object of the invention is to present a fiber-water composition designed for relaxation: Relaxing Fiber-Water, simultaneously with hydration.

Fiber-water with additives that can relax, as opposed to those that stimulate, have their place in the market. This is especially important to those Type A personalities as well as those with stress, stressful psychological conditions, and health challenges. Weight loss and weight management diets do cause nervousness and stress alone. Additional nutritional support is most beneficial to our overstressed population. While there are herbs and other botanicals that are known to support this specific area of concern, the inventor is most interested in L-Theonine, or Theonine, an amino acid derived from green tea. The product Sun Theonine$^\alpha$ by Talyo is considered the best choice for the practice of the invention. Due to the somewhat "off taste" of theonine, especially in higher concentrations, along with the amount that is desired for effect encapsulations are ideal.

23. The object of the invention is to present a fiber-water composition addressing bowel regularity, simultaneously with hydration.
    a. Fiber-water for bowel regularity/maintenance. Fiber is known to affect the bowels. In fact to most consumers today there minds still are focused on the fact that fiber effects bowels. The inventor does acknowledge that this is so, and that it must be given attention although in the next area covered, gastro-intestinal tract health, the inventor makes it clear that she does not wish to go into "more conditions" and all their definitions. Best to just call attention to:
    b. In patent literature we are aware of U.S. Pat. No. 4,834,990 to Amer, issued May 30, 1989, titled: Non-dairy liquid health food. Here we are taught that soluble fibers include plant gums, plant derivatives such as gum Arabic, locust bean gum, citrus pectins, logum tragacanth, agar, carrageenan, xanthan gum and/or other soluble fibers are beneficial.
        i. U.S. Pat. No. 5,380,717 to Ohkuma et al., issued Jan. 10,1995, tided: Food composite for performing function of large bowel regulation and improvement in constipation. This patent uses maltodextrins as the soluble fiber.
        ii. U.S. Pat. No. 5,260,279 to Greenberg, Norman A., issued Nov. 9, 1993 (Sandoz now Novartis), titled: Enteral nutrition and medical foods having soluble fiber. The fibers used here are hydrolyzed guar gum and pectin.
        iii. U.S. Pat. No. 5,558,897 to Goldman, issued Sep. 24,1996, tided: Milk Composition containing fiber and method for making the same, also uses hydrolyzed guar gum.
        iv. U.S. Pat. No. 6,004,610 to Wang, et al., issued Dec. 21, 1999 titled Composition of dietary fiber rich and low viscosity beverages uses fiber blend with the guar gum adding arabinoglactan.

24. The object of the invention is to present a fiber-water composition to improve the health of the gastrointestinal tract; GI FiberWater, simultaneously with hydration.
    a. Once in the mouth food/beverges/"ingestibles" (regardless of their constituents) start their journey through the body. This follows what is called transit time. What we take in effects the entire organism/body/human/animal.
    b. The gastrointestinal tract pertains to the mouth, stomach small and large intestines, colon, rectum, liver, pancreas, and gallbladder. There are many disorders that can affect the health of that specific portion. Some are genetic, others come from the ways in which we treat and/or care for the body, and some just come as a natural part of the aging process. Certainly filling this portion with conditions such as gastritis (inflammation of the stomach lining), gastroenteritis (inflammation of the mucous lining of the stomach and the intestines), colitis (inflammation of the colon), constipation, diarrhea would take volumes. Further just looking at intestinal support, the "friendly", bacteria essential for digestion and/or the metabolism of certain nutrients speak volumes.
    c. Earlier in this writing the inventor pointed out the 70,000,000 people in the US alone who have gastric upset. It is almost beyond imagination, if we look at the entire digestive system and break it down (matrix style), what numbers we would come up with who have needs, desires, challenges and so forth. Sometimes even more than one. (this can be addressed with the ingestion of a daily preset program by a professional and/or by the individual making personal selections for himself/user be they human or animal.

d. In noting the just said it is not important to deviate anymore than with the examples already given from this invention. So, while many ideas and suggestions have been noted/covered, and even by topics such as condition being addressed (chronic or acute/temporary/permanent), age of the user, etc., the essence of the patent is using the invention fiber-water (U.S. Pat. No. 6,248,390) as the foundation delivery system for adding/fortifying enhancing agents (other delivery vehicles (encapsulations) and/or vehicles (viscosity{s} to manipulate the delivery receiving site and rate.

e. The inventor calls attention to U.S. Pat. No. 6,120,803 to Wong et al. (Alza Corp. Palo Alto Calif.), issued Sep. 19, 2000, titled: Prolonged release active agent dosage form adapted for gastric retention abstracts the present invention which is directed to an active agent dosage form which is adapted for retention in the stomach and useful for the prolonged delivery of an active agent formulation to a fluid environment of use. The active agent dosage form is a polymer matrix that swells upon contact with the fluids of the stomach. A portion of the polymer matrix is surrounded by a band of insoluble material that prevents the covered portion of the polymer matrix from swelling and provides a segment of the dosage form that is of sufficient rigidity to withstand the contractions of the stomach and delay expulsion of the dosage form from the stomach until substantially all of the active agent has been dispensed.

f. This patent goes beyond, what is considered "encapsulations" by further controlling release rates into the stomach and then following the trickling down effect. Taking this to the next level it is conceived that within this matrix are encapsulations which then can drop and do their job farther down the GI tract in combination with the below information provided by the "Alza" patent.

g. Controlled release dosage forms that provide for prolonged delivery of active agent formulations to the environment of use have found application for increasing numbers of active agents. However, with respect to pharmaceutical and veterinary active agent formulations, there has been a need not only to provide for prolonged delivery of the active agent over time, but also to provide prolonged delivery of the active agent at a particular location or locations in the environment of use, such as in the stomach.

h. Certain active agents are absorbed primarily from the small intestine. Generally, the time of passage of different particles through the small intestine does not vary significantly, and passage is generally independent of food intake and particle size. Thus, active agent dissolved in liquid, solid active agent dispersed in liquid and relatively larger delivery units of active agent, such as microcapsules and the like, will traverse the length of the small intestine in substantially the same time frame, usually about 3–5 hours. For active agents that are not easily absorbed by the small intestine or that do not dissolve readily, the window for active agent absorption in the small intestine may be too short to provide a desired therapeutic effect. This fact often creates a need for frequent dosing of active agent in order to provide and maintain adequate levels of active agent in blood plasma. The need for frequent dosing presents compliance problems and is often inconvenient for the user as well.

i. Since it has been found difficult to alter the transit time of active agent through the small intestine, some emphasis has been placed on attempting to control the transit time of active agents in the stomach. Most active agents are not well absorbed in the stomach, but even in those instances where the active agent is not well absorbed, the continuous release of active agent in the stomach over a prolonged time period will dispense active agent over that same period of time to the small intestine where it can be absorbed.

25. The object of the invention is to present a fiber-water composition designed for those experiencing pain; Pain Addressing/Relieving Fiber-Water, simultaneously with hydration.

a. There are many conditions for which the body experiences pain so this is just to serve as an isolated window to understand what a very valuable product in the consumer marketplace world-wide it would be to have a fortified fiber-water to address pain, in general, and/or by specific categories.

b. Stress exacerbates pain in most every situation. It is important in fibromylgia, as well as other stress related diseases to reduce the stress. When some people, and/or animals are sick or are in pain they refuse to cat or drink. It is at these times that hydration is essential. (a discussion relating to a stress reduction fiberwater/relaxing fiber-water is in the context of this filing)
Fibromylgia, by some professionals, been deemed to be closely related to chronic fatigue syndrome (CFS). Additional symptoms of this chronic condition may include sleep problems numbness and/or tingling, irritable bowel syndrome (IBS) etc., which all can be considered in any formulation and/or a derivative of that formulation.

c. The constant drinking (sipping) of water with the fiber to speed the elimination of toxins and toxic metals is ideal. With the addition of glucose to normalize the blood glucose level patients may feel more "even", and more relaxed.

d. With the further addition of a natural relaxant that is water-soluble such as theonine, could be of great benefit to patients with arthritis both rheumatoid and osteo as both conditions are painful. (Note: that theonine comes from green tea and the fact that the drinkers sip, and many times multiple cups throughout the day it may have a cumulative effect in this manner.

e. The inventor, throughout all these enhanced fiber-waters acknowledges the "cumulative effect" as opposed to bolus dosing, regardless if it is a prescriptive, nutraceutical, dietary supplement and/or the like.

i. The inventor calls attention to Nonsteroidal Antiinflammatory Drugs: These drugs may be used to relieve pain. Some are available as over-the-counter medications. Examples include naproxen (Aleve, Anaprox, Naprosen), ibuprofen (Advil, Bayer Select, Motrin, Nuprin), and piroxicam (Feldene). These medications are generally safe when used as directed, but can cause a variety of adverse effects, including kidney damage, gastrointestinal bleeding, abdominal pain, nausea, and vomiting. The inventor believes that delivered in a liquid medium such as fiber-water and/or enhanced fiber-water will potentate the pain addressing effect of the medication and at the same time assure that plenty of fluids are simultaneously taken so as to avoid many of the side effects of "that pill sitting in the stomach" with too little fluid.
  ii. Other supplements of value for CFS maybe in the form of Vitamins, Coenzymes, Minerals, such as; adenosine monophosphate, coenzyme Q-10, germanium, glutathione, iron, magnesium sulfate, melatonin, NADH, selenium, l-tryptophan, vitamins B12, C, and A, and zinc.
  iii. Plants are known sources of pharmacological materials. Herbal preparations that have been claimed to have benefit to CFS patients include: astralagus, borage seed oil, bromelain, comfrey, echinacea, garlic, Ginkgo biloba, ginseng, primrose oil, quercetin, St. John's wort, and Shiitake mushroom extract. Some herbal preparations, notably comfrey and high-dose ginseng, have recognized harmful effects, ergo low dose and continuous supplementation is advocated.
  iv. All the above points to a very valuable product in the consumer marketplace world-wide
26. The object of the invention is to present a fiber-water composition designed for experiencing gout, simultaneously with hydration.
  a. Gout, which is a form of arthritis, is a specific condition for which water is essential. It is critically important to dilute the urine and promote the excretion of uric acid. In fact it is recommended by Anne Simmons M. D. that individuals with gout consume 8 oz. of water with each meal and at least 8 oz. between each meal and after supper.
    i. If overweight it is essential to loose those extra pounds and therefore diet fiber-water-glucose is ideal. (Weight loss reduces uric acid levels)
    ii. Gout can lead to kidney stone formation and must be taken seriously
    iii. All the above points to a very valuable product in the consumer marketplace world-wide.
27. The object of the invention is to present a fiber-water composition designed for those experiencing depression: Mood Elevating and/or Anti-depression Fiber-Water, simultaneously with hydration.
  a. By the year 2020, depression is projected to become the second most common cause of disability among persons of all ages and both genders worldwide. In any given one-year period, 9.5 percent of the population, or 18.8 million American adults, suffer from some form of depression. Women in the U.S. experience depression about twice as often as men. Women buy more bottled water than men.
  b. Regardless of the cause of depression it can cause a slowdown of the entire digestive track. Therefore specific fibers may be called for to help counteract this along with other constituents (especially water).
  c. There are pharmaceuticals with address depression such as: serotonin reuptake inhibitors such as fluoxetine (Prozac), sertraline (Zoloft), and paroxetine (Paxil); venlafaxine (Effexor); trazodone (Desyrel); and bupropion (Wellbutrin).
  d. One of the additional ingredients used today is St. Johns Wort. It is far better, and with less side effects than taking prescription drugs. In fact this herb has been called a natural Prozac. However the public by and large does not know how to take this herb. It is essential that St. Johns Wort, as is true with many herbs, it must be taken daily and throughout the day whereby over time benefits are recognized.
  e. Sam-e
    In a nutshell, SAM-e (short for s-adenosylmethionine) is formed from the essential amino acid methionine and adenosine triphosphate (ATP). SAM-e can be found in every living cell, and is a methyl donor in over 100 different reactions catalyzed by methyltransferase enzymes. Via enzymatic transmethylation, SAM-e plays a role in the formation, activation, or metabolism of neurotransmitters, hormones, proteins, and phospholipids.
    As a mood enhancer, SAM-e functions by donating its methyl group to CNS acceptors through transmethylation and increases the activity of neurotransmitters like dopamine and serotonin. It also improves receptor function linked to phospholipid methylation.
      i. SAM-e is shown to be an effective antidepressant without the side effects often associated with several prescription treatments such as weight gain, dry mouth, loss of libido, insomnia, etc.
      ii. SAM-e is shown to reduce depressive symptoms in as little as 7 days
      iii. SAM-e levels in the blood increase in relation to the degree of mood improvement in depressed patients, regardless of the type of treatment
      iv. SAM-e is shown to be effective in reducing or relieving the signs and symptoms of postpartum psychological distress
      v. SAM-e is shown to be effective in treating depressed postmenopausal women
      vi. SAM-e is shown to be effective in reducing prolactin levels in depressed patients—high prolactin levels are associated with decreased libido
      vii. SAM-e is shown to be effective in treating depression in patients with Parkinson's disease
      viii. SAM-e is shown to be effective in treating depression in patients with HIV
      ix. Thus fiber-water-glucose is ideal. If to make the most tasteless and effectual product possible the science of encapsulations might best serve this purpose.
      x. All the above points show that this variation alone can be a most valuable and profitable product in the consumer marketplace in the United States, world-wide as well as the inventor is looking at the approximate 18,000,000 Americans suffering from depression alone (non related to any specific condition as exampled with those above (under Sam-e which are HIV positive, Parkinson's, Women who are post-partum, and also women who are post-menopausal)).

Conclusion Statement as Related to Health Issues

There are a myriad of other specific health conditions that can be addressed by putting additives into fiber-water ergo creating new and novel fiber-waters with the enhanced deliver systems. Fiber-water, and now delivering additives, using the versatility of these deliver systems within the invention, namely encapsulations and viscosity changes. Ingredients can be delivered through water with fiber(s) and the conditions to be addressed categorically are huge. Besides what is listed here the following are to be included as thoughts but not just limited to these: allergies, headaches, eye problems, PMS, menapause, Lupus, MS. MD, cancers, Menieres, Raynauds, shingles, Wilsons, celiac, those easily bruised, parasite and yeast infections, edema, and more . . .

Segmentations of Markets by Age:

Focus of The inventor is most focused in the next section on children, as they grow from babies through maturing teenagers, as well as the needs of pregnant and/or lactating mothers eventually our aging population known most commonly as seniors. The inventor notes the following:

Infants also have distinct fiber requirements. Until recently, no specific guidelines for dietary fiber in children were available. Recommendations have recently been developed, based on age, weight and height of the child. It is now recommended that children older than two years consume a minimum amount of fiber equal to the age plus five grams a day. The recommended safe dose is between this and age plus ten grams a day. Above that symptoms of excess fiber (e.g., loose stool) may become apparent.

It is the intent of the inventor to provide in addition to various grades of fiber-water the enriched fiberwater, which will serve the basic fiber-water intent, and then magnify/amplify additional added benefits.

Since infants and small children are generally unable to directly tell us of their digestive distress, constipation and other results of inadequate fiber are often exhibited as fussiness or similar undesirable behavior. (This is especially true when infants are just being weaned from fiber-free milk to a fiber containing diet. There can be significant advantage to providing a fiber source in the water along now with additional specifically designed functional additives to be consumed by the infant).

Infants and many small children cannot tell us of their feelings either but they learn quickly that if they cry know if they cry Because infants have a constant requirement (not necessarily a desire) for water, the addition of fiber-water with the enhancements to the typical diet can provide a more constant, even source of nutrition and condition addressing additives while ensuring adequate hydration and fiber given.

Further the use of fiber-water can ensure adequate fiber without adding significant calories—an inevitable consequence of other fiber sources. Consistent dietary fiber can provide for a "more even" operation of the infant's digestive tract while the additives and the viscosity changes serve their purpose. In contrast, a more traditional infant diet that alternates between low fiber formula and high fiber adult foods may have, as an example, an uneven or cramping effect.

A useful amount of soluble fiber is ¼–1 gram per 8 oz (considerably lower concentration than for the adult fiber-water).

Sometimes we don't think that babies and young children have stress in their lives also. Changes in custodial care, baby sitters, new sibling (s), and/or a step-parent, changes due to normal childhood illnesses, colds, flu, teething, fever, measles, mumps, chicken pox, etc. While these illnesses may not be the direct cause of constipation they may be the indirect cause. With illness come changes in eating, sleeping, behaviors, and habits. Travel—when a babies environment is changed, from going to grandparents to international travel, sensitivities to the new, can throw off a system that is used to regularity. International travel bears with it the dehydration of long hours on an airplane etc. The future holds even more stressing travel such as space travel. Dysfunctional homes where there is divorce, alcoholism, family abuse etc., may be noted in the babies, or young child's, refusal to eat, defecate, crying spells etc.

Water probably can be given as early as one month, although usually started between 2–4 months after birth. Fiber-water with the added nutrients and their delivery methodology further can serve as a great pacifier and satisfy the babies need to suck and/or be fed. This is especially valuable during off feeding hours: or in place of hard plastic and/or rubber pacifiers that may cause harm.

Of major importance is the fact that many babies who are given water are given water that is unsafe. This invention insures that the water is safe. Diarrhea, which is often caused by contaminated water supplies, can be life threatening to infants. Therefore, there are great advantages to using safe bottled water for any infant and/or infant formula, etc. In the case of the fat baby this invention may well do more than provide a low or non caloric-hydrating agent. The soluble fiber in fiber-water alone without additives (such as increasing the viscosity) has been show to slow the absorption of fats and sugars (see U.S. Pat. No. 5,505,981).

At every stage of life, fiber is vital to proper health, growth and development. Infants and toddlers require a regular and controlled source of fiber as well as other nutrients. After babies cease to breast-feed or use liquid formulas and move on to more varied adult solid foods, they often suffer a number of painful digestive episodes which makes them fussy and difficult. Because fiber-water, itself, and with this invention provides an ideal source of hydration, fiber, and other additives for such infants, it may be added to commercial formulas and/135-1 or used alone.

Therefore, not only does it ensure adequate hydration, it also provides a consistent fiber source to guarantee regularity. It should be kept in mind that typical commercial baby foods may vary widely in the amount of fiber provided and also the nutrition they provide generally yet alone when specifics are called for. This invention provides an opportunity to lay the foundation of good habits and additionally, it may be beneficial to add to commercial baby food if deemed appropriate.

As the infant becomes a toddler and moves towards more a more adult diet, the requirement for fiber and other additives increases and/or changes and this inventor is sensitive to that.

28. The object of the invention is to present a fiber-water composition designed for babies. Enhanced Baby Fiber-Water, simultaneously with hydration.

At certain times babies want to be fed more frequently than at other times. This could be due to growth spurts, the good feeling of mother (using mother as a sort of pacifier), and/other possibilities including but not limited to illness etc. There it is important to have an alternative yet healthy addition and/or substitution for the breast/bottle.

Fiber-water is an excellent choice but in this invention where we go beyond the inventor lists some additional enhancements using encapsulations, viscosity changes or a combination of both.

a. Babies who are hungry all the time and/or need oral gratification can now have a slightly thicker fiber-water whereby they have to draw harder on the nipple (although the nipple hole can be enlarged) which will not just give them a feeling of fullness but will tire their little mouth and jaw muscles.

b. In order to get a well-balanced nutritional delivery to babies who are not breast fed formula is used (or in combination with breast feeding). While this is desirable and important often nutrition is needed without the calorie contributing additions. By encapsulating (micro-encapsulating) supportive health additives, with or without viscosity changes, and/or with or without a small addition of glucose, a baby can receive beneficial nutrition to support development.
  i. Calcium is a good example and can be added to the enhanced fiber-water, with or with out viscosity changes and/or encapsulations. (Babies, and through about age three (3), 500 mg. of calcium is needed daily)
  ii. Fluoride for the eventual eruption of teeth
  iii. Doctors prescriptives
  iv. Any enriched fiberwater may be used in any proportion to dilute, augument a formula.
    Additionally, there have been many new discoveries in more than just nutritionally enhancing infant formula. U.S. Pat. No. 6,399,090 to Shehadeah, Insotech, (IL), issued Jun. 4, 2002, Again it is important to notice the effect that sodas, and drinks which are extremely high in sugar, have negative effects on the body. Further, giving children so much sugar at an early age sets up their taste buds to crave sweets and therefore select more sugary foods. It is also noted that excess amounts of sugar on a continuous basis at an early age can set the metabolism towards a diabetic-prone posture later in life. Hyperactivity along with other unfavorable conditions in children has been caused by an over load of sugar laden foods and beverages that act like "liquid candy". Fruit juices are also very high in sugar, although they may contain a different kind of sugar. Even those new age beverages with their fancy names and deluxe packaging, for the most part, are mostly sugar water.
  v. US. Pat. No. to Shehadeah, Insotech, (IL) tided: Insulin supplemented infant formula teaches an infant formula in a powder or solution form including those important nutritional components along with an insulin supplement. According to one aspect of the present invention is such that when the infant formula is fed to an infant a chance of the infant of developing diabetes is reduced. (wherein said insulin is in a concentration range of about 1,000 to 100,000 micro units/100 ml of solution or 8,300–750,000 micro units/100 grams of powder)

29. The object of the invention is to present a fiber-water composition designed for toddlers and young children, simultaneously with hydration.
  The inventor again must remind the reader of her adversity to sugar. Again it is important to notice the effect that sodas, and drinks which are extremely high in sugar, have negative effects on the body. Further, giving children so much sugar at an early age sets up their taste buds to crave sweets and therefore select more sugary foods. It is also noted that excess amounts of sugar on a continuous basis at an early age can set the metabolism towards a diabetic-prone posture later in life. Hyperactivity along with other unfavorable conditions in children has been caused by an over load of sugar laden foods and beverages that act like "liquid candy". Fruit juices are also very high in sugar, although they may contain a different kind of sugar. Even those new age beverages with their fancy names and deluxe packaging, for the most part, are mostly sugar water.
  a. It has been documented that soluble fiber is important for children of all ages. Now with the next level of development of fiber-waters one can readily see the value of a line extension for this age group and further considering this to be a very valuable product in the consumer marketplace world-wide.
  b. Additions for young children would include calcium (ages 4–8 years 800 mg. is recommended and 9 years upward 1,200 mg. is the recommendation. The just said is just one example of a value added enriched-fiberwater for children.
  c. Other than growing healthy, addressing health challenges such as illness and disease there are other conditions that are considered. Over and over literature is replete, addressing concentration by school age children. While some of them have been diagnosed as having Attention Deficit Disorder (ADD) others as hyperactive, diet is believed to play an important role.
  d. By the caretaker/mother becoming more aware of the essential needs, on a daily basis for water and fiber and good nutrition it is the hope of this inventor that this awareness will continue, and pass to the child who eventually will make part then in total his/her own choices and decisions as he or she grows and develops. It may also be noted that the father, possible siblings along with other family members and friends become more aware of this invention, and so by this invention it is the goal of this inventor to create healthier people.
  e. While enhanced fiber-water may be packaged in any container and under the conditions designated by governmental health standards the inventor considers the packaging of such fiber-water and/or an enhanced formulation for children, especially young children, to be packaged in flexible pouches or laminate boxes for several reasons, including the dangers of glass containers, or the less likely to spill of a wide mouth cup. Additionally, the child is less likely to put potentially dangerous ingredients and/or small objects into a wide-mouth drinking container thus creating potential dangers in swallowing the just mentioned.
  f. As with any fiber-waters, it is advantageous to provide the infant and child (any age) fiber-waters in a number of strengths so that the amount of fiber administered can be readily monitored and appropriately adjusted on an individual basis. Again, it may be advantageous to add identifying color so that it is clear to the parent/caregiver (or the user) precisely which grade of fiber-water is being used. In the case of children especially, (actually anyone) the color may be so inherently appealing therefore may mitigate in favor of using transparent packaging so that the child can appreciate the color of the fiber-water being consumed. A popular noted expression has to do with fooling the eye (trompe-l'oeil) and here the inventor believes that color is distracting, especially very vivid, and may override taste.
  g. It is also conceivable that if the container is not transparent that a transparent straw may show the color, or that specific graphics and/or color on the container will relate to the strength (apart from the aesthetic appeal of the color or graphics).

30. The object of the invention is to present a fiber-water composition designed for teenagers, simultaneously with hydration.
  a. The importance of creating a fiber-water with additives for teenagers cannot be overlooked. This is especially true if they have significant health issues. The inventor would be remiss if she did not at least mention this concern about what this age group consumes. This age group, in their search for their independence, are most inclined to make their own selections, and additionally much of their drinking is away from home. They are most influenced by media and peers. A strong effort should be made to provide color, essences, and packaging to address this age group in their language.

b. Teenagers especially are known not to eat much fiber and/or to hydrate with water. Many times they skip meals, especially breakfast, and so with the drop in blood sugar they cannot function well in school. On the opposite end of the spectrum teenagers consume too much sugar. (see obesity and diabetes) Many behavior problems are due to too much sugar and/or too little glucose. Schools now allow students to keep a container of water at their desk. Fiber-water and/or this invention is most suitable/perfect for those students. Specific areas of concern for this population includes, but is not limited to the following.

c. Pimples and acne are embarrassing and cause much stress. While some 85% of teenagers between 12 and 25 experience acne most outgrow the condition over time. Pimples and acne are not just a condition of the teenagers, but some 10% of Americans between 25 and 44 have the same problem. Several population studies suggest that eating more fiber can help with this condition by improving the conditions within the body and eliminating toxins.
  i. For those with acne zinc has been shown to have a significant benefit. In one study people who took 135 milligrams of zinc everyday for 12 weeks saw 85% of their blemishes disappear. Zinc works by reducing blood levels of the male sex hormone dihdrostestosterone (DHT). Small amounts of zinc added to the invention and with multiple bottles of water consumed daily so as not to exceed 30 milligrams of zinc daily (without doctors permission) it is conceivable that there could be a reduction in blemishes.
  ii. Eczema, a serious skin condition, has been known to be helped by the regular addition of zinc to the daily diet.
  iii. All the above points to a very valuable product in the consumer marketplace world-wide 31. The object of the invention is to present a fiber-water composition designed for seniors and looking at the anti-aging market, simultaneously with hydration.
  a. While there has been a great focus in relation to children and the younger generation, this invention no way limits itself to that marketplace. Infants, young children teenagers pose need/desire/compliance friendly challenges and the aging population, senior citizens, "seniors" another. As related to seniors:
    i. Aging seniors who do not want to take so many pills, etc,
    ii. With aging comes the loss of ones thirst mechanism ergo seniors may not get enough hydrating liquid.
    iii. Many seniors are use to bottled products ergo recognition (just as they do with in tea bags under the inventors PCT) So herein lies the opportunity to add all the extra benefits, to fiber-water governed under this invention to the just mentioned familiar bottle, can, pouch box and/or the like . . . easily recognizable object.
    iv. Now it is not only possible, but often desirable, to use this invention. As a psychological advantage, a patient might not feel as if they are so ill as when they have to take so many medications. Also whereas if they were directed by a health care professional to take a pill, they would not do so and/or pretend to do and hide, or flush it down the toilet, etc. just like a child. While the inventor believes that information is important many just can't absorb it and become fearful, especially the aging. To prevent confrontation and tension in this age group as well, care-givers hope for delivery systems, in which there is the opportunity to mask not just the taste but the active ingredient(s) so as to reduce questioning by the patient. The inventor has first hand experience with her 91 year-old Mother in relation to on going cardiovascular, urinary, depression, problems needing attention daily.
  b. Using further, seniors have problems often times with gastric upset and other digestive disorders whereby in the wrong from and/or too much entering the stomach too quickly without adequate fluid may be problematic.

32. The object of the invention is to present a fiber-water composition designed for those participating in strenuous activities/athletics Sport Fiber-Water Snapshot™, simultaneously with hydration.
  a. It is conceivable that their be a formula with, and one without, glucose that may have encapsulations, viscosity changes, and/or both. Minerals largely make up the isotonic meaning and they really do not, for the most part taste good and/or may, in some forms be taste acceptable but not in the form most desired for this intention
  b. Several decades ago French scientists formulated the hypothesis that fatigue is caused by inefficient energy metabolism at the cellular level. They believed that enriching the cellular environment with the appropriate substrates and co-factors could promote greater metabolic efficiency and thereby reduce the subjective symptom of fatigue. The potassium and magnesium salts of aspartic acid were considered ideal for this purpose.
    i. Potassium is involved in energy metabolism and in repolarization of muscle cells.
    ii. Magnesium is required for synthesis of ATP and it also enhances transport of potassium into cells.
    ii. Aspartic acid (AA) is converted intracellularly, in a series of steps, into oxaloacetate, an important substrate in the energy producing Krebs cycle. Potassium and magnesium aspartates thus appear to provide several essential cofactors for energy production.
  c. Designing a sports form with fiber-water as the base will rely on encapsulations, viscosity changes (and maybe more than one) and the importance of hydration.
    i. There is much supporting science documenting isotonic beverages and that science is to be considered when formulating here.
    ii. Further what is known is that it is important to keep up the blood glucose and extend by encapsulations and/or with the fiber(s) used/blended the postprandial rise in the just said.
    iii. The formulations may be divided into gender specific products and/or by weight and/or by age.
    iv. The formulation may be mixed in any ratio with a Ready to Drink Sports Drink, such as Powerade Gatorade® All Sport® etc. This may be a way to formulate for individual who weigh less and/or are younger.

d. While it would be very intense if Sports FiberWater was added to reconstitute a powdered formulation of the just said, or another in the category by having ingredients encapsulated for later/delayed time release this would prevent the "all at once" dosing upon drinking.

e. It is also possible to use any ratio of this enhanced fiber-water, pure water and the concentrate to form a custom drink. This allows the consumer to have a broad range of choice as is evident f. All the above points to a very valuable product, and spin off products, in the sports drink category, which is of major importance in the consumer marketplace world-wide 33. The object of the invention is to present a fiber-water composition designed for pregnant mothers. "Mama to Be" Fiber-Water, simultaneously with hydration.

a. In pregnancy nutrients, hormones, toxins can have a profound effect. Folic acid has been shown, as an example of a vitally important nutrient in pregnancy to prevent a significant reduction of neural tube difficulties including spina biffida. Folic acid needs to be present at the moment when an embryo's cells curve over one another to create the neural tube. 400 micrograms is what is recommended and as experts advise should be a daily supplement for every woman of child-bearing age.

b. In the first 12 weeks of pregnancy is critical to have more than the required 8 glasses of water. The current recommendation is 10 glasses.
  i. Mothers-to-be sometimes suffer from nausea and vomiting. It is important to be sure to replace with water if fluids are lost. This is also true to some degree with the addition of a small amount of glucose especially if the mother-to-be is vomiting extensively as glucose levels are affected by vomiting. A special diet-fiber-water-with glucose for pregnant women who need to increase their water and fiber intake along with foods to support both maternal and fetal needs and ensure a healthy baby and mother.

c. It is also most critical to remove toxins on a regular basis for her health and the health of her yet to be born baby. The fiber-water invention will aid in the removal of such toxins. Further, with the addition of small amounts of glucose to the water and fiber we can best assure the "evenness" of blood glucose levels for both mother and fetus as mentioned. Of specific importance to pregnant and then lactation mothers is a strong immune system, the expediting of the removal of toxins from the body. It is very important to give the pregnant mother natural ingredients that will accomplish the just mentioned without the addition of chemicals for, more than, obvious reasons.

d. All the above points to a very valuable product in the consumer marketplace world-wide 34. The object of the invention is to present a fiber-water composition for lactating mothers, simultaneously with hydration.

Breast feeding fiber-water for new Mothers.

a. Specific water for lactation is important to provide nutrients to the newborn through breast milk and for the care of the mother postpartum. Women who are breast-feeding need to drink fluids especially safe water. Since both with pregnancy and lactation the mother is usually somewhat restricted in exercise the soluble fiber enrichment becomes even more significant, especially if ingested regularly as suggested throughout the day and on a regular basis.

b. There are mothers who use a breast pump to extract the breast milk for later feeding. This may take on a new position if one looks carefully at combining said breast milk with fiber-water and/or an enhanced fiberwater with specific intents such as: enhancing nutrition addition hydration cutting down on calories c. All the above points to a very valuable product in the consumer marketplace world-wide as noted by all the children being born, and the continued belief that breast milk offers many benefits that a commercial formula doesn't. most important is the immune enhancing abilities.

35. Object of the Invention is to present a series of Animal and Pet Products, simultaneously with hydration.

a. Animals, mostly domestic pets, are often forgotten when it comes to supplying, as an example, healthier alternatives. This is not always intentional especially with tight budgets and time restrictive schedules of "working" owners or in the case of large families etc. The ability to bring to market products just for human consumption alone is most difficult yet alone for pets and/or other animals. Then too it is noticed how many individuals take better care of their animals than they do themselves.

b. Animals, especially personal pets, and additionally all the "aid dogs" (for the blind, police K9 dogs,) etc. are a major part of our society bringing help, joy, pleasure, companionship, etc. to the lives of young and old alike.

c. Some pets have become so much a part of the family that they even sleep in the same bed, travel with, and/or the like with their owners. Further, now pets are even being brought into hospitals and other institutions to visit patients.

d. Pet health is very important, however at the same time it is big business. As a business, and to bring to the marketplace well-studied ethical nutritional products one is faced with many of the same problems that face the people population. Sometimes even more, because there are many categories, which compose the animal kingdom, and this invention is not limited to what is normally considered being just the ordinary household pet.

e. While it is true that pets might have some fickle tastes along with individual preferences when it comes to their food they still need nutrition and care in relation to specific conditions.

f. To get medication including but not limited to even some vitamin preparations one only has to look at what it takes to get this into a pet. Pills have been buried in bits of food more often than not. Besides it is very difficult to offer a trip to Disneyland® to your dog.

g. The inventor has noticed a great sensitivity to pet nutrition by many companies especially the Iams Company® (Dayton Ohio) with reference to the following U.S. patents: U.S. Pat. No. 6,039,952 to Sunvold, et al., issued Mar. 21, 2000, titled Composition and method for Improving clinical signs in animals with renal disease; U.S. Pat. No. 6,204,291 to Sunvold, et al., issued Mar. 20, 2001, tided Process for promoting weight loss in overweight dogs; U.S. Pat. No. 6,180,131 to Sunvold et al., issued Jan. 30, 2001, tided Process for improving glucose metabolism, satiety, and nutrient absorption in companion animals; U.S. Pat. No. 5,776,524 to Reinhart, issued Jul. 7, 1998, titled Process for treating small intestine bacterial overgrowth in animals; U.S. Pat. No. 6,133,323 to Hayek, issued Oct. 17, 2000, titled Process for enhancing immune response in animals using .beta.-carotene as a dietary supplement.

h. Additionally, U.S. Pat. No. 5,968,569 to Cavadidi et al. (Nestec S. A., (Vevey C H), issued Oct. 19, 1999, tided Pet food product containing probiotics;

i. U.S. Pat. No. 5,294,458 to Fujimori (Maruha Corp. Tokyo JP), issued Mar. 15, 1994, titled Pet food— where this invention contains lactosucrose to keep the intestines of the pet in order, provide a good taste and a great effect on deodorizing feces and urine discharged by the pet.

j. The importance of fiber-water for animals has been stated (U.S. Pat. No. 6,248,390) and this invention for animals is to provide an enhanced fiber/water/liquid following the guidelines as for humans while providing hydration along with other active and/or non-active ingredients.

k. This invention for animals relates to the ability to directly give enhanced fiber-water. Additionally and perhaps more common might be the ability to give in-directly (mixed in food) an enhanced fiber-water following the guidelines of the invention ergo creating a superior product addressing desires and/or needs, and/or both for the animal. This beneficial liquid (unlike adding liquid vitamins and/or the like) will increase hydration with the added feature of one or more beneficial agents to treat a specific condition, performance desire, promote general health and/or the like.

l. Animals have many of the same problems as humans as far as the following: viral and/or bacterial infections, and/or inflammatory conditions, and/or the like. Additionally certain animals, such as dogs, as well as humans, sometimes suffer from diabetes, or have an impaired ability to regulate blood sugar levels. Once diagnosed, they have to be closely controlled by diet, medication and/or both.

m. Certain animals also have a tendency towards excess caloric intake, which increases, as in humans, the risk of the animal developing not just diabetes but other chronic diseases. It would be more than just desirable to manage caloric intake through dietary means so that the animal would become sated after meals but without excessive caloric intake.

n. Animal by and large do not eat for social purposes nor do they follow the psychological (often pathological) patterns so associated with humans and their food behaviors. Therefore, by this invention much can be offered to the animal kingdom.

o. Additionally there are numerous, and far too many well-designed examples of all sorts of additives being used for animals which are, and/or do produce food for humans and other animals. (e.g. chickens, cows, pigs etc.) Careful consideration must be given to animals, which are "eaten" and also of the food that they produce for eating (eggs) and/or both.

p. Further there exists a special group of nutritionally engineered products for, what the inventor calls, competitive animals such as racehorses, polo ponies, greyhounds (comparable to human athletics as just an example) etc. An extension would be show animals of all types, and working animals on ranges and farms. Further would be animals specifically for breeding. With the encapsulations much nutritional fortification is possible.

q. In our zoos and circuses we have in captivity many wild animals, birds, etc. for which humans are responsible for their nutrition.

r. With a consciousness towards the best way to deliver, in all the categories of supplementation as described for humans (people), one is reminded that animals do drink everyday. It is also noted that quite often liquid is needed to wet animal food by necessity, design, or both . . . ergo imbibing the food with additional liquid. To use such products to mix in animal food is a most lucrative market. (Any packaging is applicable)

s. For a better explanation is . . . more specifically, pet foods for dogs and cats, as an example, is usually classified into
  i. a dry type, a semi-moist and often called a soft dry type and a wet type. In all these instants, liquid can be added. The dry type pet foods include, as an example, a moisture content of below 10%–12% in forms such as kibble, biscuits, flakes, crumbles (granules).
  ii. Semi-moist usually have a moisture content ranging from 25%–35% and are in the form of hamburger, ground meats, fowl, and/or the like.
  iii. The wet type food includes food having high moisture content of 70%–85%, whereby many canned foods and, those that have undergone a retort process method fall into this category. There are oatmeal type foods comprising of meat and fish, as well as those that have additionally added vegetables and vitamins, and/or the like added additionally.
    (1) If the liquid has a flavor in it, which will mask the unappealing tastes of many of the aforementioned ingredients and/or elements as described for humans with and/or without encapsulation(s) and/or viscosity changing technologies then there exists a greater chance of compliance.
    (2) If the encapsulation are large (example like a gummy ball to be chewed) then not only can they carry additional fiber (with the benefits of) but within this invented large encapsulation, many additional encapsulations (with one or more active ingredients) which can be immediately released and/or timed released (according to the digestive tract of the particular animal/pet/species/size/weight and/or the like), are considered invented.
    (3) Further, even animals have fragrance preferences by nature and/or learned. For a cat one could envision a fish smelling water the inventor just doesn't know what kind of fish as of yet. Conceptually this can extend throughout the animal, bird, and even reptile communities.
    (4) It was a real learning experience for the inventor to study animal habits, preferences and pet food products for the specific goal of inventing/designing for this enormous category good tasting nutritious healthy product(s)/additives. Again it is important to note that the members of the animal kingdom do not require fancy packaging for which so much extra monies are spent, and therefore most profitable to the producing/owning entity while providing the best in nutrition/supplementation for the user.
    (5) Addressing bowel regularity to ensure hydration and regularity again of domestic animals— primarily cats and dogs. However, any carnivore or omnivore should benefit from the invention. Herbivores have very different gut bacteria and may be able to metabolize the soluble fiber. Therefore, these animals must be tested on a case-by-case basis. Domestic animals, particularly cats and dogs, also suffer from problems with hydration and constipation. Dogs are omnivorous and will naturally consume some fruits and vegetables. However, refined dog foods tend to be remarkably deficient in vegetable fiber. Administering a source of fortified fiber-water daily (with additional additives addressing the GI Tract) using water as the delivery system, since dogs etc. generally drink offered water can readily alleviate this problem.

iv. The inventors experiments showed that by adding just the fiber water to dry kibble (or as an example, the gravy forming type) or even stirred into canned dog food have shown that it has gone unnoticed by dogs, cats, and other animals.

v. Cats also have serious dehydration and constipation problems. Cats are obligate carnivores and generally will not knowingly consume fruits or vegetables (other than valuable houseplants). Kidney failure is a common malady of geriatric cats resulting, in part, from inadequate hydration.

Constant vomiting is a common feline problem brought on by their grooming during which they ingest significant quantities of fur. In the wild, cats ingest sufficient indigestible matter (bones, cartilage and tendons) to provide non-vegetable fiber. With pet cats the owners are expected to mix fiber (generally psyllium) with the cat's food or administer petroleum-based laxatives. Neither alternative is particularly ideal. Thus this invention, as well as Fiber-water, can be given as "water", or mixed with the cat's food to provide sufficient fiber to prevent both hairballs and constipation thus solving significant feline problems. It appears that reduction in vomiting positively contributes to the hydration of cats.

36. Daily water program and/or incremental enhanced fiber-water, or any liquid delivery program by design for humans and/or animals: (regardless of the desire(s)/need(s)/condition(s)), simultaneously with hydration:

The inventor has covered bolus dosing as well as spreading out the deliver of actives through the day as being, in may instances, advantageous.

a. Presented here in specifics is a daily and/or incremental program, regardless of the category addressing (user . . . desire/need/condition . . . matrix appropriate), whereby delivery may be:

i. in multiple sets as with, example, a 2,4,6, or more 4 set/pack with a specific daily purpose and always including hydration as a main goal) as example they may include different but not related and/or different but related (as exampled with a daily supply of RDA vitamins and minerals which might be served/spread over a designated period of time (e.g. 12 to 24 hours).

ii. An integrated program for weight loss might include but not be limited to (1) A multi-pack (regardless of containers) rising water for the first thing in the morning, one or more throughout the day, then the retiring water . . . the last before bedtime. (The amount and/or the constituents may vary) Separate containers might be even the same formula but easier to transport . . . and/or again might be packaged in separate containers if the formulations are different (a) Color coded for changes of the time of day, or the ingredients within (b) Viscosity changes for the time of day, for a dieter especially, with or without encapsulations (thicker may mean more fiber and/or different fibers, or thicker but not with fiber, any with or without encapsulations (c) Glucose supplementation (which the inventor knows can be manipulated to taste like water with, as an example, offsetting with one or more acidulates, and/or acid plus other ingredients, or other ingredients with no acid known in the art of formulation.

(2) Multiple servings might be in one large bottle (3) Perhaps there might be 2 bottles, one to last as an example 6 hours and the second to be sipped over the next 6 hours. Can be the same or different formulas.

iii. For children especially creativity is important, and for business bringing on not just the sale of product, but the opportunity for licensing and cross promotions with major entertainment and/or "like entertainment" companies etc. can be enormously profitable as well as responsible. The inventor calls attention to the following example;

(1) In relation to a "fireman theme" by packing small individual bottles/containers/(containers that have graphics are more attractive to children . . . but clear is suggested if there is to be a reaction in the packaging that the child will want to observe), in a fire station and/or in a fire-truck, and/or in a fire-truck in the fire station as a double incentive.

(2) Now we are starting to notice that with one unit it is possible but with more than one it brings in the toy element, games, collectables, tradeables etc. which can be made of any material, shape, design, indicia, etc. If a treasure to be kept then it is conceivable that there be electronics, lights, noise, etc. added. All considered as part of the creativity and ergo the "inventivness".

(3) The drinks can be different colors for specific reasons . . . Red for fire . . . If with a story blue means that you put the fire out. (Perhaps even included information about firemen and/or the department.

(4) Again of note is that if it for multiple units are packed with the reconstituting liquid regardless of portion size per bottle the container for the unit(s) does not have to be metal or plastic; graphics on a paperboard box and/or a paperboard box tray is also envisioned. Further; if it is presented in a tray like form as opposed to a "closed carton", it could be with or without a continuation of the concept printed on the plastic covering.

iv. It also provides the opportunity for additional literature, advertising and/or the like. Literature of all sorts, not just as related to the theme may be included in any form, promotion, game, contest and/or the like.

v. The size may be one serving and/or more based on 8 oz. per serving and/or perhaps scaled down appropriately for a child as in relation to age. (e.g., in lots of 4,6,12,24, etc. whatever to be used through out the day, week, month.

vi. Even a case a week or a month club with a different theme and can be delivered as a business method for the home delivery companies and/or sold off of the internet. It can work as "pay as you go" and/or on a revolving charge.

vii. They also can be of the same nature and/or an assortment of different containers with different natures with and/or without the same intent and/or interrelated intent like.

37. The object of the invention is to present other forms of the liquid, simultaneously with hydration, which might fall (classified by some) into one or more of the following categories known by the descriptives: Concentrates, Needs reducing; Elixirs, Usually a sweetened medicinal solution; Tonics, Usually considered to be anything that refreshes. In different parts of the world references are different. The inventor for this purpose uses the word "LIQUID" to include all of the just mentioned and/or the like.

38. The use of coloring agents, flavorings, and/or the like, simultaneously with hydration. It may also be desired and/or advantageous/useful to add colors:
    a. To denote grade/strength of one or more ingredients so as to be can be identified at a glance.
    b. To denote product content
    c. For decoration color can be use to attract and/or enhance desirability.
    d. Color may be functional/nutritive. Those colorings with nutritive values include but are not limited to colorings from pumpkin, cacti, lycopene from tomatoes, berries, and cartinoids from the fruit of red pepper.
    e. It is also the object of the invention to use colors of food grade quality so that when the drink is spilled, the color is not permanent. It has been possible to do this with most colors up until now with the exception of green. U.S. Pat. No. 5,993,880 to Frost, et al., issued Nov. 30, 1999 (Kraft Foods Inc.) presents a new form of green color prepared by specially treating copper chlorophyllin. Other colorings of unique value and nutritional value with sound scientific evidence shall be sought and included in the inventive compositions.

39. It is the objective of this invention simultaneously with hydration to incorporate Imbibing and Reconstituting Objectives
    a. It is also a feature of the invention that it can also be used to add the compositions to food. For example, any packaged food and/or beverage can be reconstituted so as to yield an enhanced food and/or beverage with additional elements as herein described.
        i. This means that (and in certain instances to those knowledgeable in the art, as might be with encapsulations) extreme heating is not advisable/ possible but it is foreseeable in many instances that if the enhanced fiber-water is used these foods will also become enhanced.
        ii. If dried or concentrated fruits, vegetables, etc. are soaked in the product, they will become imbibed, as well as softened, and ergo more digestible due to the absorption of liquid.
        iii. Fiber and the specific added enrichments to the liquid can readily be added to all types of packaged food including gelatin products and to canned concentrated foods such as soups (mainly those not requiring heat).
        iv. In addition, the liquid can be frozen to provide enriched healthy ice cubes, crushed ice, pops, etc.

40. An object of the invention is to prevent a diagnostic fiberwater simultaneously with hydration: Fiber-waters for diagnosing for one or more conditions Fiber-water with enhanced fortified substances that are delivered with hydration for beneficial and/or diagnostic agents with the intent and/or designed specifically for permitting such administration with or without functional and/or decorative elements. The deliver of such may be in the background liquid, the viscosity, the encapsulations or any combination of the just said. They may be colored denoting use and/or for decorative purposes and/or both.
    a. Diagnostics, as teeth disclosure of plaque
    b. Radioactivity diagnostics
    c. Diagnostic agents with health-enhancing component(s),
    d. and/or a combination of one or more of the above with or without colors, decorative elements and/or the like 41. Objectives for specific conditions:
    a. Natural catastrophes and emergencies are certainly a source of stress as are medical problems. Numerous and varied medical conditions, both short term and long term, may require feeding an individual through a tube. The two types of tubes used most commonly are the naso-gastric tube and the gastrostomy tube. In either case nutriment is supplied directly into the stomach. The present inventor is a named inventor on U.S. Pat. Nos. 4,315,513 and 4,393,873 for a percutaneous transport tube with a one-way valve for gastric feeding, and is an expert on the subject of conditions and problems related to tube feeding.
    b. Great efforts have been made by major corporations to provide balanced nutritional formulations for specific medical conditions to be used for tube feeding. Depending on the specific medical condition, the severity of the problem, and/or a moment in time, multiple needs may be met including the soluble fiber on which this invention is built.
        i. One of the major short-comings of commercial premixed products is that they do not readily contain enough fiber and/or other necessary additives. There are continuing on going efforts to create tube-feeding formulas that will address this problem. As an example Novartis Nutrition has created IMPACT with Fiber. This product contains 250 calories per 250-ml can and only 2.5-mg of fiber. Also, liquid foods capable of passing through a tube are frequently high in calories and low in fiber and other desired additives might not be appropriate.
            (1) Fiber is important as has been said because patients on tube feedings usually do not get the optimal opportunity, nor amount of physical activities. Such activity is important in stimulating proper functioning of the digestive tract. Therefore one can certainly surmise the additional importance of fiber in the diets of these individuals. The inventor also notes that some patients may have a high requirement for fiber whereas others do not. Therefore, one may administer excess calories in an attempt to provide adequate fiber (and/or other ingredients).
            (2) Depending on the design of the particular tube, it may be expected that the viscosity of the feeding liquid may be a problem, however encapsulations will not present a problem. The inventor has demonstrated the 35 g of soluble fiber mixed with 2 ounces of safe water presents no problem in passing through the aforementioned-patented tube. With the consideration that her inventions possess a one-way valve it is far more difficult to use a viscous product than with the conventional latex tubes which have the additional options of using gravity flow techniques.
(3) Additionally, one must take into serious consideration the fact that nasal-gastric fed patients are more sensitive to being fed continuously, and/or more frequently by the tube. Problem also may occur when the formulation is more viscous. This is especially true in traumatized and overly sensitive patients. Extensive feedings through these tubes may often irritate the throat. This has been addressed and taken most seriously by the inventor.
(4) Whether it is for hospital, home, or travel like situations the ultimate solution for tube fed patients is to supplement the feeding regime with enriched fiber-water based products along with and/or to replace plain pure water.
(5) Fortified fiber waters, as described herein, are:
  (a) Simple and accurate to administer.
  (b) Perfect for designing an individual product especially if they are packaged inn vials
  (c) The resulting liquid can be used as a stand-alone product or mixed with a given formula before delivering it to the patient as a single unit.
  (d) Further, the liquid can be added to the tube line in tandem with other supplementation (see U.S. Pat. No. 5,531,734 to Geckle, et al., issued Jul. 2, 1996, Method of Altering Composition of Nutritional Product During Enteral Tube Feeding, and U.S. Pat. No. 5,533,973 to Piontek, et al., to Jul. 9, 1996, Alteration of Nutritional Product During Enteral Tube Feeding).
  (e) The inventor contemplates that the ingredients, other than the fiber (and not just for tube feedings but for the general consumer marketplace) may remain consistent/the same, but the grades and blends of fiber change. This can be denoted by changes in the color of the liquid and/or the packaging, markings, etc
  (f) It is further contemplated that not only will color denote the strengths and/or types of fiber and/or additives, but to note, that color has often been denoted to coincide with flavor. Thus, to a tube fed patient this addition of color might be pleasing, especially to a child patient, and provide a distraction from an unpleasant situation. Further, since these tubes are not always permanent, and if the liquid colored or whatever liquid experience should mean to the user accomplishes the designed intent, and is both convenient and pleasant the inventor is hopeful that on going use of such fluid will continue on a regular basis. The value of said fluid(s) will be carried forward to promote good health for life.
42. An object of the invention is to enhance the looks "appeal" of drinking water for those who do not like to drink. While the fiber is tasteless, and it tastes just like water some people find that boring, ergo do not drink enough. It is possible then that, as with the additives, the final product presents as fiberwater with decorations. Festive looks such as ribbons, bubbles, dots, recognizable shapes at random or arranged (licensing) and/or the like are most appealing. The inventiveness is to decorate the contents.
  a. One does not often think of "decorative" as an additive of value but is considered to be most definitely here. While container decorations and label decorations are to often attract and, as an example, colored waters attract if they have no other value added enhancements they are of value because the value might be solely for the purpose of:
    i. Attracting a consumer
    ii. Promoting a positive image
    iii. Changing the perceptions of a consumer
    iv. Promoting the "sale"
    v. Differentiating from the competition etc.
  b. The inventor has conducted "look" studies with mainly children using hand sanitizers and hair preparations, which have bubble looking "identifiables", visuals" inside the bottle.
  c. These look good objects may or may not have functions beyond looks.
  d. Decorating liquids would be a proper verbiage and visuals count.
  e. This invention includes any indicia, or more than one, as in duplicating and/or as in more than one representation, in the container, actives/nutritive and/or decorative for brand recognition, advertising purposes, licensing, cross promotions and/or the like.
    i. Most likely this would be in a container whereby the indicia can be viewed through at least one side.
    ii. If not viewable the when the liquid is poured then it/they will become visible in the drinking container.
    in. Or both.
43. It is an object of the invention to provide an adhesive system whereby any portion of the invention (the liquid itself without the companion, the companion, or both) that goes through the oral cavity may stick to the teeth, gums, or any area of the aforementioned cavity and provide the continuous release of one or more active ingredients that may work independently and or in consort to medicate, nourish, support, heal, and/or the like. The delivery system used adheres.
  a. As an example it is possible to provide an anti-bacterial to remain in the pockets of the gums, plaque remover to the teeth in such a way that the "washing over the teeth" will provide ingredients and delivery systems that will stick to the teeth and break down plaque, or even tarter, over a protracted period of time.
  b. As we develop more and more "good guy" organisms to fight the "bad guy" organisms beginning their work in the oral cavity better health will follow.
  c. Certainly this inventiveness can be combined with oral disclosing of plaque, visually, as well as other enhancements working in consort or independently.
44. An object of the invention is to develop a fiber-water with the aforementioned control factors, mainly encapsulations and viscosity changes relating to those with hypoglycemia, acute and/or chronic as a carbohydrate metabolic disorder and/or whatever the cause. Fiber-Water for Hypoglycemics.
  a. Glucose, a form of sugar, is the body's main fuel. Hypoglycemia, or low blood sugar, occurs when blood levels of glucose drop too low to fuel the body's activity.
  b. Carbohydrates (sugars and starches) are the body's main dietary sources of glucose. During digestion, the glucose is absorbed into the blood stream (hence the term "blood sugar"), which carries it to every cell in the body. Unused glucose is stored in the liver as glycogen.

c. Hypoglycemia can occur as a complication of diabetes, as a condition in itself, or in association with other disorders.
d. The normal range for blood sugar is about 60 mg/dL (milligrams of glucose per deciliter of blood) to 120 mg/dL, depending on when a person last ate. In the fasting state, blood sugar can occasionally fall below 60 mg/dL and even to below 50 mg/dL and not indicate a serious abnormality or disease. This can be seen in healthy women, particularly after prolonged fasting. Blood sugar levels below 45 mg/dL are almost always associated with a serious abnormality.
e. The amount of glucose in the blood is controlled mainly by the hormones insulin and glucagon. Too much or too little of these hormones can cause blood sugar levels to fall too low (hypoglycemia) or rise too high (hyperglycemia). Other hormones that influence blood sugar levels are cortisol, growth hormone, and catecholamines (epinephrine and norepinephrine).
f. The pancreas, a gland in the upper abdomen, produces insulin and glucagon. The pancreas is dotted with hormone-producing tissue called the islets of Langerhans, which contain alpha and beta cells. When blood sugar rises after a meal, the beta cells release insulin. The insulin helps glucose enter body cells, lowering blood levels of glucose to the normal range. When blood sugar drops too low, the alpha cells secrete glucagon. This signals the liver to release stored glycogen and change it back to glucose, raising blood sugar levels to the normal range. Muscles also store glycogen that can be converted to glucose.
g. A person with hypoglycemia may feel weak, drowsy, confused, hungry, and dizzy. Paleness, headache, irritability, trembling, sweating, rapid heartbeat, and a cold, clammy feeling are also signs of low blood sugar. In severe cases, a person can lose consciousness and even lapse into a coma.
h. Hypoglycemia as related to diabetes
  i. The most common cause of hypoglycemia is as a complication of diabetes. Diabetes occurs when the body cannot use glucose for fuel because either the pancreas is not able to make enough insulin or the insulin that is available is not effective. As a result, glucose builds up in the blood instead of getting into body cells.
  ii. The aim of treatment in diabetes is to lower high blood sugar levels. To do this, people with diabetes may use insulin or oral drugs, depending on the type of diabetes they have or the severity of their condition. Hypoglycemia occurs most often in people who use insulin to lower their blood sugar. All people with type 1 diabetes and some people with type 2 diabetes use insulin. People with type 2 diabetes who take oral drugs called sulfonylureas are also vulnerable to low blood sugar episodes.
  iii. Conditions that can lead to hypoglycemia in people with diabetes include taking too much medication, missing or delaying a meal, eating too little food for the amount of insulin taken, exercising too strenuously, drinking too much alcohol, or any combination of these factors. People who have diabetes often refer to hypoglycemia as an "insulin reaction."
  iv. Managing Hypoglycemia in Diabetesis critical and people with diabetes should consult their health care providers for individual guidelines on target blood sugar ranges that are best for them. The lowest safe blood sugar level for an individual varies, depending on the person's age, medical condition, and ability to sense hypoglycemic symptoms. A target range that is safe for a young adult with no diabetes complications, for example, may be too low for a young child or an older person who may have other medical problems.
  v. Because they are attuned to the symptoms, people with diabetes can usually recognize when their blood sugar levels are dropping too low. They can treat the condition quickly by eating or drinking something with sugar in it such as candy, juice, or a non-diet soda. Taking glucose tablets or gels (available in drug stores) is another convenient and quick way to treat hypoglycemia.
  vi. People with type 1 diabetes are most vulnerable to severe insulin reactions, which can cause loss of consciousness. A few patients with long-standing insulin-dependent diabetes may develop a condition known as hypoglycemia unawareness, in which they have difficulty recognizing the symptoms of low blood sugar. For emergency use in patients with type 1 diabetes, physicians often prescribe an injectable form of the hormone glucagon. A glucagon injection (given by another person) quickly eases the symptoms of low blood sugar, releasing a burst of glucose into the blood.
  vii. Emergency medical help may be needed if the person does not recover in a few minutes after treatment for hypoglycemia. A person suffering a severe insulin reaction may be admitted to the hospital so that blood sugar can be stabilized.
  viii. People with diabetes can reduce or prevent episodes of hypoglycemia by monitoring their blood sugar levels frequently and learning to recognize the symptoms of low blood sugar and the situations that may trigger it. They should consult their health care providers for advice about the best way to treat low blood sugar. Friends and relatives should know about the symptoms of hypoglycemia and how to treat it in case of emergency. Hypoglycemia in people who do not have diabetes is far less common than once believed. However, it can occur in some people under certain conditions such as early pregnancy, prolonged fasting, and long periods of strenuous exercise. People on beta-blocker medications who exercise are at higher risk of hypoglycemia, and aspirin can induce hypoglycemia in some children. Drinking alcohol can cause blood sugar to drop in some sensitive individuals, and hypoglycemia has been well documented in chronic alcoholics and binge drinkers.
i. To diagnose hypoglycemia in people who do not have diabetes, the doctor looks for the following three conditions:
  i. The patient complains of symptoms of hypoglycemia
  ii. Blood glucose levels are measured while the person is experiencing those symptoms and found to be 45 mg/dL or less in a woman or 55 mg/dL or less in a man
  iii. The symptoms are promptly relieved upon ingestion of sugar.
j. For many years, the oral glucose tolerance test (OGTT) was used to diagnose hypoglycemia. Experts now realize that the OGTT can actually trigger hypoglycemic symptoms in people with no signs of the disorder. For a more accurate diagnosis, experts now recommend that blood sugar be tested at the same time a person is experiencing hypoglycemic symptoms.
k. Reactive Hypoglycemia
  i. A diagnosis of reactive hypoglycemia is considered only after other possible causes of low blood sugar have been ruled out. Reactive hypoglycemia with no known cause is a condition in which the symptoms of low blood sugar appear 2 to 5 hours after eating foods high in glucose.
  ii. Ten to 20 years ago, hypoglycemia was a popular diagnosis. However, studies now show that this condition is actually quite rare. In these studies, most patients who experienced the symptoms of hypoglycemia after eating glucose-rich foods consistently had normal levels of blood sugar—above 60 mg/dL. Some researchers have suggested that some people may be extra sensitive to the body's normal release of the hormone epinephrine after a meal.
  iii. People with symptoms of reactive hypoglycemia unrelated to other medical conditions or problems are usually advised to follow a healthy eating plan. The doctor or dietitian may suggest that such a person avoid foods high m carbohydrates; eat small, frequent meals and snacks throughout the day; exercise regularly; and eat a variety of foods, including whole grams, vegetables, and fruits.
1. Rare Causes of Hypoglycemia
  i. Fasting hypoglycemia occurs when the stomach is empty. It usually develops in the early morning when a person awakens. As with other forms of hypoglycemia, the symptoms include headache, lack of energy, and an inability to concentrate. Fasting hypoglycemia may be caused by a variety of conditions such as hereditary enzyme or hormone deficiencies, liver disease, and insulin-producing tumors.
  ii. Hereditary Glycogen Storage Disease
    (1) The treatment for all glycogen storage diseases is aimed at prevention. Treatment needs to be started as soon as the disorder is diagnosed. For GSD type la, diet is the cornerstone of treatment. The brain can only use glucose for energy. To avoid low blood sugar, it is therefore essential for the person to constantly have a source of energy that their body can use. Since it is impossible to be eating all the time, people with this type of GSD usually:
      (a) have tube feedings while they sleep, or
      (b) wake up in the night to take cornstarch, or
      (c) take cornstarch between meals
        (i) Cornstarch takes a long time for the body to break down and is therefore available as an energy source during periods of fasting.
    (2) Untreated glycogen storage disease type la can lead to:
      (a) Very low blood sugar, which can be life-threatening
      (b) enlarged liver
      (c) muscle wasting
      (d) high levels of cholesterol
      (e) blood clotting problems
      (f) susceptibility to infections
      (g) stunted growth
      (h) bone problems (osteoporosis)
      (i) liver problems
    (3) Kidney problems: People with GSD type 1a who are in good metabolic control through diet management can prevent low blood sugar. They also have fewer symptoms and long-term complications.
    iii. In hereditary fructose intolerance, a disorder usually seen in children, the body is unable to metabolize the natural sugar fructose.
      (1) Giving glucose and eliminating fructose from the diet treat attacks of hypoglycemia, marked by seizures, vomiting, and unconsciousness.
    iv. Galactosemia, a rare genetic disorder, hampers the body's ability to process the sugar galactose.
      (1) An infant with this disorder may appear normal at birth, but after a few days or weeks of drinking milk (which contains galactose), the child may begin to vomit, lose weight, and develop cataracts.
      (2) The liver may fail to release stored glycogen into the blood, triggering hypoglycemia.
    v. A deficiency of growth hormone causes increased sensitivity to insulin.
    vi. This sensitivity occurs because growth hormone opposes the action of insulin on muscle and fat cells.
      (1) For this reason, children with growth hormone deficiency sometimes suffer from hypoglycemia, which goes away after treatment.
  m. After citing the above information it is noted that, by the action of the fiber(s) and with the proper ratio, along with the features of the invention one is hopeful that many of the symptoms of hypoglycemia may be reduced and/or ameliorated.
  n. Further adding medication and the controlling of the release of the active ingredients enhance the invention.
  o. It is to be again noted that many people do not take medication at all, miss doses, and look for excuses. It is necessary to drink water everyday to live. So it then becomes a very unique and sophisticated delivery system.
45. An object of the invention is to look at a "more than one delivery" system and/or vehicle working in consort for the desired outcome/result.
  a. Covered thoroughly in this invention is the basic fact that water, in U.S. Pat. No. 6,248,390, to this inventor is the delivery system for fiber and with enrichments being delivered through viscosity changes, encapsulations, and or both there now exists more than one delivery system within the container.
    i. The delivery systems may also have by nature and or by employing scientific technologies the ability to sustain and or control the release of the significant ingredient(s).
  b. It is to be considered, by this inventiveness, that additional delivery systems be offered which will work in consort with the enhanced fiberwater, and/or realistically with any container of liquid (even soup and/or soup like) that has a designated purpose . . . even water to hydrate . . . which are not in the container.
    i. A dual compartment container may be used for this purpose whereby one part contains the fiberwater, fiberwater enhanced with additives and/or the like
      (1) Two or more compartments may exists in a companion to the liquid container
    ii. They may be in the same form as in the container (liquid or the like), or a different form (gel, dry form)
    iii. The important factor here is to be able to deliver bio-available ingredients/enhancements to the consumer whereby to be effective/results obtained, the amount(s) of the active cannot "fit" within the parameters of the drink. For an example to get the significant ingredients one might have to take more than one drink and that might not be practical and/or could even present "negatives". This may employ (1) using the digestive system (by mouth)
(2) or without having to use the digestive system, such delivery systems include but are not limited to:
 (a) Trans-dermal (patch)
 (b) Trans-mucousal (patch)
 (c) Sublingual
 (d) Topical; to be used on the skin (ratioed to density of the skin along with particle size appropriate to absorption) . . . in such form as a salve, a cream, a lotion, and/or the like
  (i) As an example, an athlete who presents out of doors, it is possible to present a sports drink with amino acids (which may relieve fatigue as an example). The amino acids may be part of the drink, or in a crème with or without sun protection (SPF rating), which will serve to provide and/or support one or more targets.
 (e) Rectal
 (f) Injectable
 (g) Subcutanesous
iv. Such additives are not designed to go into or combined with the liquid, but are presented in such fashion as to be taken with the liquid drink and/or soup.
 (1) They may present in one or more of the following forms . . . and taken, used, or both in consort with the liquid.
  (a) Pill, capsule, tablet form to be swallowed with the liquid
  (b) Gel, gu form and packaged as an example like the well known, and well received, mustard, catsup, mayonnaise packets to be taken with the liquid
  (c) Vials
  (d) Packets in any other form than #2 above . . . these may present in a candy like form, granules, liquid, lozenge, beads, and/or the like which may or may not include another delivery system such as encapsulations (regardless of size, shape, color, visible and or non-visible)
v. They may also have a relationship with the liquid, regardless of form, that is time sensitive
 (1) This is best described as a time frame exact, approximate, or both whereby you have a prescribed interval as related to ingesting, ingesting and using the companions
vi. Likely situations would include, but not be limited to, a metered portion of the companion(s) to fiber-water (as the example), that would be packaged in one of the following manners and sold
 (1) As a unit with the product/container regardless of the packaging
 (2) Sold separately in one or more units, which are targeting the same function and/or varied functions.
vii. Business models
 (1) This section of inventiveness allows companies to enhance the value of their existing products with out changing the basis product, which presents a value to the consumer and information to the marketer/producing company etc.
 (2) The public is a giant feed back machine. Basically the public does not buy, once and/or continuously, what they do not want. Or if tied with a promotion or a bonus the feed back will sort out by the obvious viii. This inventiveness serves as a vehicle to test market new production technologies, methodologies, products, and/or the like
 (1) As the just mentioned advances new opportunities become available . . . new equipment as an example. This will allow companies to put more additives inside the liquid. What to put in will be important and if the company has feed back as to what the public will select this is a valuable test-marketing tool. (It is to be noted that the inventor's CIP to her PCT as related to infusion packets/business models is used in the same way and described in further detail).
ix. This inventiveness also works with this inventors vending and distribution models in her CIP to her PCT Titled: Method of Hydration: Infusion Packet System(s), Support Member(s) Delivery System(s) and Method(s); with Business Model(s) and Method(s), whereby through vending, fast food chains, restaurants, stadiums, concert halls, food and beverage concessions, street carts, and/or the like the public directly has the ability to acquire a companion product in one or more formats to be used with the liquid.
x. It is conceived that the companion product be present in more than one chamber of the packaging, with more than one exit portals to be opened simultaneously or in consort.

Having presented extensive information thus far on the benefits of adding ingredients to fiber-water with the novelties herein invented, the inventor wishes that it be understood that we can make a difference by taking responsibility, and that additionally and hopefully, in the future health problems may be addressed more readily and effectively through safe products based on sound and reputable science.

Companies, formulations, inventors must make a tremendous responsibility for our health. Certainly one sees that the carrot, the orange, the broccoli, etc. proudly stand on their own. But we are designing, and promoting, "not occurring natural foods". However we are delivering them through naturally occurring water.

With that being said the inventor is hopeful that she may humbly and graciously provide the next generation of liquids with new and novel delivery systems and these will deliver the best possible additives, ergo playing a most significant role in designing the future, whereby the ingestion of the components of this invention and the ingredients they deliver through water . . . that one essentially needed element to live, on a daily basis will ameliorate, delay, make more livable, or altogether prevent, many health challenges. Live longer and live healthier . . .

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A nutritionally fortified liquid composition for consumption by humans and animals comprising:
   safe water;
   encapsulated additives which preserve biological activity of the encapsulated additives while eliminating taste of said additives; and
   between 0.1% and 10% by weight water-soluble indigestible fiber; and, wherein fewer than 10 calories per 100 ml are metabolized by a human when consuming the composition and wherein a human consuming the composition is unable to detect a taste difference between the safe water and the composition.

2. A nutritionally fortified liquid composition for consumption by humans and animals comprising:
   safe water;
   viscosity altering components; and
   between 0.1% and 10% by weight water-soluble indigestible fiber; and, wherein fewer than 10 calories per 100 ml are metabolized by a human when consuming the composition and whereinj a human consuming the composition in unable to detect a taste difference between the safe water and the composition.

3. A nutritionally fortified liquid composition comprising:
   water;
   a soluble fiber; and
   encapsulated plurality of different health enhancing ingredients, wherein an encapsulation (i) contains the plurality of different health enhancing ingredients, and (ii) preserve the biological activity of the encapsulated health enhancing ingredients.

4. The composition of claim 1, wherein the water soluble indigestible fiber is selected from the group consisting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

5. The composition of claim 1, wherein the encapsulated additives are selected from the group consisting of encapsulated amino acids, encapsulated vitamins, encapsulated minerals, encapsulated soluble indigestible fiber, encapsulated probiotics, encapsulated prebiotics, encapsulated antibacterials, encapsulated antioxidants and encapsulated nutraceuticals, encapsulated pain relievers, encapsulated enzymes, encapsulated anti-inflammatory agents, encapsulated hormones, encapsulated mood enhancers and encapsulated fatigue reducers.

6. The composition of claim 1, further including viscosity altering components.

7. The composition of claim 6, wherein the viscosity altering components comprise water soluble indigestible fiber.

8. The composition of claim 6, wherein the viscosity altering components comprise encapsulated additives.

9. The composition of claim 2, wherein the viscosity altering components comprise encapsulated additives.

10. The composition of claim 2, wherein the water soluble indigestible fiber is selected from the group consisting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

11. The composition of claim 2, wherein the viscosity altering components comprise encapsulated additives.

12. The composition of claim 11, wherein the encapsulated additives are selected from the group consisting of encapsulated amino acids, encapsulated vitamins, encapsulated minerals, encapsulated soluble indigestible fiber, encapsulated probiotics, encapsulated prebiotics, encapsulated antibacterials, encapsulated antioxidants and encapsulated nutraceuticals, encapsulated pain relievers, encapsulated enzymes, encapsulated anti-inflammatory agents, encapsulated hormones, encapsulated mood enhancers and encapsulated fatigue reducers.

13. The composition of claim 3, wherein the composition is a solution.

14. The composition of claim 3, wherein the composition is a suspension.

15. The composition of claim 3, wherein the composition is an emulsion.

16. The composition of claim 3, wherein the composition is carbonated.

17. The composition of claim 3, wherein the composition is sweetened.

18. The composition of claim 3, wherein the composition is in a concentrated form.

19. The composition of claim 3, wherein the plurality of encapsulated ingredients have uniform size.

20. The composition of claim 3, wherein the plurality of encapsulated ingredients have varying sizes.

21. The composition of claim 3, wherein the plurality of encapsulated ingredients have uniform shape.

22. The composition of claim 3, wherein the plurality of encapsulated ingredients have varying shapes.

23. The composition of claim 3, wherein the different health enhancing ingredients are at least one of vitamins, minerals, amino-acids, anti-oxidants, enzymes, hormones, botanicals, herbals, dietary supplements, nutraceuticals, pharmaceuticals, diagnostics, anti-virals, anti-bacterials, pro-biotics, pre-biotics, soluble fibers, and energy sources.

24. The composition of claim 3, wherein the encapsulated plurality of different health enhancing ingredients includes at least one of aromas, flavors, and colors.

25. The composition of claim 3, wherein the different health enhancing ingredients is a health enhancing ingredient in different forms.

26. The composition of claim 25, wherein one of the different forms is liquid, gel, glitter, granule, crystals, beads, powder, or micro-encapsulations.

27. The composition of claim 25, wherein the different forms are selected from the group consisting of liquid, gel, glitter, granule, crystals, beads, powder, and micro-encapsulations.

28. The composition of claim 3, wherein the different health enhancing ingredients are at least one of liquid, gel, glitter, granule, crystals, beads, powder, and micro-encapsulations.

29. The composition of claim 3, wherein the encapsulation is configured to deliver selectable amounts of the different health enhancing ingredients for a particular human or animal.

30. The composition of claim 3, wherein the encapsulation delivers therapeutically effective amounts of the different health enhancing ingredients.

31. The composition of claim 3, wherein the encapsulation regulates the delivery of the different health enhancing ingredients.

32. The composition of claim 3, wherein the encapsulation is visible.

33. The composition of claim 3, wherein a color of the encapsulation relates to the dose of the different health enhancing ingredients.

34. The composition of claim 3, wherein the encapsulation is non-visible.

35. The composition of claim 3, wherein the encapsulation is chewable.

36. The composition of claim 3, wherein the encapsulation is designed to be swallowed as a whole.

37. The composition of claim 3, further including
a second water soluble indigestible fiber.

38. The composition of claim 3, wherein the soluble fiber is selected from the group consisting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

39. A nutritionally fortified liquid composition comprising:
water;
a soluble fiber; and
encapsulated plurality of different fortified particles, wherein an encapsulation (i) contains the plurality of different fortified particles, and (ii) preserves the biological activity of the encapsulated fortified particles.

40. The composition of claim 39, wherein the composition is a solution.

41. The composition of claim 39, wherein the composition is a suspension.

42. The composition of claim 39, wherein the composition is an emulsion.

43. The composition of claim 39, wherein the composition is carbonated.

44. The composition of claim 39, wherein the composition is sweetened.

45. The composition of claim 39, wherein the composition is in a concentrated form.

46. The composition of claim 39, further including
a plurality of encapsulated ingredients.

47. The composition of claim 46, wherein the plurality of encapsulated ingredients have uniform size.

48. The composition of claim 46, wherein the plurality of encapsulated ingredients have varying sizes.

49. The composition of claim 46, wherein the plurality of encapsulated ingredients have uniform shape.

50. The composition of claim 46, wherein the plurality of encapsulated ingredients have varying shapes.

51. The composition of claim 39, wherein the fortification of the plurality of different fortified particles includes at least one of vitamins, minerals, amino-acids, anti-oxidants, enzymes, hormones, botanicals, herbals, dietary supplements, nutraceuticals, pharmaceuticals, diagnostics, anti-virals, anti-bacterials, pro-biotics, pre-biotics, soluble fibers, and energy sources.

52. The composition of claim 39, wherein the encapsulated plurality of different fortified particles includes at least one of aromas, flavors, and colors.

53. The composition of claim 39, wherein the different fortified particles are fortified particles of different forms.

54. The composition of claim 39, wherein the different fortified particles have a form of at least one of glitter, granule, crystals, beads, powder, and micro-encapsulations.

55. The composition of claim 39, wherein the encapsulation is configured to deliver selectable amounts of the fortification of the different fortified particles for a particular human or animal.

56. The composition of claim 39, wherein the encapsulation delivers therapeutically effective amounts of the fortification of the different fortified particles.

57. The composition of claim 39, wherein the encapsulation regulates the delivery of the fortification of the different fortified particles.

58. The composition of claim 39, wherein the encapsulation is visible.

59. The composition of claim 39, wherein a color of the encapsulation relates to the dose of the fortification of the different fortified particles.

60. The composition of claim 39, wherein the encapsulation is non-visible.

61. The composition of claim 39, wherein the encapsulation is chewable.

62. The composition of claim 39, wherein the encapsulation is designed to be swallowed as a whole.

63. The composition of claim 39, further including
a second water soluble indigestible fiber.

64. The composition of claim 39, wherein the soluble fiber is selected from the group consisting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

65. The composition of claim 3, wherein the encapsulation is a micro-encapsulation.

66. A nutritionally fortified liquid composition comprising:
water;
a soluble fiber;
an encapsulation; and
micro-encapsulated plurality of health enhancing ingredients,
wherein the encapsulation (i) contains the micro-encapsulated plurality of health enhancing ingredients, and (ii) preserves the biological activity of the micro-encapsulated plurality of health enhancing ingredients.

67. The composition of claim 66, wherein the composition is a solution.

68. The composition of claim 66, wherein the composition is a suspension.

69. The composition of claim 66, wherein the composition is an emulsion.

70. The composition of claim 66, wherein the composition is carbonated.

71. The composition of claim 66, wherein the composition is sweetened.

72. The composition of claim 66, wherein the composition is in a concentrated form.

73. The composition of claim 66, wherein the micro-encapsulations are of uniform size.

74. The composition of claim 66, wherein the micro-encapsulations are of varying sizes.

75. The composition of claim 66, wherein the micro-encapsulations are of uniform shape.

76. The composition of claim 66, wherein the micro-encapsulations are of varying shapes.

77. The composition of claim 66, wherein the plurality of health enhancing ingredients are at least one of vitamins, minerals, amino-adds, anti-oxidants, enzymes, hormones, botanicals, herbals, dietary supplements, nutraceuticals, pharmaceuticals, diagnostics, anti-virals, anti-bacterials, pro-biotics, pre-biotics, soluble fibers, and energy sources.

78. The composition of claim 66, wherein the micro-encapsulated plurality of health enhancing ingredients includes at least one of aromas, flavors, and colors.

79. The composition of claim 66, wherein the plurality of health enhancing ingredients are of different forms.

80. The composition of claim 79, wherein one of the different forms is liquid, gel, glitter, granule, crystals, beads, powder, or micro-encapsulations.

81. The composition of claim 79, wherein the different forms are selected from the group consisting of liquid, gel, glitter, granule, crystals, beads, powder, and micro-encapsulations.

82. The composition of claim 66, wherein the micro-encapsulations are configured to deliver selectable amounts of the plurality of health enhancing ingredients for a particular human or animal.

83. The composition of claim 66, wherein the micro-encapsulations deliver therapeutically effective amounts of the plurality of health enhancing ingredients.

84. The composition of claim 66, wherein the micro-encapsulations regulate the delivery of the plurality of health ingredients.

85. The composition of claim 66, wherein at least one of (i) the encapsulation and (ii) the micro-encapsulation is visible.

86. The composition of claim 66, wherein a color of the micro-encapsulations relates to the dose of the health enhancing ingredients.

87. The composition of claim 66, wherein at least one of (i) the encapsulation and (ii) the micro-encapsulations is non-visible.

88. The composition of claim 66, further including a second water soluble indigestible fiber.

89. The composition of claim 66, wherein the soluble fiber is selected from the group consisting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

90. A nutritionally fortified liquid composition comprising:

water;

a soluble fiber;

encapsulated health enhancing ingredient; and a fortified particle, wherein the encapsulated health enhancing ingredient is attached to the fortified particle.

91. The composition of claim 90, wherein the fortified particle is attached to the exterior of the encapsulated health enhancing ingredient.

92. The composition of claim 91, wherein the composition is a solution.

93. The composition of claim 91, wherein the composition is a suspension.

94. The composition of claim 91, wherein the composition is an emulsion.

95. The composition of claim 91, wherein the composition is carbonated.

96. The composition of claim 91, wherein the composition is sweetened.

97. The composition of claim 91, wherein the composition is in a concentrated form.

98. The composition of claim 91, further including a plurality of encapsulated ingredients, and a plurality of fortified particles.

99. The composition of claim 91, wherein at least one of (i) the fortification of the fortified particle and (ii) the health enhancing ingredient is at least one of vitamins, minerals, amino-acids, anti-oxidants, enzymes, hormones, botanicals, herbals, dietary supplements, nutraceuticals, pharmaceuticals, diagnostics, anti-virals, anti-bacterials, pro-biotics, pre-biotics, soluble fibers, and energy sources.

100. The composition of claim 91, wherein at least one of (i) the fortified particle and (ii) the encapsulated health enhancing ingredient includes at least one of aromas, flavors, and colors.

101. The composition of claim 91, wherein at least one of (i) the fortified particle and (ii) the health enhancing ingredient is in different forms.

102. The composition of claim 91, wherein the health enhancing ingredient is at least one of liquid, gel, glitter, granule, crystals, beads, powder, and micro-encapsulations.

103. The composition of claim 91, wherein the fortified particle is at least one of glitter, granule, crystals, beads, powder, and micro-encapsulations.

104. The composition of claim 91, further including a second water soluble indigestible fiber.

105. The composition of claim 91, wherein the soluble fiber is selected from the group consisting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

106. A nutritionally fortified liquid composition comprising:

water; and a soluble fiber, wherein the water has a plurality of viscosity altering components including a plurality of encapsulated health enhancing ingredients and/or fortified particles, and wherein the viscosity altering components provide a layered composition of encapsulated ingredients and/or fortified particles.

107. The composition of claim 106, wherein the viscosity altering components are at least one of soluble fibers, gums, gelatins, food starches, botanicals, thickeners, encapsulations, particles and food oils.

108. The composition of claim 106, wherein the viscosity layers of the composition blend into each other.

109. The composition of claim 106, wherein the viscosity layers of the composition do not blend into each other.

110. The composition of claim 106, wherein the health enhancing ingredients are at least one of vitamins, minerals, amino-acids, anti-oxidants, enzymes, hormones, botanicals, herbals, dietary supplements, nutraceuticals, pharmaceuticals, diagnostics, anti-virals, anti-bacterials, pro-biotics, pre-biotics, soluble fibers, and energy sources.

111. The composition of claim 106, wherein the viscosity altering components include aromas, flavors, and colors.

\* \* \* \* \*

UNITED STATES PATENT AND TRADEMARK OFFICE
CERTIFICATE OF CORRECTION

PATENT NO. : 7,115,297 B2
APPLICATION NO. : 10/244699
DATED : October 3, 2006
INVENTOR(S) : Suzanne Jaffe Stillman It is certified that error appears in the above-identified patent and that said Letters Patent is hereby corrected as shown below:

Title page item [63] delete under "Related U.S. Application Data" and insert the following:

--The present application is a continuation-in-part application of, and claims priority from PCT/US01/09171 designating the United States and filed on March 21, 2001 which claimed priority from U.S. application Ser. No. 60/192,242, and a continuation-in-part application of U.S. Ser. No. 10/204,572, filed April 2, 2003 which was a continuation of, and claims priority from, PCT/US01/05630 filed Feb. 22, 2001, which was a continuation of and claims priority from U.S. Ser. No. 09/510,400, filed Feb. 22, 2000 and issued Jun. 19, 2001 as U.S. Pat. No. 6,248,390.--

Signed and Sealed this

Twenty-fourth Day of April, 2007

JON W. DUDAS
*Director of the United States Patent and Trademark Office*

US007115297C1

(12) EX PARTE REEXAMINATION CERTIFICATE (7781st)

United States Patent
Stillman

(10) Number: US 7,115,297 C1
(45) Certificate Issued: Sep. 28, 2010

(54) NUTRITIONALLY FORTIFIED LIQUID COMPOSITION WITH ADDED VALUE DELIVERY SYSTEMS/ELEMENTS/ADDITIVES

(76) Inventor: Suzanne Jaffe Stillman, 1712 S. Barington Ave., Los Angeles, CA (US) 90025

Reexamination Request:
No. 90/009,255, Aug. 15, 2008

Reexamination Certificate for:
| Patent No.: | 7,115,297 |
| Issued: | Oct. 3, 2006 |
| Appl. No.: | 10/244,699 |
| Filed: | Sep. 16, 2002 |

Certificate of Correction issued Apr. 24, 2007.

Related U.S. Application Data

(63) Continuation-in-part of application No. 10/204,572, filed on Apr. 2, 2003, now Pat. No. 7,238,380, and a continuation-in-part of application No. PCT/US01/09171, filed on Mar. 21, 2001, said application No. 10/204,572, is a continuation of application No. PCT/US01/05630, filed on Feb. 22, 2001, which is a continuation of application No. 09/510,400, filed on Feb. 22, 2000, now Pat. No. 6,248,390.

(60) Provisional application No. 60/192,242, filed on Mar. 21, 2000.

(51) Int. Cl.
*A23L 2/00* (2006.01)

(52) U.S. Cl. .................... 426/590; 426/594; 426/72; 426/73; 426/74

(58) Field of Classification Search ................. None
See application file for complete search history.

(56) References Cited

U.S. PATENT DOCUMENTS

| 2,224,252 A | 10/1940 | Callaway |
| 3,009,859 A | 11/1961 | Laborit et al. |
| 3,111,641 A | 11/1963 | Sperti et al. |
| 3,227,562 A | 1/1966 | Houghtaling et al. |
| 3,337,404 A | 8/1967 | Polli et al. |
| 3,564,740 A | 2/1971 | Calfee |
| 3,908,024 A | 9/1975 | Wankier |
| 3,939,283 A | 2/1976 | Billington |
| 4,034,493 A | 7/1977 | Bail |
| 4,042,684 A | 8/1977 | Kahm |
| 4,154,814 A | 5/1979 | Hand et al. |
| 4,167,587 A | 9/1979 | Danforth |
| 4,187,194 A | 2/1980 | Wellman et al. |
| 4,211,668 A | 7/1980 | Tate |
| 4,217,370 A | 8/1980 | Rawlings et al. |
| 4,283,432 A | 8/1981 | Mitchell et al. |
| 4,309,417 A | 1/1982 | Staples |
| 4,315,513 A | 2/1982 | Nawash et al. |
| 4,393,873 A | 7/1983 | Nawash et al. |
| 4,444,761 A | 4/1984 | Spiller |
| 4,447,532 A | 5/1984 | Coker et al. |
| 4,448,770 A | 5/1984 | Epting, Jr. |
| 4,497,793 A | 2/1985 | Simkin |
| 4,689,235 A | 8/1987 | Barnes et al. |
| 4,711,784 A | 12/1987 | Yang |
| 4,738,856 A | 4/1988 | Clark |
| 4,749,575 A | 6/1988 | Rotman |

(Continued)

FOREIGN PATENT DOCUMENTS

| FR | 2586532 | 3/1967 |
| JP | 59051741 A | 3/1984 |
| JP | 10-09520 | 1/1989 |
| JP | H02-154673 | 6/1990 |
| JP | 02-154673 | 6/1990 |
| JP | 4-311378 A | 11/1992 |
| JP | H5-17503 | 1/1993 |
| JP | 05-017503 | 1/1993 |
| JP | H06-90703 | 4/1994 |
| JP | 06-090703 | 4/1994 |
| JP | 6-100442 | 4/1994 |
| JP | 8-275752 | 10/1996 |
| JP | 9-020660 | 1/1997 |
| JP | 09-059138 A | 3/1997 |
| JP | 09-245492 | 3/1999 |
| JP | 11-512604 A | 11/1999 |
| JP | 2000-232855 | 8/2000 |
| JP | 2001-509007 A | 7/2001 |
| WO | WO 97/11614 A1 | 4/1997 |
| WO | WO 98/19564 A1 | 5/1998 |
| WO | WO 01/62108 | 8/2001 |

OTHER PUBLICATIONS

"Total Dissolved Solids in Drinking0Water", Guidelines for Drinking–Water Quality, 2nd Edition, vol. 2, Health Criteria and Other Supporting Information, World Health Organization, Geneva, 1996.
Chemical Database: Picloram, EnvironmentalChemistry.com, http://www.environmentalchemistry.com, Nov. 17, 2009, 1–3.
Delta Communications Group, http://www.delta–comm.com, Nov. 17, 2009, 1 page.

(Continued)

*Primary Examiner*—Brenda Brumback

(57) ABSTRACT

A shelf-stable, ready to use, water-like composition for humans/animals; as an adjunct to fiber-water, and/or safe drinking water, consumed directly, tube feedings, or in the preparation/reconstitution of food(s)/beverage(s). Fortified Fiber-Water is fiber-water, with added delivery systems: Encapsulations/particles, of different size(s), shape(s), material(s), colors, non-visible, serving one or more functions: improved taste, odor-masking: controlled release applications; bio-availability of actives, avoid hygroscopicity; minimized interactions, improved thermal, oxidative, and shelf-life: decorative. Viscosity changing elements, (with one or more viscosity changing additives, with or without encapsulations, particles) to enhance delivery of active medicants/ingredients of categories: pharmaceuticals, nutraceuticals, dietary supplements, therapeutics, diagnostics, etc. Composition ensures hydration, simultaneously providing soluble fiber (fiber-water), with additives contained within the delivery systems, having the ability to target specific health goals/needs: weight loss, diabetes, cholesterol/heart, gastrointestinal tract disorders/improvement, osteoporosis, cancer, pain, stress, relaxant, stimulant etc.

U.S. PATENT DOCUMENTS

| | | | |
|---|---|---|---|
| 4,777,042 A | 10/1988 | Toda et al. | |
| 4,778,677 A | 10/1988 | Ebbesen | |
| 4,784,861 A | 11/1988 | Gori | |
| 4,834,990 A | 5/1989 | Amer | |
| 4,849,222 A | 7/1989 | Broaddus | |
| 4,911,889 A | 3/1990 | Leland et al. | |
| 4,953,572 A | 9/1990 | Rose et al. | |
| 4,988,530 A | 1/1991 | Hoersten et al. | |
| 4,996,063 A | 2/1991 | Inglett | |
| 5,002,934 A | 3/1991 | Norton et al. | |
| 5,009,819 A | 4/1991 | Popescu et al. | |
| 5,019,400 A | 5/1991 | Gombotz et al. | |
| 5,019,594 A | 5/1991 | Wurtman et al. | |
| 5,024,842 A | 6/1991 | Edgren et al. | |
| 5,032,411 A | 7/1991 | Stray-Gundersen | |
| 5,051,261 A | 9/1991 | McGinity et al. | |
| 5,055,460 A | 10/1991 | Friedlander | |
| 5,077,057 A | 12/1991 | Szoka, Jr. | |
| 5,082,673 A | 1/1992 | Inglett | |
| 5,108,774 A | 4/1992 | Mills et al. | |
| 5,126,332 A | 6/1992 | Ohta et al. | |
| 5,149,541 A | 9/1992 | Leis, Jr. et al. | |
| 5,162,128 A | 11/1992 | Mills et al. | |
| 5,178,896 A | 1/1993 | Langner | |
| 5,209,978 A | 5/1993 | Kosaka et al. | |
| 5,215,750 A | 6/1993 | Keane, II | |
| 5,219,570 A | 6/1993 | Barbera | |
| 5,223,268 A | 6/1993 | Stetski et al. | |
| 5,225,219 A | 7/1993 | Inglett | |
| 5,229,117 A | 7/1993 | Leland et al. | |
| 5,229,172 A | 7/1993 | Cahalan et al. | |
| 5,260,279 A | 11/1993 | Greenberg | |
| 5,260,873 A | 11/1993 | Hishinuma | |
| 5,270,297 A | 12/1993 | Paul et al. | |
| 5,273,754 A | 12/1993 | Mann | |
| 5,294,458 A | 3/1994 | Fujimori | |
| 5,294,606 A | 3/1994 | Hastings | |
| 5,300,310 A | 4/1994 | Elsen | |
| 5,344,824 A | 9/1994 | Ohkuma et al. | |
| 5,358,729 A | 10/1994 | Ohkuma et al. | |
| 5,364,652 A | 11/1994 | Ohkuma et al. | |
| 5,374,444 A | 12/1994 | Langner | |
| 5,378,474 A | 1/1995 | Morella et al. | |
| 5,380,717 A | 1/1995 | Ohkuma et al. | |
| 5,397,786 A | 3/1995 | Simone | |
| 5,405,836 A | 4/1995 | Richar et al. | |
| 5,422,352 A | 6/1995 | Astrup | |
| 5,430,141 A | 7/1995 | Ohkuma et al. | |
| 5,447,730 A | 9/1995 | Greenleaf | |
| 5,456,985 A | 10/1995 | Zgoulli et al. | |
| 5,458,893 A | 10/1995 | Smith | |
| 5,472,732 A | 12/1995 | Ohkuma et al. | |
| 5,505,981 A | 4/1996 | Wakabayashi et al. | |
| 5,516,535 A | 5/1996 | Heckert et al. | |
| 5,519,011 A | 5/1996 | Wakabayashi et al. | |
| 5,531,734 A | 7/1996 | Geckle et al. | |
| 5,533,973 A | 7/1996 | Piontek et al. | |
| 5,543,405 A | 8/1996 | Keown et al. | |
| 5,550,113 A | 8/1996 | Mann | |
| 5,558,897 A | 9/1996 | Goldman | |
| 5,567,424 A | 10/1996 | Hastings | |
| 5,571,441 A | 11/1996 | Andon et al. | |
| 5,587,197 A | 12/1996 | Maeda et al. | |
| 5,597,604 A | 1/1997 | Chalupa et al. | |
| 5,605,697 A | 2/1997 | Asano et al. | |
| 5,612,026 A | 3/1997 | Diehl | |
| 5,620,873 A | 4/1997 | Ohkuma et al. | |
| 5,653,996 A | 8/1997 | Hsu | |
| 5,672,301 A | 9/1997 | Orly et al. | |
| 5,681,606 A | 10/1997 | Hutchison et al. | |
| 5,698,437 A | 12/1997 | Matsuda et al. | |
| 5,700,484 A | 12/1997 | Chauffard et al. | |
| 5,721,345 A | 2/1998 | Roberfroid et al. | |
| 5,753,295 A | 5/1998 | Goldman | |
| 5,755,688 A | 5/1998 | Plontek et al. | |
| 5,776,524 A | 7/1998 | Reinhart | |
| 5,780,060 A | 7/1998 | Levy et al. | |
| 5,789,393 A | 8/1998 | Dressman et al. | |
| 5,792,754 A | 8/1998 | Green et al. | |
| 5,810,018 A | 9/1998 | Monte | |
| 5,824,353 A | 10/1998 | Tsunoda et al. | |
| 5,851,578 A | 12/1998 | Gandhi | |
| 5,880,109 A | 3/1999 | Nakamura et al. | |
| 5,891,465 A | 4/1999 | Keller et al. | |
| 5,900,251 A | 5/1999 | Raissen | |
| 5,904,851 A | 5/1999 | Taylor et al. | |
| 5,922,346 A | 7/1999 | Hersh | |
| 5,922,350 A | 7/1999 | Janoff et al. | |
| 5,935,826 A | 8/1999 | Blue et al. | |
| 5,958,456 A | 9/1999 | Baichwal et al. | |
| 5,958,497 A | 9/1999 | Grimm et al. | |
| 5,962,015 A | 10/1999 | Delrieu et al. | |
| 5,968,365 A | 10/1999 | Laurenzo et al. | |
| 5,968,569 A | 10/1999 | Cavadini et al. | |
| 5,972,415 A | 10/1999 | Brassart et al. | |
| 5,976,603 A | 11/1999 | Kota et al. | |
| 5,977,175 A | 11/1999 | Lin | |
| 5,985,282 A | 11/1999 | Haveson | |
| 5,989,574 A | 11/1999 | Slavin | |
| 5,993,880 A | 11/1999 | Frost et al. | |
| 5,997,917 A | 12/1999 | Uchida et al. | |
| 6,001,554 A | 12/1999 | Boyle et al. | |
| 6,004,610 A | 12/1999 | Wang et al. | |
| 6,007,838 A | 12/1999 | Alving et al. | |
| 6,007,872 A | 12/1999 | Lindhe et al. | |
| 6,013,622 A | 1/2000 | Bruno et al. | |
| 6,017,550 A | 1/2000 | Berk et al. | |
| 6,020,002 A | 2/2000 | Myers et al. | |
| 6,020,016 A | 2/2000 | Castleberry | |
| 6,022,500 A | 2/2000 | John et al. | |
| 6,022,525 A | 2/2000 | Sutton et al. | |
| 6,030,605 A | 2/2000 | D'Ameila et al. | |
| 6,033,713 A | 3/2000 | Sheldon | |
| 6,033,888 A | 3/2000 | Batich et al. | |
| 6,039,952 A | 3/2000 | Sunvold et al. | |
| 6,042,854 A | 3/2000 | Morris et al. | |
| 6,077,504 A | 6/2000 | Vesley et al. | |
| 6,102,224 A | 8/2000 | Sun et al. | |
| 6,120,803 A | 9/2000 | Wong et al. | |
| 6,133,323 A | 10/2000 | Hayek | |
| 6,180,099 B1 | 1/2001 | Paul | |
| 6,180,131 B1 | 1/2001 | Sunvold et al. | |
| 6,190,591 B1 | 2/2001 | Van Lengerich | |
| 6,193,999 B1 | 2/2001 | Gennadios | |
| 6,204,291 B1 | 3/2001 | Sunvold et al. | |
| 6,235,320 B1 | 5/2001 | Daravingas et al. | |
| 6,248,390 B1 | 6/2001 | Stillman | |
| 6,261,589 B1 | 7/2001 | Pearson et al. | |
| 6,265,450 B1 | 7/2001 | Asami et al. | |
| 6,296,892 B1 | 10/2001 | Elseviers et al. | |
| 6,313,558 B1 | 11/2001 | Abukawa et al. | |
| 6,328,967 B1 | 12/2001 | Rivera | |
| 6,355,274 B1 | 3/2002 | Dartey et al. | |
| 6,365,209 B2 | 4/2002 | Cherukuri | |
| 6,368,629 B1 | 4/2002 | Watanabe et al. | |
| 6,368,633 B1 | 4/2002 | Lou et al. | |
| 6,383,534 B1 | 5/2002 | Dyrr et al. | |
| 6,399,090 B1 | 6/2002 | Shehadeh | |
| 6,399,124 B1 | 6/2002 | Lesens et al. | |
| 6,403,657 B1 | 6/2002 | Hinz | |
| 6,406,730 B1 | 6/2002 | Banyard et al. | |

| | | |
|---|---|---|
| 6,410,061 B1 | 6/2002 | Morre et al. |
| 6,410,521 B1 | 6/2002 | Mundy et al. |
| 6,410,522 B1 | 6/2002 | Ruenberg |
| 6,410,685 B1 | 6/2002 | Masuyama et al. |
| 6,416,800 B1 | 7/2002 | Weber et al. |
| 6,416,806 B1 | 7/2002 | Zhou |
| 6,420,350 B1 | 7/2002 | Fleischner |
| 6,436,453 B1 | 8/2002 | Van Lengerich et al. |
| 6,468,568 B1 | 10/2002 | Leusner et al. |
| 6,500,463 B1 | 12/2002 | Van Lengerich |
| 6,531,156 B1 | 3/2003 | Clark et al. |
| 6,544,568 B2 | 4/2003 | La Droitte et al. |
| 6,558,718 B1 | 5/2003 | Evenson et al. |
| 6,620,445 B1 | 9/2003 | Knueven |
| 6,723,358 B1 | 4/2004 | Van Lengerich |
| 6,758,715 B2 | 7/2004 | Banks |
| 6,953,593 B2 | 10/2005 | Kuhrts |
| 7,238,380 B2 | 7/2007 | Stillman |
| 2002/0132780 A1 | 9/2002 | Heisey et al. |
| 2005/0211768 A1 | 9/2005 | Stillman |
| 2007/0009576 A1 | 1/2007 | Stillman |
| 2007/0160735 A1 | 7/2007 | Stillman |
| 2008/0014327 A1 | 1/2008 | Stillman |

OTHER PUBLICATIONS

Information Access Company, http://www.fundinguniverse.com, Company History, Nov. 17, 2009, 1–4.

Morrison & Boyd, "Acidity of Phenols", Organic Chemistry, 3rd Edition, Allyn and Bacon, Inc., Boston, 1973, 797–799.

BetaCote™ Technical Information, Lycored Natural Products Industries, accessed via the internet on Sep. 18, 2009 att URL <http://www.lycored.com/web/content/betacote–tech.asp.

A. Golay, et al., "The effect of a liquid supplement containing guar gum and fructose on glucose tolerance in non–insulin–dependent diabetic patients", Nutr Metab Cardiovasc Dis (1995) 5:141–148.

"Hypochelesterolemic Effect of Sodium Proprionate", J. Nutri. Sci. Vitaminol., vol. 41, No. 1, 1995, pp. 77–78, Kishimoto et al.

Cordoba, et al., "Chondroitin Sulfate and Other Sulfate Containing Chondroprotective Agents . . . ", Ostheoarthritis and Cartilage, 2003 v. 11 p. 228.

Markovich, "Physiological Roles and Regulation of Mammalian Sulfate Transporters", Physiological Reviews, 2001 v. 81 No. p. 1499.

Hoffer, et al., "Sulfate Could Mediate The Therapeutic Effect of Glucosamine Sulfate", Metabolism, 2001, v. 50 p. 767.

Hannan, "Effect of Dietary Protein on Bone Loss in Elderly Men and Women", J. of Bone and Mineral Research, 2000 v. 15 p. 2504.

ProductScan Online, Worldwide beverage Industry in which products are marketed as containing Fiber or as being a good source of Fiber, 137 Full Reports, Mar. 1, 2003.

ProductScan Online, Asian Beverage Industry in which products are marketed as fruit and Fruit flavored drinks, 154 Full Reports, Dec. 30, 2002.

ProductScan Online, German Beverage Industry in which products are marketed as fruit and Fruit flavored drinks, 127 Full Reports, May 13, 2002.

Takashi Ide, et al., "Hypolipidemic Effects of Guar Gum and It's Enzyme Hydrolysale in Rats Fed Highly Saturated Fat Diets", Ann Nutr. Metab, 1991; 35:34–44 (abstract).

M. Kamen, et al., "Reduction in Diarrhea Incidence by Soluble Fiber in Patients Receiving Total or Supplemental Enteral Nutrition," Dept. of Surgery, Ruhr University, Bochum Gammany, Jun. 20, 1994; JPEN, 18:486–90, 1994 (abstract).

Gary A. Weaver, et al., "Dietary Guar Gum Alters Colonic Microbial Fermentation In Azoxymetana–Treated Rats", J of Nutrition 126(8): 1979–1991 (abstract).

Hidehisa Takahashi, et al., "Effect of Partially Hydrolyzed Guar Gum on Fecal Output in Human Volunteers,"Nutrition Research, vol. 13, pp. 649–657, 1993 (abstract).

Hidehisa Takahashi, et al., "Effect of Liquid Diets with or without partially hydrolyzed Guar. Gum on Intestinal Microbial Flora and Function of Rats", Nutrition Reseach, vol. 15, No. 4, pp. 527–536, 1995 (abstract).

Hidehisa Takahashi, et al., "Influence of Intact and Partially Hydrolysed Guar Gum on Iron Utilization in Rats Fed On Iron–Deficient Diets", Comp. Biochem. Physical. vol. 109 A, No. 1, pp. 75–82 (1994).

Hidehisa Takahashi, et al., "Influence of Partially Hydrolyzed Guar Gum on Constipation in Women", Vitamental., vol. 40, p. 251–259 (1994).

Electronic code of Federal Regulation, Title 21: Food and Drugs, Part 165, 110, Bottled Water, Jul. 6, 2009.

Hiroshi Hara, et al., Increases in Calcium Absorption With Ingestion of Soluble Dietary Fibre, Guar–Gum Hydrolysate, Depend on the Casecum in Partially Nephrectomized and Normal Rats, British Journal of Nutrition (1996) pp. 773.

Kazuhiro Ohkuma, et al., "Pyrolysis of Starch and Its Digestibility by Enzymes—Characterization of Indigestibility Dextrin—", Matsutani Chemical Research Laboratories Denpun Kagaku, 1990 (37) 107–114.

Brochure by Matsutani Chemical Industry, "Fibersol–2–Physiological Attributes", Feb. 16, 1999.

Brochure by Matsutani America, Inc., Matsutani's Produce & Their Functionalities, May 1999.

Brochures by Imperial Sensus LLC, Facts About Insulin/FOS, "Fruitafit Nutritional Information", What is Fruitafit?, 1999.

Novartis Nutrition Corporation, "Benefiber Nutritional Data", Mar. 1999.

Novartis Nutrition Corporation, "Novartis Products", Jan. 31, 2000.

Pamphlet by Imperial Sensus, LLC, "Inulin, A Natural Non–Digestible Carbohydrate Having Healthy Influences For Preventing Disease—Occurrence, History, Preparation, Safety, Physiology and Related Health Implications", Version 23–10.29.99, 1997, 1998, 1999.

Elsworth R. Buskirk, et al., "Body Fluid Balance" CRC Press, 1966, pp. 1–17.

Flavor Encapsulation: A Convergence of Science and Art, Food and Technology, Jul. 2004, vol. 58, No. 7, Porzio M.

Novel Encapsulation System Provides Controlled Release of Ingredients, Nov. 2003, vol. 57, No. 11, Shefer, et al.

Goldschlager Article from http://www.cockeyed.com/inside/goldschlager/goldschlager.html.

Orbitz Article from http://www.bevnet.com/reviews/orbitz, 2004.

Joanne Slavin, "Commercially Available Enteral Formula With Fiber and Bowel Function Measures", Nutrition in Clinical Practice, vol. 5 pp. 247–250, Dec. 1990.

Y. Ueda, eta l., "Effects of Ingestible Dextrin on Blood Glucose and Insulin Levels After Various Sugar Loads in Rats", Japan Nutritional Food Science, 1993, p. 46.

John E. Greenleaf "Problem: Thirst, Drinking Behavior and Involuntary Dehydration" Medicine and Science in Sports and Exercise, pp. 645–656.

Kazuhiro Ohkuma, et al., Pyrolysis of Starch and Its Digestibility by Enzymes–Characterization of Indigestibility Dextrin–Matsutani Chemical Research Laboratories, Denpun Kagaku, 1990 (37) 107–114 (abstract) Figs.1–7, Tables 1–5.

A.J. Vince, et al., The effect of lactulose, pectin, arabinogalactan and cellulose . . . , British Journal of Nutrition, 1990, vol. 63, pp. 17–26, London.

R. Robinson, et al., Effects of Dietary Arabinogalactan on Gastrointestinal and Blood . . . , Journal of the American College of Nutrition, 2001, vol. 20, 279–285.

http://diabets.webmd.com/is–there–a–diabetes–cure (accessed Jan. 21, 2009).

Deis, R., "Dietary Fiber: A Healthy Discussion," Food Product Design. Jan. 1999.

Y. Ueda, et al., "Effects of Indigestible Dextrin on Blood Glucose and Urine C–peptide Levels Following Sucrose Loading", J. Japan Diab. Soc., 1993 (36), 715–723.

M. Nummura, et al., "Effect of Dietary Fibers on the Deffusion of Glucose and Metal Ions through Cellulose Membrane", J. Japan Soc. Clin. Nutri., 1992, 141–147.

Yuka Kishimoto, et al., "Effects of Intravenous Injection and Intraperitoneal Continual Administration of Sodium Propionate on Serum Cholesterol Levels in Rats", J. Nutri. Sci. Vitaminol., 1995, 73–81.

Yuka Kishimoto, et al., "Hypocholesterol Effect of Dietary Fiber: Relation to Intestinal Fermentation and Bile Acid Excretion", J. Nutr. Sci. Vitaminol., 1995, 151–161.

K. Tokunaga, "Effect of a Food for Specified Health Use (FOSHU) Which Contains Indisgestible Dextrin as an Effective Ingredient on Glucose and Lipid Metabolism", J. Japan Diab. Soc., 1999, 61–65.

S. Wakabayashi, et al., "Effect of Indigestible Dextrin on Sugar Tolerance: II. Effect of Continuous Administration in Rats Fed on a High Sucrose Diet", J. Japan Diab. Soc., 1992, 873–880.

S. Wakabayashi, "The Effects of Indigestible Dextrin on Sugar Tolerance: III. Improvement in Sugar Tolerance by Indigestible Dextrin on the Impaired Glucose Tolerance Model", Folia Endocrinol., 1993, 594–608.

S. Wakabayashi, "The Effects of Indigestible Dextrin on Sugar Tolerance: I. Studies on Digestion–Absorption and Sugar Tolerance", Folia Endocrinol., 1992, 623–635.

S. Wakabayashi, "Effects of Indigestible Dextrin on Glucose Tolerance in Rats", Journal of Endocrinology, 1995, 533–538.

S. Wakabayashi, et al., "Acute Toxicity and Mutagenicity Studies of Indigestible Dextrin, and Its Effect on Bowel Movement of the Rat", J. Food Hyg. Soc. Japan, 1992, 557–562.

M. Satouchi, et al., "Effect of Indigestible Dextrin on Bowel Movements", Jpn. J. Nutrition, 1993, 31–37.

Labell, F., "Functional Nutritional Fiber," Prepared Foods, 164(11):87 (1995).

Benefiber Product Label (1999).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

Claims 2 and 10 are cancelled.

Claims 1, 3-9 and 11-111 were not reexamined.

* * * * *